US009580684B2

(12) United States Patent
Sharpe et al.

(10) Patent No.: US 9,580,684 B2
(45) Date of Patent: Feb. 28, 2017

(54) METHODS AND COMPOSITIONS FOR THE GENERATION AND MAINTENANCE OF REGULATORY T CELLS

(75) Inventors: Arlene Sharpe, Brookline, MA (US); Loise M. Francisco, Belmont, MA (US); Vijay Kuchroo, Newton Center, MA (US)

(73) Assignees: President and Fellows of Harvard College, Cambridge, MA (US); The Brigham and Women's Hospital, Inc., Boston, MA (US)

( * ) Notice: Subject to any disclaimer, the term of this patent is extended or adjusted under 35 U.S.C. 154(b) by 988 days.

(21) Appl. No.: 13/223,372

(22) Filed: Sep. 1, 2011

(65) Prior Publication Data

US 2012/0076805 A1 Mar. 29, 2012

Related U.S. Application Data

(63) Continuation of application No. PCT/US2010/026498, filed on Mar. 8, 2010.

(60) Provisional application No. 61/157,995, filed on Mar. 6, 2009.

(51) Int. Cl.
| | |
|---|---|
| C12N 5/00 | (2006.01) |
| C12N 5/0783 | (2010.01) |
| A61K 35/12 | (2015.01) |

(52) U.S. Cl.
CPC ....... *C12N 5/0636* (2013.01); *A61K 2035/122* (2013.01); *C12N 2501/15* (2013.01); *C12N 2501/48* (2013.01); *C12N 2501/51* (2013.01); *C12N 2501/515* (2013.01)

(58) Field of Classification Search
None
See application file for complete search history.

(56) References Cited

U.S. PATENT DOCUMENTS

| | | | | |
|---|---|---|---|---|
| 2002/0102651 | A1* | 8/2002 | Freeman et al. | 435/69.1 |
| 2003/0039653 | A1* | 2/2003 | Chen et al. | 424/155.1 |
| 2004/0110290 | A1* | 6/2004 | June et al. | 435/372 |
| 2004/0180047 | A1 | 9/2004 | Chen et al. | |
| 2006/0034810 | A1* | 2/2006 | Riley et al. | 424/93.21 |
| 2006/0269526 | A1* | 11/2006 | Galipeau et al. | 424/93.7 |
| 2007/0172504 | A1* | 7/2007 | Shirwan et al. | 424/277.1 |
| 2008/0241174 | A1 | 10/2008 | Umetsu et al. | |
| 2010/0028450 | A1* | 2/2010 | Vasu | 424/491 |
| 2010/0215674 | A1* | 8/2010 | Thielemans et al. | 424/184.1 |

OTHER PUBLICATIONS

Luo, et al., "Cutting Edge: TGF-β-Induced Expression of Foxp3 in T Cells is Mediated Thorough Inactivation of ERK," The Journal of Immunology, 2008, 180: 2757-2761.
Marie, et al., "TGF-β1 Maintains Suppressor Function and Foxp3 Expression in CD4+CD25+ Regulatory T Cells," The Journal of Experimental Medicine, vol. 201, No. 7, Apr. 4, 2005, 1061-1067.
Nakanishi, et al., "Overexpression of B7-H1 (PD-L1) Significantly Associates With Tumor Grade and Postoperative Prognosis in Human Urothelial Cancers," Cancer Immunol Immunother (2007) 56: 1173-1182.
Nomi, et al., "Clinical Significance and Therapeutic Potential of the Programmed Death-1 Ligand/Programmed Death-1 Pathway in Human Pancreatic Cancer," Clin Cancer Res 2007; 13(7) Apr. 1, 2007.
Ohigashi, et al., "Clinical Significance of Programmed Death-1 Ligand-1 and Programmed Death-1 Ligand-2 Expression in Human Esophageal Cancer," Clin Cancer Res 2005; 11(8) Apr. 15, 2005.
Probst, et al., "Resting Dendritic Cells Induce Peripheral CD8+ T Cell Tolerance Through PD-1 and CTLA-4," Nature Immunology, vol. 6, No. 3, Mar. 2005.
Pyzik, et al., "TGF-β Modulates Foxp3 Expression and Regulatory Activity in Distinct CD4+ T Cell Subsets," Journal of Leukocyte Biology, vol. 82, Aug. 2007.
Qu, et al., "The Effect of Immunosuppressive Drug Rapamycin on Regulatory CD4+CD25+Foxp3+T Cells in Mice," Transplant Immunology, 17 (2007) 153-161.
Ramsdell, Fred, "Foxp3 and Natural Regulatory T Cells: Key to a Cell Lineage?" Immunity, vol. 19, 165-168, Aug. 2003.
Riley, et al., "Modulation of TCR-Induced Transcriptional Profiles by Ligation of CD28, ICOS, and CTLA-4 Receptors," PNAS, Sep. 3, 2002, vol. 99, No. 18, 11790-11795.
Roncarolo, et al. "Regulatory T-Cell Immunotherapy for Tolerance to Self Antigens and Alloantigens in Humans," Nature Reviews Immunology, vol. 7, Aug. 2007.
Rubstov, et al., "TGFβ Signalling in Control of T-Cell-Mediated Self-Reactivity," Nature Reviews Immunology, vol. 7, Jun. 2007.
Sakaguchi, et al., "Immunologic Self-Tolerance Maintained by Activated T Cells Expressing IL-2 Receptor α-Chains (CD25)," The Journal of Immunology, 1995, 155: 1151-1164.
Sakaguchi, et al., "Regulatory T Cells and Immune Tolerance," Cell, 133, May 30, 2008.
Sauer, et al., "T Cell Receptor Signaling Controls Foxp3 Expression via PI3K, Akt, and mTOR," PNAS, Jun. 3, 2008, vol. 105, No. 22, 7797-7802.
Saunders, et al., "PD-L2:PD-1 Involvement in T Cell Proliferation, Cytokine Production, and Integrin-Mediated Adhesion," Eur. J. Immunol., 2005, 35: 3561-3569.
Schubert, et al., "Scurfin (FOXP3) Acts as a Repressor of Transcription and Regulates T Cell Activation," The Journal of Biological Chemistry, vol. 276, No. 40, Oct. 5, 2001, 37672-37679.
Setoguchi, et al., "Homeostatic Maintenance of Natural Foxp3+ CD25+ CD4+ Regulatory T Cells by Interleukin (IL)-2 and Induction of Autoimmune Disease by IL-2 Neutralization," The Journal of Experimental Medicine, vol. 201, No. 5, Mar. 7, 2005, 723-735.
Sharpe, et al., "The Function of Programmed Cell Death 1 and its Ligands in Regulating Autoimmunity and Infection," Nature Immunology, vol. 8, No. 3, Mar. 2007.
Strauss, et al., "Selective Survival of Naturally Occurring Human CD4+CD25+Foxp3+ Regulatory T Cells Cultured with Rapamycin," The Journal of Immunology, 2007, 178: 320-329.
Strome, et al., "B7-H1 Blockage Augments Adoptive T-Cell Immunotherapy for Squamous Cell Carcinoma," Cancer Research, 63, 6501-6505, Oct. 1, 2001.
Tang, et al., "Cutting Edge: CD28 Controls Peripheral Homeostasis of CD4+CD25+ Regulatory T Cells," The Journal of Immunology, 2003, 171: 3348-3352.

(Continued)

*Primary Examiner* — Ilia Ouspenski
(74) *Attorney, Agent, or Firm* — Banner & Witcoff, Ltd.

(57) ABSTRACT

Methods and compositions for generating and maintaining induced regulatory T cells (iTregs) are provided. Methods and compositions for treating an autoimmune disorder, organ transplant rejection, graft versus host disease or allergic or hypersensitivity and inflammation are also provided.

10 Claims, 30 Drawing Sheets

(56) References Cited

OTHER PUBLICATIONS

Tang, et al., "The Foxp3+ Regulatory T Cell: A Jack of All Trades, Master of Regulation," Nature Immunology, vol. 9, No. 3, Mar. 2008.
Thompson, et al., "Costimulatory B7-H1 in Renal Cell Carcinoma Patients: Indicator of Tumor Aggressiveness and Potential Therapeutic Target," PNAS, Dec. 7, 2004, vol. 101, No. 49, 17174-17179.
Vignali, et al., "How Regulatory T Cells Work," Nature Reviews Immunology, vol. 8, Jul. 2008.
Williams, et al., "Maintenance of the Foxp3-Dependent Developmental Program in Mature Regulatory T Cells Requires Continued Expression of Foxp3," Nature Immunology, 8:277, 2007.
Winstead, et al., "Regulatory CD4+CD25+Foxp3+ T Cells Selectively Inhibit the Spontaneous Form of Lymphopenia-Induced Proliferation of Naive T Cells," The Journal of Immunology, 2008, 180: 7305-7317.
Wu, et al., "Immunohistochemical Localization of Programmed Death-1 Ligand-1 (PD-L1) in Gastric Carcinoma and its Clinical Significance," Acta histochemica 108 (2006), 19-24.
Xia, et al., "Ex Vivo-Expanded Natural CD4+CD25+ Regulatory T Cells Synergize With Host T-Cell Depletion to Promote Long-Term Survival of Allografts," American Journal of Transplantation 2008; 8: 298-306.
Yang, et al., "Molecular Antagonism and Plasticity of Regulatory and Inflammatory T Cell Programs," Immunity, 29, 44-56, Jul. 18, 2008.
Zhang, et al., Chemopreventive Agents Induce Programmed Death-1-Ligand 1 (PD-L1) Surface Expression in Breast Cancer Cells and Promote PD-L1-Mediated T Cell Apoptosis, Molecular Immunology, 45 (2008) 1470-1476.
International Search Report and Written Opinion relating to corresponding PCT/US2010/026498.
International Preliminary Report on Patentability relating to corresponding PCT/US2010/026498.
Adler, et al., "Activation of MAP Kinase p38 is Critical for the Cell-Cycle-Controlled Suppressor Function of Regulatory T Cells," Blood, May 15, 2007, vol. 109, No. 10.
Barber, et al., "Restoring Function in Exhausted CD8 T Cells During Chronic Viral Infection," Nature, vol. 439, Feb. 9, 2006.
Battaglia, et al., "Rapamycin Promotes Expansion of Functional CD4+CD25+FOXP3+ Regulatory T Cells of Both Healthy Subjects and Type 1 Diabetic Patients," the Journal of Immunology, 2006, 177: 8338-8347.
Beswick, et al., "Expression of the Programmed Death Ligand 1, B7-H1, on Gastric Epithelial Cells after Helicobacter pylori Exposure Promotes Development of CD4+ CD25+ FoxP3+ Regulatory T Cells," Infection and Immunity, Sep. 2007, 4334-4341, vol. 75, No. 9.
Bettelli, et al., "Myelin Oligodendrocyte Glycoprotein-Specific T Cell Receptor Transgenic Mice Develop Spontaneous Autoimmune Optic Neuritis," J. Exp. Med., vol. 197, No. 9, May 5, 2003, 1073-1081.
Bettelli, et al., "Reciprocal Developmental Pathways for the Generation of Pathogenic Effector TH17 and Regulatory Cells," Nature, vol. 44, May 11, 2006.
Blank, et al., "Interaction of the PD-L1 on Tumor Cells with PD-1 on Tumor Specific T Cells as a Mechanism of Immune Evasion: Implications for Tumor Immunotherapy," Cancer Immunol Immunother (2005) 54: 307-314.
Brunkow, et al., "Disruption of a New Forkhead/Winged-Helix Protein, Scurfin, Results in the Fatal Lymphoproliferative Disorder of the Scurfy Mouse," Nature Genetics, vol. 27, Jan. 2001.
Bloom, et al., "CD4+CD25+FOXP3+ Regulatory T Cells Increase De Novo in Kidney Transplant Patients After Immunodepletion with Campath-1H," American Journal of Transplantation, 2008; 8: 793-802.
Broeren, et al., "Costimulation Light: Activation of CD4+ T Cells with CD80 or CD86 Rather than Anti-CD28 Leads to a Th2 Cytokine Profile," The Journal of Immunology, 2000, 165: 6908-6914.
Brown, et al., "Blockade of Programmed Death-1 Ligands on Dendritic Cells Enhances T Cell Activation and Cytokine Production," The Journal of Immunology, 2003, 170: 1257-1266.
Calzascia, et al., "CD4 T Cells, Lymphopenia, and IL-7 in a Multistep Pathway to Autoimmunity," PNAS, Feb. 26, 2008, vol. 105, No. 8, 2999-3004.
Chen, et al., "Conversion of Peripheral CD4+CD25+ Regulatory T Cells by TGF-β Induction of Transcription Factor Foxp3," The Journal of Experimental Medicine, vol. 198, No. 12, Dec. 15, 2003, 1875-1886.
Coenen, et al., "Rapamycin, not Cyclosporine Permits Thymic Generation and Peripheral Preservation of CD4+CD25+FoxP3+ T Cells," Bone Marrow Transplantation, (2007) 39, 537-545.
Collison, et al., "The Inhibitory Cytokine IL-35 Contributes to Regulatory T-Cell Function," Nature, vol. 450, Nov. 22, 2007.
Coombes, et al., "A Functionally Specialized Population of Mucosal CD103+ DCs Induces Foxp3+ Regulatory T Cells via a TGF-β- and Retinoic Acid-Dependent Mechanism," The Journal of Experimental Medicine, vol. 204, No. 8, Aug. 6, 2007, 1757-1764.
Das, et al., "Expression of B7-H1 on Gastric Epithelial Cells: Its Potential Role in Regulating T Cells During Helicobacter pylori Infection," The Journal of Immunology, 2006, 176: 3000-3009.
Dong, et al., "Tumor-Associated B7-H1 Promotes T-cell Apoptosis: A Potential Mechanism of Immune Evasion," Nature Medicine, vol. 8, No. 8, Aug. 2002.
Dorfman, et al., "Programmed Death-1 (PD-1) is a Marker of Germinal Center-Associated T Cells and Angioimmunoblastic T-Cell Lymphoma," Am J Surg Pathol, vol. 30, No. 7, Jul. 2006.
Fantini, et al., "Cutting Edge: TGF-β Induces a Regulatory Phenotype in CD4+CD25 T Cells Through Foxp3 Induction and Down-Regulation of Smad7," The Journal of Immunology, 2004, 172: 5149-5153.
Fantini, et al., "In Vitro Generation of CD4+CD25+ Regulatory Cells From Murine Naive T Cells," Nature Protocols, vol. 2, No. 7, 2007.
Fontenot, et al., "Foxp3 Programs the Development and Function of CD4+CD25+ Regulatory T Cells," Nature Immunology, vol. 4, No. 4, Apr. 2003.
Fontenot, et al., "Regulatory T Cells Lineage Specification by the Forkhead Transcription Factor Foxp3," Immunity, vol. 22, 329-341, Mar. 2005.
Fontenot, et al., "A Function for Interleukin 2 in Foxp3-Expressing Regulatory T Cells," Nature Immunology, vol. 6, No. 11, Nov. 2005.
Freeman, et al., "Uncovering of Functional Alternative CTLA-4 Counter-Receptor in B7-Deficient Mice," Science, vol. 262, Nov. 5, 2003.
Gao, et al., "Constrasting Effects of Cyclosporine and Rapamycin in De Novo Generation of Alloantigen-Specific Regulatory T Cells," American Journal of Transplantation, 2007, 7: 1722-1732.
Gavin, et al., "Foxp3-Dependent Programme of Regulatory T-Cell Differentiation," Nature, vol. 445, Feb. 15, 2007.
Haxhinasto, et al., "The AKT-mTOR Axis Regulates De Novo Differentiation of CD4+Foxp3+ Cells," The Journal of Experimental Medicine, vol. 205, No. 3, Mar. 17, 2008, 565-574.
Hill, et al., "Foxp3 Transcription-Factor-Dependent and -Independent Regulation of the Regulatory T Cell Transcriptional Signature," Immunity, 27, 1-15, Nov. 2007.
Hirano, et al., "Blockade of B7-H1 and PD-1 by Monoclonal Antibodies Potentiates Cancer Therapeutic Immunity," Cancer Res, 2005, 65: (3), Feb. 1, 2005.
Hori, et al., "Control of Regulatory T Cell Development by the Transcription Factor Foxp3," Science, vol. 299, Feb. 14, 2003.
Huber, et al., "P38 MAP Kinase Signaling is Required for the Conversion of CD4+CD25− T Cells into iTreg," PLoS ONE, Oct. 2008, vol. 3, Issue 10, e3302.
Inman, et al., "PD-L1 (B7-H1) Expression by Urothelial Carcinoma of the Bladder and BCG-Induced Granulomata," Cancer, 2007, 109: 1499-505.
Iwai, et al., "Involvement of PD-L1 on Tumor Cells in the Escape from Host Immune System and Tumor Immunotherapy by PD-L1 Blockade," PNAS, Sep. 17, 2002, vol. 99, No. 19, 12293-12297.

(56) References Cited

OTHER PUBLICATIONS

Joetham, et al., "Plasticity of Regulatory T Cells: Subversion of Suppressive Function and Conversion to Enhancement of Lung Allergic Responses," The Journal of Immunology, 2008, 180: 7117-7124.

Keir, et al., "Tissue Expression of PD-L1 Mediates Peripheral T Cell Tolerance," The Journal of Experimental Medicine, vol. 203, No. 4, Apr. 17, 2006.

Keir, et al., "PD-1 Regulates Self-Reactive CD8+ T Cell Responses to Antigen in Lymph Nodes and Tissues," The Journal of Immunology, 2007, 179: 5064-5070.

Keir, et al., "PD-1 and Its Ligands in T-Cell Immunity," Current Opinion in Immunology, 2007, 19:309-314.

Keir, et al., "PD-1 and Its Ligands in Tolerance and Immunity," Annu. Rev. Immunol., 2008, 26:677-704.

Kim, et al., "Regulatory T Cells Prevent Catastrophic Autoimmunity Throughout the Lifespan of Mice," Nature Immunology, vol. 8, No. 2, Feb. 2007.

Konishi, et al., "B7-H1 Expression on Non-Small Cell Lung Cancer Cells and Its Relationship with Tumor-Infiltrating Lymphocytes and Their PD-1 Expression," Clinical Cancer Research, vol. 10, 5094-5100, Aug. 1, 2004.

Kronenberg, et al., "Regulation of Immunity by Self-Reactive T Cells," Nature, vol. 435, Jun. 2, 2005.

Krupnick, et al., "Cutting Edge: Murine Vascular Endothelium Activates and Induces the Generation of Allogeneic CD4+25+Foxp3+ Regulatory T Cells," The Journal of Immunology, 2005, 175: 6265-6270.

Latchman, et al., "PD-L1-Deficient Mice Show that PD-L1 on T Cells, Antigen-Presenting Cells, and Host Tissues Negatively Regulates T Cells," PNAS, Jul. 20, 2004, vol. 101, No. 29, 10691-10696.

Liang, et al., "Conversion of CD4+ CD25− Cells into CD4+ CD25+ Regulatory T Cells in Vivo Requires B7 Costimulation, but not the Thymus," The Journal of Experimental Medicine, vol. 201, No. 1, Jan. 3, 2005, 127-137.

Lin, et al., "Regulatory T Cell Development in the Absence of Functional Foxp3," Nature Immunology, vol. 8, No. 4, Nov. 2007.

Lohr, et al., "Regulatory T Cells in Periphery," Immunological Reviews, 2006, vol. 212: 149-162.

Long, et al., "Combination of Rapamycin and IL-2 Increases De Novo Induction of Human CD4+CD25+FOXP3+ T Cells," Journal of Autoimmunity, 30 (2008) 293-302.

Baecher-Allan, et al., "CD4+CD25+ Regulatory Cells From Human Peripheral Blood Express Very High Levels of CD25 Ex Vivo," Generation and Effector Functions of Regulatory Lymphocytes: Novartis Foundation Symposium, 2003, vol. 252, 67-91.

* cited by examiner

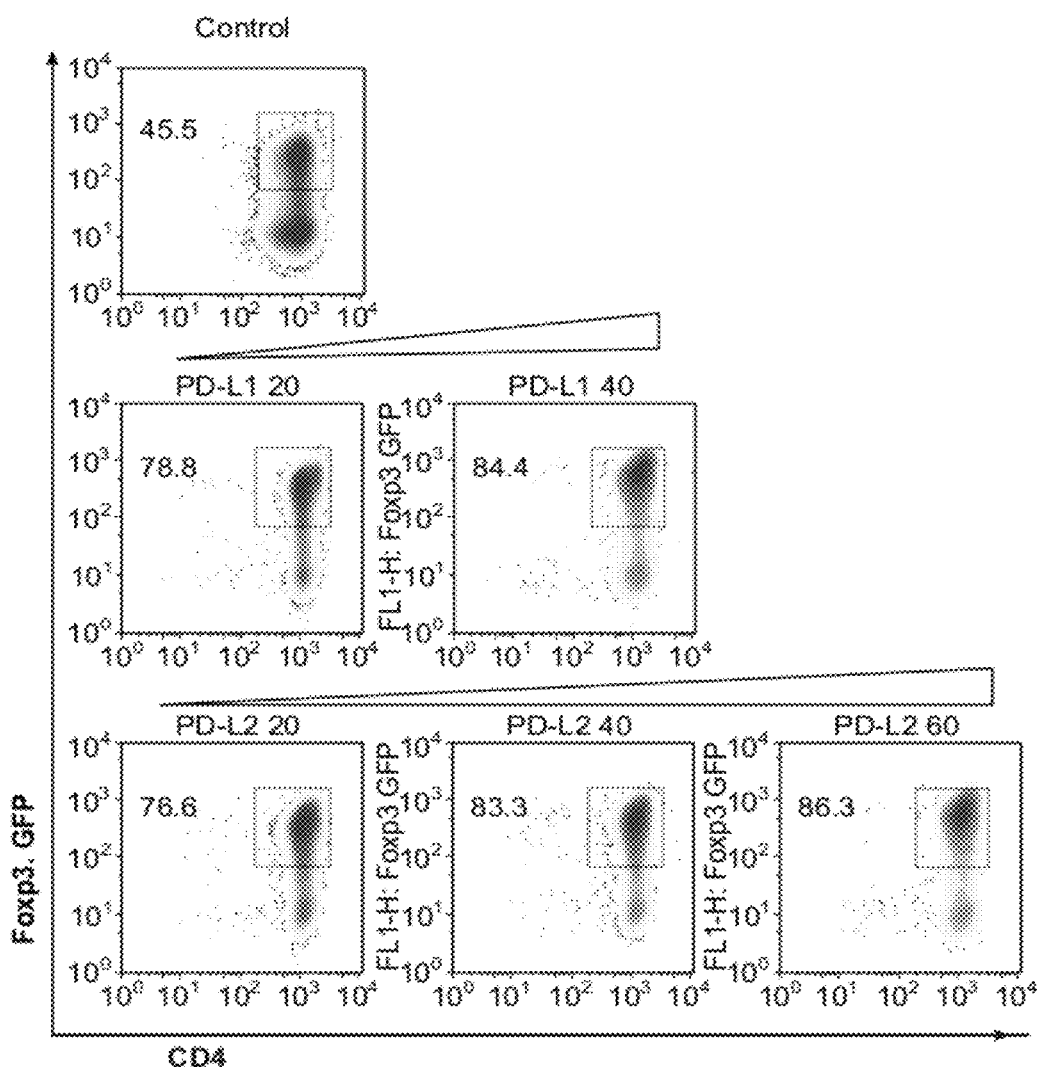

METHODS AND COMPOSITIONS FOR THE GENERATION AND MAINTENANCE OF REGULATORY T CELLS

RELATED APPLICATION DATA

This application is a continuation of PCT application number PCT/US2010/026498 designating the United States and filed Mar. 8, 2010 which claims priority from U.S. provisional patent application No. 61/157,995, filed Mar. 6, 2009, both of which are hereby incorporated herein by reference in its entirety for all purposes.

STATEMENT OF GOVERNMENT INTERESTS

This invention was made with government support under R37AI038310, R01 AI40614, P01 AI056299 and P01 AI39671 awarded by the National Institutes of Health. The Government has certain rights in the invention.

FIELD

The present invention relates to methods and compositions for inducing and maintaining regulatory T cells, and treating diseases, symptoms or conditions associated with autoimmune diseases and disorders, organ transplant rejection, graft versus host disease, pathogenic inflammation and allergic or hypersensitivity responses.

BACKGROUND

Regulatory T cells (Tregs) are key mediators of peripheral tolerance that can actively suppress effector T cells, inhibit inflammation and mediate self-tolerance (Kronenberg et al. (2005) *Nature* 435:598; Sakaguchi et al. (2008) *Cell* 133:775; Tang et al. (2008) *Nat. Immunol.* 9:239). Tregs are essential in the maintenance of peripheral tolerance, and roles for B7:CD28 family members during Treg development are emerging (Tang et al. (2003) *J. Immunol.* 171:3348; Liang et al. (2005) *J. Exp. Med.* 201:127).

Foxp3 is a transcription factor only expressed in the Treg cell lineage (Hori et al. (2003) *Science* 299:1057; Fontenot et al. (2003) *Nat. Immunol.* 4:330; Vignali et al. (2008) *Nat. Rev. Immunol.* 8:523). Along with contributing a distinct genetic signature to regulatory T cells, Foxp3 conveys regulatory activity to nTregs, iTregs, and, upon ectopic expression, in conventional T cells (Hori et al. (2003) *Science* 299:1057; Fontenot et al. (2003) *Nat. Immunol.* 4:330; Gavin et al. (2007) *Nature* 445:771; Schubert et al. (2001) *J. Biol. Chem.* 276:37672; (Hill et al. (2007) *Immunity* 27:786; Fontenot et al. (2005) *Immunity* 22:329).

The pathway consisting of the receptor programmed death-1 (PD-1) and its ligands, PD-1 ligand-1 (PD-L1) and PD-1 ligand-2 (PD-L2) (B7-DC; CD273) is a recently discovered pathway in the B7:CD28 family that regulates the balance between stimulatory and inhibitory signals needed for effective immunity and the maintenance of self-tolerance (Keir et al. (2007) *Curr. Opin. Immunol.* 19:309; Keir et al. (2008) *Annu. Rev. Immunol.* 26:677). PD-1 is upregulated on T cells upon activation and its ligands have distinct expression patterns, with PD-L1 being expressed much more broadly than PD-L2. PD-L1 is constitutively expressed on murine antigen presenting cells (including dendritic cells, macrophages and B cells) and T cells. Human PD-L1 is induced upon activation. PD-L1 is also expressed on a wide variety of hematopoietic and non-hematopoietic cell types, including vascular endothelial cells, pancreatic islet cells, and at sites of immune privilege including the placenta and eye (Keir et al. (2008) *Annu Rev Immunol* 26:677). In contrast, PD-L2 is inducibly expressed on DCs and macrophages.

PD-1: PD-L interactions regulate peripheral CD4 and CD8 T cell tolerance at multiple checkpoints. PD-1 exerts its effects during the initial phase of activation and expansion of self-reactive T cells, attenuating self-reactive T cell responses during presentation of self-antigen to naïve self-reactive T cells by DCs. For example, loss of PD-1 enhances the responses of naïve self-reactive CD8 T cells upon encounter of dendritic cells (DC) bearing self-antigen (Keir et al. (2007) *J. Immunol.* 179:5064). In addition, PD-L1 has a role in inhibiting self-reactive effector T cell function. Bone marrow chimera studies have shown that PD-L1 on non-hematopoietic cells mediates tissue tolerance, controlling the intensity of T cell effector responses in non-lymphoid organs and shielding tissues from potentially pathogenic self-reactive T cells and immune-mediated tissue damage (Keir et al. (2006) *J. Exp. Med.* 203:883).

There is great interest in generating regulatory T cells ex vivo as a therapy for autoimmune diseases and transplant rejection (Roncarolo et al. (2007) *Nat. Rev. Immunol.* 7:585). However, recent studies indicate that Tregs may have functional plasticity and produce pro-inflammatory cytokines at the site of inflammation (Yang et al. (2008) *Immunity*; Joetham et al. (2008) *J. Immunol.* 180:7117). Thus, in order for Treg therapy to be a viable approach, it is desirable to find ways to maintain and enhance the suppressive function of Tregs.

SUMMARY

The experiments presented herein indicate that administration of PD-L (e.g., PD-L1 and/or PD-L2) agonists could provide a novel means for sustaining and enhancing the function of T regulatory cells in vivo. Embodiments of the present invention are directed to the use of PD-Ls (e.g., PD-L1 and/or PD-L2) to induce or differentiate naïve T cells, and in particular CD4$^+$ Foxp3$^-$ T cells, toward a regulatory T cell phenotype. Further embodiments are directed to the use of PD-L1 to sustain, maintain and enhance the function of T regulatory cells in vivo. According to certain embodiments, PD-L-induced (e.g., PD-L1- and/or PD-L2-induced) Tregs not only express the cardinal Treg transcription factor, Foxp3, but also suppress effector T cell activation in vitro. According to certain other embodiments, PD-Ls (e.g., PD-L1 and/or PD-L2) deliver signals that sustain Foxp3 expression by induced regulatory T cells (iTregs) and enhances suppressive activity at lower iTreg to Teff ratios in vitro. The critical role for PD-L1 in promoting regulatory T cell development and maintaining regulatory T cell function was confirmed by the rapid development of pervasive and fatal multi-organ inflammation following transfer of naïve CD4 T cells into PD-L1$^{-/-}$PD-L2$^{-/-}$Rag$^{-/-}$ mice. iTreg conversion was impaired significantly in PD-L1$^{-/-}$PD-L2$^{-/-}$ recipients compared to wild-type (WT) Rag$^{-/-}$ recipients, resulting in the skewing of the Teff:Treg ratio. Accordingly, embodiments of the present invention are directed to a methods where PD-Ls (e.g., PD-L1 and/or PD-L2) mediates peripheral tolerance by stimulating induced-T regulatory cell development via maintaining Foxp3 expression and by enhancing iTreg function.

In certain exemplary embodiments, a method of generating an iTreg is provided. The method includes the steps of providing a naïve T cell, and contacting the naïve T cell with a PD-L (e.g., PD-L1 and/or PD-L2) to induce or differentiate the naïve T cell into an iTreg. In certain aspects, the PD-L (e.g., PD-L1 and/or PD-L2) is immobilized (e.g., on a bead or on a cell). In other aspects, the step of contacting is performed in the presence of one or both of anti-CD3 antibody and anti-CD28 antibody, one or both of which may optionally be present on a bead. In certain aspects, the step of contacting that leads to differentiation is performed in the presence of transforming growth factor-beta (TGF-β). In other aspects, iTreg expresses forkhead box p3 (Foxp3) and/or suppresses effector T cell (Teff) (e.g., CD4$^+$ Teff) activation. In certain aspects, the PD-L antagonizes the Akt signaling pathway.

In certain exemplary embodiments, a method of culturing a Treg is provided. The method includes the steps of providing a Treg and incubating the Treg in the presence of PD-L (e.g., PD-L1 and/or PD-L2), such that the Treg retains one or more Treg phenotypes (e.g., expressing Foxp3 and suppressing Teff activation). In certain aspects, the Treg is obtained by contacting a naïve T cell with PD-L (e.g., PD-L1 and/or PD-L2) to induce the naïve T cell to develop into a Treg, such as by differentiation.

In certain exemplary embodiments, a method of ameliorating, preventing and/or treating diseases, symptoms and/or disorders associated with an autoimmune disorder, organ transplant rejection, graft versus host disease or allergic or hypersensitivity response is provided in which an individual in need thereof is contacted with exogenous PD-L (e.g., PD-L1 and/or PD-L2), such as by administration to the individual, to stimulate iTreg development, such that one or more diseases, symptoms and/or disorders associated with the autoimmune disorder, organ transplant rejection, graft versus host disease or allergic or hypersensitivity response is reduced or prevented in the individual. Diseases, symptoms and/or disorders associated with the autoimmune disorder, organ transplant rejection, graft versus host disease or allergic or hypersensitivity response are known to those of skill in the art. In certain aspects, Foxp3 expression is increased in the individual. In other aspects, Teff activation is suppressed in the individual. In certain aspects, the Akt signaling pathway is suppressed in the individual.

In certain exemplary embodiments, a method of ameliorating, preventing and/or treating diseases, symptoms and/or disorders associated with an autoimmune disorder, organ transplant rejection, graft versus host disease or allergic or hypersensitivity response is provided in which an individual in need thereof is contacted with an exogenous iTreg, such as by administration to the individual, such that one or more diseases, symptoms and/or disorders associated with the autoimmune disorder, organ transplant rejection, graft versus host disease or allergic or hypersensitivity response is reduced or prevented in the individual. Diseases, symptoms and/or disorders associated with the autoimmune disorder, organ transplant rejection, graft versus host disease or allergic or hypersensitivity response are known to those of skill in the art. In certain aspects, Foxp3 expression is increased in the individual. In other aspects, Teff activation is suppressed in the individual. In certain aspects, the Akt signaling pathway is suppressed in the individual.

In certain exemplary embodiments, a method of ameliorating, preventing and/or treating diseases, symptoms and/or disorders associated with an autoimmune disorder, organ transplant rejection, graft versus host disease or allergic or hypersensitivity response is provided in which an individual in need thereof is contacted with a compound that stimulates one or more PD-L (e.g., PD-L1 and/or PD-L2) activities in said individual. Diseases, symptoms and/or disorders associated with an autoimmune disorder, organ transplant rejection, graft versus host disease or allergic or hypersensitivity response are known to those of skill in the art. In certain aspects, the compound is a PD-L (e.g., PD-L1 and/or PD-L2) or PD-1 agonist (e.g., a monoclonal antibody against PD-1) In certain aspects, a mAb against PD-1 delivers a signal into naïve T cells after activation or into regulatory T cells that express PD-1.

In an additional aspect of certain exemplary embodiments, a method of ameliorating, preventing and/or treating immune responses in tissue, such as placenta, skin, eye, and any other tissue subject to an immune response and in need of treatment is provided in which an individual in need thereof is contacted with exogenous PD-L (e.g., PD-L1 and/or PD-L2) or exogenous iTreg, such as by administration to the individual, at the site of tissue inflammation such that the immune response and associated conditions, such as inflammation, are reduced. Other conditions associated with immune responses are known to those of skill in the art. Administration includes modes of administration discussed herein and including topical administration and also by injection intravenously, intradermally, subcutaneously, etc. Embodiments of the present invention are further directed to methods of treating pathogenic inflammation in which an individual in need thereof is contacted with exogenous PD-L (e.g., PD-L1 and/or PD-L2) or exogenous iTreg, such as by administration to the individual, at the site of tissue inflammation such that the inflammation is reduced. According to these methods, the exogenous PD-L (e.g., PD-L1 and/or PD-L2) promotes de novo generation of iTreg and maintains their suppressive function. In addition, the PD-L (e.g., PD-L1 and/or PD-L2) also maintains suppressive function of exogenous iTreg. According to an additional embodiment, the administered PD-L (e.g., PD-L1 and/or PD-L2) inhibits immune responses, for example by reverse-signaling into PD-L- (e.g., PD-L1- and/or PD-L2-) receptor-expressing hematopoietic or non-hematopoietic cells.

Another aspect of certain exemplary embodiments is directed to a method of generating differentiating the naïve T cell into an iTreg by contacting the naïve T cell with an anti-PD-L monoclonal antibody (mAb). In certain aspects, the iTreg expresses Foxp3. In other aspects, the mAb is an anti-PD-L1 antibody or an anti-PD-L2 antibody.

Further features and advantages of certain embodiments of the present invention will become more fully apparent in the following description of the embodiments and drawings thereof, and from the claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The foregoing and other features and advantages of the present invention will be more fully understood from the following detailed description of illustrative embodiments taken in conjunction with the accompanying drawings in which:

FIGS. 13A-13B depict PD-L2 induction of adaptive Treg development as effectively and efficiently as PD-L1. Naïve CD4$^+$CD62L$^+$Fox3.GFP− T cells were cultured with either PD-L1, PD-L2 or control bead in the presence of TGF-β with or without IL-2. Various concentrations of PD-Ligands were covalently attached to the epoxy beads. (A) No IL-2, (B), with IL-2.

DETAILED DESCRIPTION

Figure 1A:
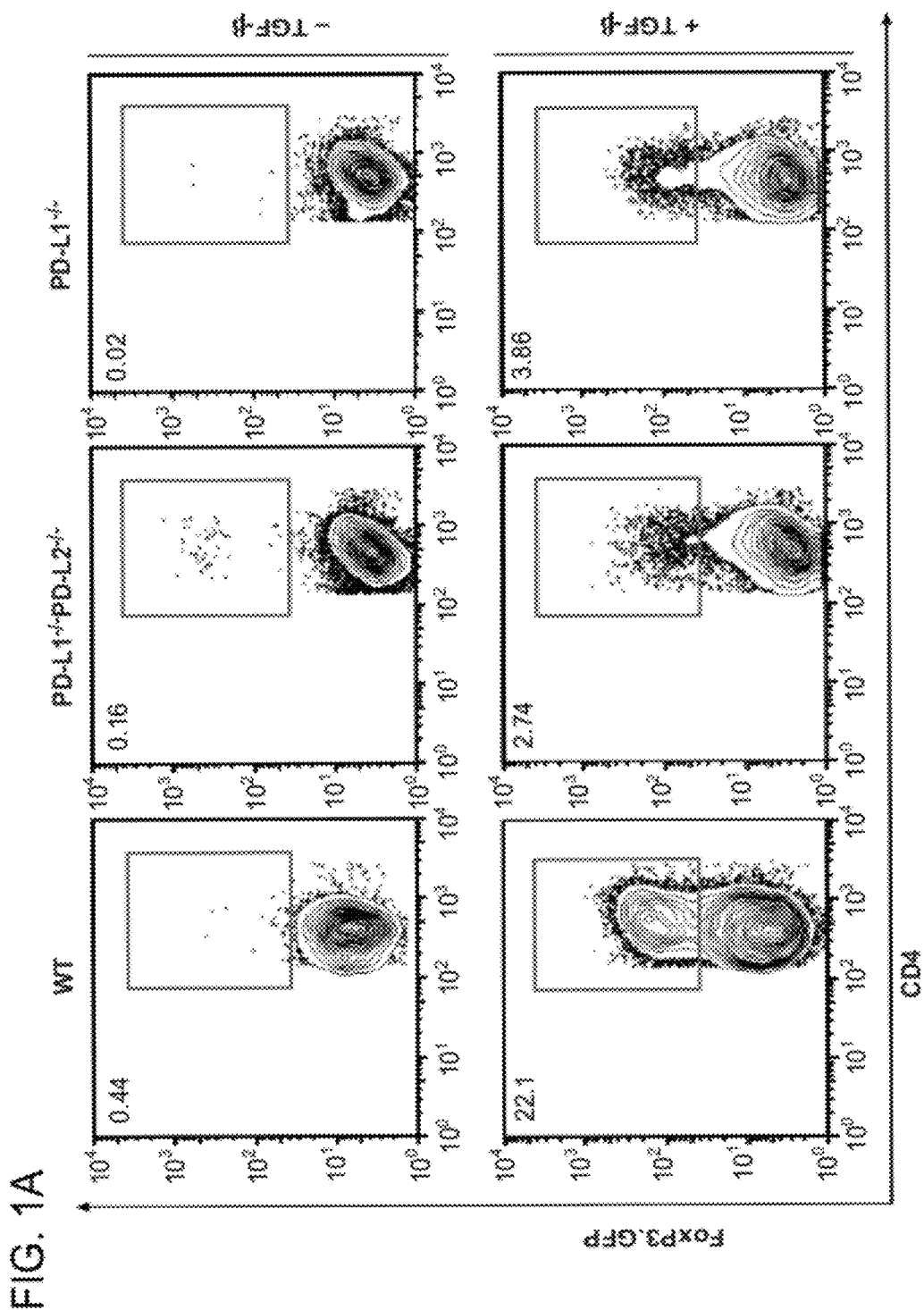
FIGS. 1A-1D depict PD-L1 mediated Foxp3+ induced-regulatory T cell development. Development of Foxp3$^+$ iTregs was assessed by flow cytometric analysis of Foxp3-GFP expression following co-culture of naïve CD4$^+$CD62L$^+$ Foxp3.GFP$^-$ T cells with (A) irradiated WT, PD-L1$^{-/-}$PD-L2$^{-/-}$, or PD-L1$^{-/-}$ antigen presenting cells (APCs) and TGF-β for three days or (B) PD-L1-Ig or Control-Ig (human IgG1) coupled beads. One representative experiment of at least three independent experiments. (C) Analysis of Foxp3-GFP expression following culture of naïve CD4$^+$CD62L$^+$ Foxp3.GFP-T cells with PD-L1-Ig beads and TGF-β at varying quantities of PD-L1-Ig fusion protein. Data represent the mean±s.d. P-values were calculated using Students t-test (P<0.0013 compares various titers of PD-L1-Ig coupled to beads to control bead only (0 PD-L1-Ig) and P<0.049 compares across the titer of PD-L1-Ig. Data represent the mean±s.d. and are representative at least two independent experiments. (D) Analysis of Foxp3-GFP expression following culture of naïve $CD4^+CD62L^+Foxp3$-$GFP^-$ T cells with PD-L1-Ig beads and increasing quantities of TGF-β. *P<0.001 for PD-L1 bead comparing 0 ng/mL TGF-β vs. 0.5-8 ng/mL. **P<0.001 comparing PD-L1 bead vs. control bead at 0.5 ng/mL TGF-β. Data represent the mean±s.d. and are representative of two independent experiments.

Tregs can be divided into naturally occurring and adaptive Tregs. CD4$^+$ naturally occurring regulatory T cells (nTreg) develop in the thymus, express the hallmark transcription factor forkhead box p3 (Foxp3) (Hori et al. (2003) *Science* 299:1057; Fontenot et al. (2003) *Nat. Immunol.* 4:330), high levels of CD25, and have a TCR repertoire biased for self-antigens. In contrast, adaptive regulatory T cells develop in the periphery. In the presence of TGF-β, naïve CD4$^+$ Foxp3$^-$ T cells are converted or induced toward an adaptive Treg fate (Rubtsov et al. (2007) *Nat. Rev. Immunol.* 7:443; Chen et al. (2003) *J. Exp. Med.* 198:1875; Fantini et al. (2004) *Immunol.* 172:5149; Coombes et al. (2007) *J. Exp. Med.* 204:1757). These TGF-β-induced Tregs (iTregs) express Foxp3, and like nTreg, also express high levels of CD25, CTLA-4, and GITR, require prior stimulation for Treg activity and potently suppress effector T cells (Lohr et al. (2006) *Immunol. Rev.* 212:149). Programmed death 1 receptor (PD-1, CD279) and its ligand PD-L1 (B7-H1; CD274), also are highly expressed on regulatory T cells. Accordingly, the principles of the present invention may be applied with particular advantage in generating and maintaining immune cells with inhibitory properties (e.g., induced regulatory T cells (iTregs)).

As used herein, the term "immune cell" is intended to include, but is not limited to, a cell that is of hematopoietic origin and that plays a role in the immune response. Immune cells include, but are not limited to, lymphocytes, such as B cells and T cells; natural killer cells; and myeloid cells, such as monocytes, macrophages, eosinophils, mast cells, basophils, and granulocytes.

The term "antigen presenting cell" includes professional antigen presenting cells (e.g., B lymphocytes, monocytes, dendritic cells, and Langerhans cells) as well as other antigen presenting cells (e.g., keratinocytes, endothelial cells, astrocytes, fibroblasts, and oligodendrocytes).

As used herein, the term "immune response" includes, but is not limited to, T cell-mediated and/or B cell-mediated immune responses that are influenced by modulation of T cell costimulation. Exemplary immune responses include B cell responses (e.g., antibody production) T cell responses (e.g., cytokine production, and cellular cytotoxicity) and activation of cytokine responsive cells, e.g., macrophages. As used herein, the term "down-modulation" with reference to the immune response includes a diminution in any one or more immune responses, while the term "up-modulation" with reference to the immune response includes an increase in any one or more immune responses. It will be understood that up-modulation of one type of immune response may lead to a corresponding down-modulation in another type of immune response. For example, up-modulation of the production of certain cytokines (e.g., IL-10) can lead to down-modulation of cellular immune responses.

In certain exemplary embodiments, methods of performing one or more of ex vivo T cell induction or differentiation to produce iTregs, T cell (e.g., iTreg) maintenance and/or T cell (e.g., iTreg) expansion are provided. In one exemplary embodiment, a method of ex vivo T cell induction is provided including the steps of isolating of naïve T cells and inducing the naïve T cells to differentiate into iTregs. The iTregs may then be maintained in culture and/or expanded. In certain exemplary embodiments, naïve T cell induction is performed by contacting a naïve T cell with a combination of PD-L (e.g., PD-L1 and/or PD-L2), anti-CD3 and anti-CD28 to induce iTreg development as described further herein. In certain aspects, naïve T cell induction is performed by contacting a naïve T cell with a combination of PD-L (e.g., PD-L1 and/or PD-L2), anti-CD3, anti-CD28 and TGF-β to induce iTreg development as described further herein. In certain exemplary embodiments, naïve T cell induction is performed by contacting a naïve T cell with a combination of one or more PD-L (e.g., PD-L1 and/or PD-L2) agonists included with the PD-L (e.g., PD-L1 and/or PD-L2), anti-CD3, anti-CD28 and/or TGF-β to induce iTreg development. An iTreg cell induced to develop from a naïve T cell, such as by differentiation, will express Foxp3 and/or will have the ability to suppress effector T cell (Teff) activation. Assays for determining expression of Foxp3 and/or suppression of Teff activation are described further herein.

As used herein, the term "PD-L agonist" is intended to include, but is not limited to, a compound that has an affinity for binding to PD-L1 and/or PD-L2 and engaging the PD-1: PD-L1 pathway, the PD-2: PD-L2 pathway, and/or the B7-1 (CD80): PD-L1 pathway.

In certain exemplary embodiments, prior to Treg induction, maintenance and/or expansion, a source of T cells is obtained from a subject. As used herein, the terms "subject," "individual" and "host" are intended to include living organisms such as mammals. Examples of subjects and hosts include, but are not limited to, horses, cows, sheep, pigs, goats, dogs, cats, rabbits, guinea pigs, rats, mice, gerbils, non-human primates (e.g., macaques), humans and the like, non-mammals, including, e.g., non-mammalian vertebrates, such as birds (e.g., chickens or ducks) fish or frogs (e.g., *Xenopus*), and non-mammalian invertebrates, as well as transgenic species thereof.

T cells can be obtained from a number of sources, including, but not limited to, peripheral blood mononuclear cells (PBMCs), bone marrow, lymph node tissue, spleen tissue, and/or tumors. In certain exemplary embodiments, any number of T cell lines available in the art may be used.

In certain exemplary embodiments, T cells can be obtained from blood collected from a subject using any number of techniques known to the skilled artisan. In one preferred embodiment, cells from the circulating blood of an individual are obtained by apheresis or leukapheresis. An apheresis product typically contains lymphocytes, including T cells, monocytes, granulocytes, B cells, other nucleated white blood cells, red blood cells, and platelets. In one embodiment, the cells collected by apheresis may be washed to remove the plasma fraction and to place the cells in an appropriate buffer or media for subsequent processing steps. In another embodiment, the cells are washed with phosphate buffered saline (PBS). In an alternative embodiment, the wash solution lacks calcium and may lack magnesium or may lack many if not all divalent cations. Initial activation steps in the absence of calcium lead to magnified activation. As those of ordinary skill in the art would readily appreciate a washing step may be accomplished by methods known to those in the art, such as by using a semi-automated "flow-through" centrifuge according to the manufacturer's instructions. After washing, the cells may be resuspended in a variety of biocompatible buffers, such as, for example, $Ca^{2+}$-free, $Mg^{2+}$-free phosphate buffered saline (PBS). Alternatively, any undesirable component(s) of the apheresis sample may be removed and the cells directly resuspended in culture medium.

In another embodiment, T cells are isolated from peripheral blood lymphocytes by lysing the red blood cells and depleting the monocytes, for example, by centrifugation through a PERCOLL™ gradient. A specific subpopulation of T cells, such as $CD28^+$, $CD4^+$, $CD8^+$, $CD45RA^+$ and/or $CD45RO^+$ T cells, can be further isolated by positive or negative selection techniques using, e.g., a variety of commercially available beads and/or kits (e.g., Invitrogen).

Isolation of a T cell population by negative selection can be accomplished with a combination of one or more antibodies directed to surface markers unique to the negatively selected cells. In certain exemplary embodiments, cell sorting and/or selection via negative magnetic immunoadherence or flow cytometry using one or more antibodies (e.g., monoclonal antibodies) directed to cell surface markers present on those cells that are negatively selected.

For isolation of a desired population of cells by positive or negative selection, the concentration of cells and binding surface (e.g., particles such as beads) can be varied. In certain embodiments, it may be desirable to significantly decrease the volume in which cells and binding surface (e.g., beads) are mixed together (e.g., to increase the relative concentration of cells) to ensure maximum contact of cells and binding surface (e.g., beads). For example, in one embodiment, a concentration of 2 billion cells/mL is used. In one embodiment, a concentration of 1 billion cells/mL is used. In a further embodiment, greater than 100 million cells/mL is used. In a further embodiment, a concentration of cells of 10, 15, 20, 25, 30, 35, 40, 45, or 50 million cells/mL is used. In yet another embodiment, a concentration of cells from 75, 80, 85, 90, 95, or 100 million cells/mL is used. In further embodiments, concentrations of 125 or 150 million cells/mL can be used. Using high concentrations can result in increased cell yield, cell activation, and cell expansion. Further, use of high cell concentrations allows more efficient capture of cells that may weakly express target antigens of interest, such as $CD28^-$ T cells, or from samples where there are many tumor cells present (i.e., leukemic blood, tumor tissue, etc). Such populations of cells may have therapeutic value and would be desirable to obtain. For example, using high concentration of cells allows more efficient selection of $CD8^+$ T cells that normally have weaker CD28 expression.

In certain exemplary embodiments, it may be desirable to use lower concentrations of cells relative to binding surface (e.g., beads). By diluting the mixture of T cells, interactions between T cells and binding surface (e.g., beads) is minimized. This selects for cells that express high amounts of desired antigens to be bound to the particles. For example, $CD4^+$ T cells express higher levels of CD28 and are more efficiently captured than $CD8^+$ T cells in dilute concentrations. In one embodiment, the concentration of cells used is $5 \times 10^6$/mL. In other embodiments, the concentration used can be from about $1 \times 10^5$/mL to $1 \times 10^6$/mL, and any integer value in between.

If desired or necessary, monocyte populations (e.g., $CD14^+$ cells) may be depleted from blood preparations prior to ex vivo Treg induction, maintenance and/or expansion by a variety of methodologies, including anti-CD14 coated beads or columns, or utilization of the phagocytotic activity of these cells to facilitate removal. Accordingly, in one embodiment, a binding surface (e.g., bead) of a size sufficient to be engulfed by a phagocytotic monocyte is provided. In one aspect, non-specific cells are removed using a binding surface (e.g., bead) having one or more 'irrelevant proteins' (e.g., serum proteins or antibodies) attached thereto. As used herein, the term "irrelevant protein" is intended to include, but is not limited to, proteins, antibodies and/or fragments thereof that do not specifically target the T cells to be induced, maintained and/or expanded. In certain embodiments, a binding surface (e.g., bead) having one or more irrelevant proteins attached thereto includes a bead having any combination of one or more sheep anti-mouse antibodies, goat anti-mouse antibodies, and the like, and human serum albumin attached thereto. One of skill in the art would recognized based on the present disclosure that other suitable antibodies and/or proteins are useful in the practice of the present invention.

In certain exemplary embodiments, depletion of monocytes is performed by pre-incubating PBMC isolated from whole blood or apheresed peripheral blood with one or more varieties of irrelevant protein- or non-antibody-coupled binding surface (e.g., bead) at any concentration that allows for removal of monocytes (e.g., approximately a 20:1 bead:cell ratio), followed by removal of cells which have attached to the binding surface (e.g., bead). In certain aspects, the binding surface is a magnetic bead and a bead having one or more cells attached thereto is removed using a magnet. Such separation can be performed using standard methods available in the art. For example, any magnetic separation methodology may be used including a variety of which are commercially available (e.g., DYNAL™ Magnetic Particle Concentrator (Invitrogen)). Assurance of requisite depletion can be monitored by a variety of methodologies known to those of ordinary skill in the art, including flow cytometric analysis of $CD14^+$ cells, before and after the depletion step.

T cells for ex vivo Treg induction, maintenance and/or expansion can be frozen after the washing step, which would not require a monocyte removal step. After a washing step is performed to remove plasma and platelets, the cells may be suspended in a freezing solution. While a variety of suitable freezing solutions and parameters are known in the art and will be useful in this context, one exemplary method involves using phosphate buffered saline (PBS) containing 20% DMSO and 8% human serum albumin. The cells can then be frozen at −80° C. by cooling the cells at a rate of 1 degree per minute followed by storage in the vapor phase of a liquid nitrogen storage tank. Other methods of controlled freezing may be used, as well as uncontrolled rate freezing at −20° C. or freezing in liquid nitrogen.

As used herein, the term "antibody" refers to immunoglobulin molecules and immunologically active portions of immunoglobulin molecules, i.e., molecules that contain an antigen binding site which specifically binds (immunoreacts with) an antigen, such as an immune cell antigen (e.g., CD3, CD28 or the like). Examples of immunologically active portions of immunoglobulin molecules include F(ab) and F(ab')2 fragments which can be generated by treating the antibody with an enzyme such as pepsin. In certain exemplary embodiments, polyclonal and monoclonal antibodies are provided that bind one or more immune cell antigens (e.g., CD3 and/or CD28). The terms "monoclonal antibody" and "monoclonal antibody composition," as used herein, refer to a population of antibody molecules that contains only one species of an antigen binding site capable of immunoreacting with a particular epitope of an immune cell antigen (e.g., CD3 or CD28). A monoclonal antibody composition thus typically displays a single binding affinity for a particular immune cell antigen (e.g., CD3 or CD28) with which it immunoreacts. A variety of antibodies are commercially available.

Polyclonal anti-immune cell antigen (e.g., CD3 and/or CD28) antibodies can be prepared by immunizing a suitable subject with an immune cell antigen. The anti-immune cell antigen antibody titer in the immunized subject can be monitored over time by standard techniques, such as with an enzyme linked immunosorbent assay (ELISA) using immobilized antigen (e.g., CD3 and/or CD28). If desired, the antibody molecules directed against the antigen can be isolated from the mammal (e.g., from the blood) and further purified by well known techniques, such as protein A chromatography to obtain the IgG fraction. At an appropriate time after immunization, e.g., when the anti-antigen antibody titers are highest, antibody-producing cells can be obtained from the subject and used to prepare monoclonal antibodies by standard techniques, such as the hybridoma technique originally described by Kohler and Milstein (1975) Nature 256:495-497) (see also, Brown et al. (1981) J. Immunol. 127:539-46; Brown et al. (1980) J. Biol. Chem. 255:4980-83; Yeh et al. (1976) Proc. Natl. Acad. Sci. USA 76:2927-31; and Yeh et al. (1982) Int. J. Cancer 29:269-75), the human B cell hybridoma technique (Kozbor et al. (1983) Immunol. Today 4:72), the EBV-hybridoma technique (Cole et al. (1985), Monoclonal Antibodies and Cancer Therapy, Alan R. Liss, Inc., pp. 77-96) or trioma techniques.

The technology for producing monoclonal antibody hybridomas is well known (see generally R. H. Kenneth, in Monoclonal Antibodies: A New Dimension In Biological Analyses, Plenum Publishing Corp., New York, N.Y. (1980); E. A. Lerner (1981) Yale J. Biol. Med. 54:387-402; Gefter et al. (1977) Somatic Cell Genet. 3:231-36). Briefly, an immortal cell line (typically a myeloma) is fused to lymphocytes (typically splenocytes) from a mammal immunized with an antigen, and the culture supernatants of the resulting hybridoma cells are screened to identify a hybridoma producing a monoclonal antibody that binds the antigen. Any of the many well known protocols used for fusing lymphocytes and immortalized cell lines can be applied for the purpose of generating a monoclonal antibody (see, e.g., Galfre et al. (1977) Nature 266:55052; Gefter et al. Somatic Cell Genet., cited supra; Lerner, Yale J. Biol. Med. (supra); Kenneth, Monoclonal Antibodies, (supra)). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Particularly suitable immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O—Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody against a specific antigen are detected by screening the hybridoma culture supernatants for antibodies that bind the antigen, e.g., using a standard ELISA assay.

Alternative to preparing monoclonal antibody-secreting hybridomas, a monoclonal antibody can be identified and isolated by screening a recombinant combinatorial immunoglobulin library (e.g., an antibody phage display library) with antigen to thereby isolate immunoglobulin library members that bind the antigen. Kits for generating and screening phage display libraries are commercially available (e.g., Recombinant Phage Antibody System, Pfizer, New York, N.Y.; and the SURFZAP™ Phage Display Kit, Stratagene, La Jolla, Calif.). Additionally, examples of methods and reagents particularly amenable for use in generating and screening antibody display library can be found in, for example, Ladner et al. U.S. Pat. No. 5,223,409; Kang et al. PCT International Publication No. WO 92/18619; Dower et al. PCT International Publication No. WO 91/17271; Winter et al. PCT International Publication WO 92/20791; Markland et al. PCT International Publication No. WO 92/15679; Breitling et al. PCT International Publication WO93/01288; McCafferty et al. PCT International Publication No. WO 92/01047; Garrard et al. PCT International Publication No. WO 92/09690; Ladner et al. PCT International Publication No. WO 90/02809; Fuchs et al. (1991) Bio/Technology 9:1370-1372; Hay et al. (1992) Hum. Antibod. Hybridomas 3:81-85; Huse et al. (1989) Science 246:1275-1281; Griffiths et al. (1993) EMBO J. 12:725-734; Hawkins et al. (1992) J. Mol. Biol. 226:889-896; Clarkson et al. (1991) Nature 352:624-628; Gram et al. (1992) Proc. Natl. Acad. Sci. USA 89:3576-3580; Garrad et al. (1991) Bio/Technology 9:1373-1377; Hoogenboom et al. (1991) Nucl. Acid Res. 19:4133-4137; Barbas et al. (1991) Proc. Natl. Acad. Sci. USA 88:7978-7982; and McCafferty et al. (1990) Nature 348:552-554.

Additionally, recombinant antibodies, such as chimeric and humanized monoclonal antibodies comprising both human and non-human portions which can be made using standard recombinant DNA techniques, are within the scope of the invention. Such chimeric and humanized monoclonal antibodies can be produced by recombinant DNA techniques known in the art, for example using methods described in Robinson et al. International Application No. PCT/US86/02269; Akira; et al. European Patent Application 184,187; Taniguchi, M., European Patent Application 171,496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al. (1988) *Science* 240:1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci. USA* 84:214-218; Nishimura et al. (1987) *Canc. Res.* 47:999-1005; Wood et al. (1985) *Nature* 314:446-449; and Shaw et al. (1988) *J. Natl. Cancer Inst.* 80:1553-1559); Morrison, S. L. (1985) *Science* 229:1202-1207; Oi et al. (1986) *BioTechniques* 4:214; Winter U.S. Pat. No. 5,225,539; Jones et al. (1986) *Nature* 321:552-525; Verhoeyan et al. (1988) *Science* 239: 1534; and Beidler et al. (1988) *J. Immunol.* 141:4053-4060. Monoclonal and polyclonal antibodies are also commercially available from a variety of vendors (e.g., Abcam, Cambridge, Mass.; Cambridge Bioscience, Cambridge, United Kingdom; Invitrogen, Carlsbad, Calif., Sigma-Aldrich, St. Louis, Mo. and the like).

In certain exemplary embodiments, one or more compounds (e.g., a protein, a ligand, an antibody and the like) described herein can be immobilized on a support. The support can be simple square grids, checkerboard (e.g., offset) grids, hexagonal arrays and the like. Suitable supports include, but are not limited to, slides, beads, chips, particles, strands, gels, sheets, tubing, spheres, containers, capillaries, pads, slices, films, culture dishes, plates (e.g., 96-well, 48-well, 24-well, 12-well, eight-well, six-well, four-well, single-well and the like), cell surfaces (e.g., *S. aureus* cells) and the like. In various embodiments, a solid support may be biological, nonbiological, organic, inorganic, or any combination thereof.

In certain exemplary embodiments, beads and bead-based arrays are provided. As used herein, the term "bead" refers to a discrete particle that may be spherical (e.g., microspheres) or have an irregular shape. Beads may be as small as approximately 0.1 µm in diameter or as large approximately several millimeters in diameter. Beads may comprise a variety of materials including, but not limited to, paramagnetic materials, ceramic, plastic, glass, polystyrene, methylstyrene, acrylic polymers, titanium, latex, sepharose, cellulose, nylon and the like.

In accordance with certain examples, a support (e.g., a bead) may have functional groups attached to its surface which can be used to bind one or more reagents described herein to the bead. One or more reagents can be attached to a support (e.g., a bead) by hybridization, covalent attachment, magnetic attachment, affinity attachment and the like. For example, a support (e.g., a bead) can be coated with a secondary antibody for use with a primary antibody (e.g., anti-CD3 and/or anti-CD28). In another example, a support (e.g., a bead) may be coated with glycidyl ether (epoxy) reactive groups and/or p-toluenesulphonyl (tosyl) reactive groups for use with a primary antibody (e.g., anti-CD3 and/or anti-CD28). A support (e.g., a bead) may be used to separate naïve T cells other cells by depleting non-T cells (e.g., B cells, natural killer cells, monocytes, platelets, dendritic cells, granulocytes, erythrocytes and the like) and activated T cells from peripheral blood mononuclear cells (e.g., using DYNAL® T cell negative isolation kit, Invitrogen). Tregs can be obtained from mononuclear cells, e.g., by using the methods and compositions described herein or by using a commercially available kit (such as DYNA-BEADS® Regulatory $CD4^+CD25^+$ T Cell Kit). Beads coated with a variety of substrates are commercially available (Dynabeads, Invitrogen). Supports (e.g., beads) may also be functionalized using, for example, solid-phase chemistries known in the art (see, e.g., U.S. Pat. No. 5,919,523).

As used herein, the term "attach" refers to both covalent interactions and noncovalent interactions. A covalent interaction is a chemical linkage between two atoms or radicals formed by the sharing of a pair of electrons (i.e., a single bond), two pairs of electrons (i.e., a double bond) or three pairs of electrons (i.e., a triple bond). Covalent interactions are also known in the art as electron pair interactions or electron pair bonds. Noncovalent interactions include, but are not limited to, van der Waals interactions, hydrogen bonds, weak chemical bonds (i.e., via short-range noncovalent forces), hydrophobic interactions, ionic bonds and the like. A review of noncovalent interactions can be found in Alberts et al., in *Molecular Biology of the Cell,* 3d edition, Garland Publishing, 1994.

In certain exemplary embodiments, screening assays for identifying modulators, i.e., candidate or test compounds or agents (e.g., antibodies, peptides, cyclic peptides, peptidomimetics, small molecules, small organic molecules, or other drugs) which have a stimulatory effect on PD-L (e.g., PD-L1 and/or PD-L2) and, optionally: 1) stimulate iTreg development; 2) maintain Foxp3 expression and/or 3) enhance iTreg function are provided. The test compounds of the described herein can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145).

In certain exemplary embodiments, one or more iTregs, one or more PD-L (e.g., PD-L1 and/or PD-L2) polypeptides, one or more nucleic acid sequences encoding one or more PD-L (e.g., PD-L1 and/or PD-L2) polypeptides, one or more PD-L (e.g., PD-L1 and/or PD-L2) agonists, or one or more test compounds, or pharmaceutically acceptable salts thereof described herein are provided in a pharmaceutically acceptable carrier. As used herein, the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions. Pharmaceutically acceptable carriers and their formulations are known to those skilled in the art and described, for example, in Remington's Pharmaceutical Sciences, (19th edition), ed. A. Gennaro, 1995, Mack Publishing Company, Easton, Pa.

In certain exemplary embodiments, pharmaceutical formulations of a therapeutically effective amount of one or more iTregs, one or more PD-L (e.g., PD-L1 and/or PD-L2) polypeptides, one or more nucleic acid sequences encoding one or more PD-L (e.g., PD-L1 and/or PD-L2) polypeptides, one or more PD-L (e.g., PD-L1 and/or PD-L2) agonists, or one or more test compounds, or pharmaceutically acceptable salts thereof, are administered by intravenous injection, intraperitoneal injection, oral administration or by other parenteral routes (e.g. intradermal, subcutaneous, oral (e.g., inhalation), transdermal (topical), transmucosal, and rectal administration), or by intrathecal and intraventricular injections into the CNS, in an admixture with a pharmaceutically acceptable carrier adapted for the route of administration.

Solutions or suspensions used for parenteral, intradermal, subcutaneous or central nervous system application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Methods well known in the art for making formulations are found, for example, in Remington's Pharmaceutical Sciences (19th edition), ed. A. Gennaro, 1995, Mack Publishing Company, Easton, Pa. Compositions intended for oral use may be prepared in solid or liquid forms according to any method known to the art for the manufacture of pharmaceutical compositions. The compositions may optionally contain sweetening, flavoring, coloring, perfuming, and/or preserving agents in order to provide a more palatable preparation. Solid dosage forms for oral administration include capsules, tablets, pills, powders, and granules. In such solid forms, the active compound is admixed with at least one inert pharmaceutically acceptable carrier or excipient. These may include, for example, inert diluents, such as calcium carbonate, sodium carbonate, lactose, sucrose, starch, calcium phosphate, sodium phosphate, or kaolin. Binding agents, buffering agents, and/or lubricating agents (e.g., magnesium stearate) may also be used. Tablets and pills can additionally be prepared with enteric coatings.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, CREMOPHOR EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In certain exemplary embodiments, isotonic agents, for example, sugars, polyalcohols such as mannitol, sorbitol, and/or sodium chloride, will be included in the composition. Prolonged absorption of the injectable compositions can be brought about by including in the composition an agent which delays absorption, for example, aluminum monostearate and gelatin.

Sterile, injectable solutions can be prepared by incorporating one or more iTregs, one or more PD-L (e.g., PD-L1 and/or PD-L2) polypeptides, one or more nucleic acid sequences encoding one or more PD-L (e.g., PD-L1 and/or PD-L2) polypeptides, one or more PD-L (e.g., PD-L1 and/or PD-L2) agonists, or one or more test compounds, or pharmaceutically acceptable salts thereof described herein in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, exemplary methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: A binder such as microcrystalline cellulose, gum tragacanth or gelatin; an excipient such as starch or lactose, a disintegrating agent such as alginic, acid, Primogel, or corn starch; a lubricant such as magnesium stearate or Sterotes; a glidant: such as colloidal silicon dioxide; a sweetening agent such as sucrose or saccharin; or a flavoring agent such as peppermint, methyl salicylate, or orange flavoring.

In one embodiment, one or more iTregs, one or more PD-L (e.g., PD-L1 and/or PD-L2) polypeptides, one or more nucleic acid sequences encoding one or more PD-L (e.g., PD-L1 and/or PD-L2) polypeptides, one or more PD-L (e.g., PD-L1 and/or PD-L2) agonists, or one or more test compounds, or pharmaceutically acceptable salts thereof described herein are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These may be prepared according to methods known to those skilled in the art, for example, as described in U.S. Pat. No. 4,522,811.

Nasal compositions generally include nasal sprays and inhalants. Nasal sprays and inhalants can contain one or more active components and excipients such as preservatives, viscosity modifiers, emulsifiers, buffering agents and the like. Nasal sprays may be applied to the nasal cavity for local and/or systemic use. Nasal sprays may be dispensed by a non-pressurized dispenser suitable for delivery of a metered dose of the active component. Nasal inhalants are intended for delivery to the lungs by oral inhalation for local and/or systemic use. Nasal inhalants may be dispensed by a closed container system for delivery of a metered dose of one or more active components.

In one embodiment, nasal inhalants are used with an aerosol. This is accomplished by preparing an aqueous aerosol, liposomal preparation or solid particles containing the compound. A non-aqueous (e.g., fluorocarbon propellant) suspension could be used. Sonic nebulizers may be used to minimize exposing the agent to shear, which can result in degradation of the compound.

Ordinarily, an aqueous aerosol is made by formulating an aqueous solution or suspension of the agent together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

One or more iTregs, one or more PD-L (e.g., PD-L1 and/or PD-L2) polypeptides, one or more nucleic acid sequences encoding one or more PD-L (e.g., PD-L1 and/or PD-L2) polypeptides, one or more PD-L (e.g., PD-L1 and/or PD-L2) agonists, or one or more test compounds, or pharmaceutically acceptable salts thereof described herein can also be prepared in the form of suppositories (e.g., with conventional suppository bases such as cocoa butter and other glycerides) or retention enemas for rectal delivery.

In one embodiment, one or more iTregs, one or more PD-L (e.g., PD-L1 and/or PD-L2) polypeptides, one or more nucleic acid sequences encoding one or more PD-L (e.g., PD-L1 and/or PD-L2) polypeptides, one or more PD-L (e.g., PD-L1 and/or PD-L2) agonists, or one or more test compounds, or pharmaceutically acceptable salts thereof described herein are prepared with carriers that will protect them against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral, parenteral or CNS direct delivery compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of one or more iTregs, one or more PD-L (e.g., PD-L1 and/or PD-L2) polypeptides, one or more nucleic acid sequences encoding one or more PD-L (e.g., PD-L1 and/or PD-L2) polypeptides, one or more PD-L (e.g., PD-L1 and/or PD-L2) agonists, or one or more test compounds, or pharmaceutically acceptable salts thereof described herein can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

Data obtained from cell culture assays and/or animal studies can be used in formulating a range of dosage for use in humans. The dosage typically will lie within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Monitoring the influence of a pharmaceutical composition on PD-L (e.g., PD-L1 and/or PD-L2) expression and/or activity (e.g., the modulation of iTreg development, maintenance of Foxp3 expression and/or enhancement of iTreg function) can be applied not only in basic drug screening, but also in clinical trials. For example, the effectiveness of a pharmaceutical composition determined by a screening assay as described herein to increase iTreg levels, PD-L (e.g., PD-L1 and/or PD-L2) gene expression, protein levels, or upregulate PD-L (e.g., PD-L1 and/or PD-L2) activity, can be monitored in clinical trials of subjects exhibiting decreased iTreg levels, PD-L (e.g., PD-L1 and/or PD-L2) gene expression, protein levels, and/or downregulated PD-L (e.g., PD-L1 and/or PD-L2) activity. Alternatively, the effectiveness of an agent determined by a screening assay to decrease iTreg levels, PD-L (e.g., PD-L1 and/or PD-L2) gene expression, protein levels, or downregulate PD-L (e.g., PD-L1 and/or PD-L2) activity, can be monitored in clinical trials of subjects exhibiting increased iTreg levels, PD-L (e.g., PD-L1 and/or PD-L2) gene expression, protein levels, and/or upregulated PD-L (e.g., PD-L1 and/or PD-L2) activity.

In certain exemplary embodiments, a method for monitoring the effectiveness of treatment of a subject with an agent (e.g., one or more iTregs, one or more PD-L (e.g., PD-L1 and/or PD-L2) polypeptides, one or more nucleic acid sequences encoding one or more PD-L (e.g., PD-L1 and/or PD-L2) polypeptides, one or more PD-L (e.g., PD-L1 and/or PD-L2) agonists, or one or more test compounds, or pharmaceutically acceptable salts thereof) including the steps of (i) obtaining a pre-administration sample from a subject prior to administration of the agent; (ii) detecting the level of expression and/or activity of a PD-L (e.g., PD-L1 and/or PD-L2) protein, mRNA, or genomic DNA in the preadministration sample; (iii) obtaining one or more post-administration samples from the subject; (iv) detecting the level of expression and/or activity of the PD-L (e.g., PD-L1 and/or PD-L2) protein, mRNA, or genomic DNA in the post-administration samples; (v) comparing the level of expression and/or activity of the PD-L (e.g., PD-L1 and/or PD-L2) protein, mRNA, or genomic DNA in the pre-administration sample with the PD-L (e.g., PD-L1 and/or PD-L2) protein, mRNA, or genomic DNA in the post administration sample or samples; and (vi) altering the administration of the agent to the subject accordingly, is provided. For example, increased administration of the agent may be desirable to increase the expression and/or activity of PD-L1 to higher levels than detected, e.g., to increase the effectiveness of the agent. Alternatively, decreased administration of the agent may be desirable to decrease expression and/or activity of PD-L (e.g., PD-L1 and/or PD-L2) to lower levels than detected, e.g., to decrease the effectiveness of the agent. According to such an embodiment, PD-L (e.g., PD-L1 and/or PD-L2) expression or activity may be used as an indicator of the effectiveness of an agent, even in the absence of an observable phenotypic response.

In certain exemplary embodiments, a method for treating, ameliorating and/or preventing in a subject a disease, symptom and/or condition associated with decreased iTreg levels and/or function, PD-L (e.g., PD-L1 and/or PD-L2) expression or activity, by administering to the subject an iTreg, PD-L (e.g., PD-L1 and/or PD-L2) or an agent which modulates PD-L (e.g., PD-L1 and/or PD-L2) expression or at least one PD-L (e.g., PD-L1 and/or PD-L2) activity, is provided. Subjects at risk for a disease which is caused or contributed to by aberrant iTreg levels and/or PD-L (e.g., PD-L1 and/or PD-L2) expression or activity can be identified by, for example, any or a combination of diagnostic or prognostic assays as described herein. Administration of a prophylactic agent can occur prior to the manifestation of symptoms characteristic of decreased iTreg levels and/or function and/or PD-L (e.g., PD-L1 and/or PD-L2) aberrancy, such that a disease or disorder is prevented or, alternatively, delayed in its progression. Depending on the type of iTreg and/or PD-L (e.g., PD-L1 and/or PD-L2) aberrancy, for example, an iTreg, one or more PD-L (e.g., PD-L1 and/or PD-L2) polypeptides, one or more nucleic acid sequences encoding one or more PD-L (e.g., PD-L1 and/or PD-L2) polypeptides, one or more PD-L (e.g., PD-L1 and/or PD-L2) agonists, or one or more test compounds, or pharmaceutically acceptable salts thereof can be used for treating the subject. The appropriate agent can be determined based on screening assays described herein.

In certain exemplary embodiments, a method of modulating iTreg levels and/or function and/or PD-L (e.g., PD-L1 and/or PD-L2) expression and/or activity levels for therapeutic purposes is provided. Accordingly, in an exemplary embodiment, the modulatory method involves contacting a cell or subject with one or more iTregs, one or more PD-L (e.g., PD-L1 and/or PD-L2) polypeptides, one or more nucleic acid sequences encoding one or more PD-L (e.g., PD-L1 and/or PD-L2) polypeptides, one or more PD-L (e.g., PD-L1 and/or PD-L2) agonists, or one or more test compounds, or pharmaceutically acceptable salts thereof. An agent that modulates PD-L (e.g., PD-L1 and/or PD-L2) expression levels and/or activity levels can be an agent as described herein, such as a nucleic acid or a protein, a PD-L (e.g., PD-L1 and/or PD-L2) agonist, a peptidomimetic of a PD-L (e.g., PD-L1 and/or PD-L2) agonist, or other small molecule. In one embodiment, the agent stimulates one or more PD-L (e.g., PD-L1 and/or PD-L2) activities. Examples of such stimulatory agents include active PCIP protein and a nucleic acid molecule encoding PCIP that has been introduced into the cell and/or subject. Modulatory methods can be performed in vitro (e.g., by culturing the cell with the agent) or, alternatively, in vivo (e.g., by administering the agent to a subject).

In certain exemplary embodiments, a method of treating an individual afflicted with a disease or disorder characterized by aberrant iTreg levels and/or aberrant PD-L (e.g., PD-L1 and/or PD-L2) expression and/or activity is provided. Examples of such disorders include autoimmune disorders. As used herein, the term "autoimmune disorder" is a disease or disorder caused by a subject producing an inappropriate immune response against its own tissues. As used herein, an autoimmune disorder includes, but is not limited to, disorders such as Addison's disease, alopecia greata, ankylosing spondylitis, antiphospholipid syndrome, autoimmune hemolytic anemia, autoimmune hepatitis, autoimmune inner ear disease (AIED), autoimmune lymphoproliferative syndrome (ALPS), autoimmune thrombocytopenic purpura (ATP), Balo disease, Bechet disease, bullous pemphigoid, cardiomyopathy, celiac sprue-dermatitis herpetiformis, chronic fatigue immune dysfunction syndrome (CFIDS), chronic inflammatory demyelinating polyneuropathy, cicatricial pemphigoid, cold agglutinin disease, CREST syndrome, Crohn's disease, Degos disease, dermatomyositis, dermatomyositis-juvenile, discoid lupus, essential mixed cryoglobulinemia, fibromyalgia-fibromyositis, Graves disease, Guillain-Barré, Hashimoto thyroiditis, idiopathic pulmonary fibrosis, idiopathic thrombocytopenia purpura (ITP), IgA nephropathy, insulin-dependent diabetes, juvenile arthritis, lichen planus, lupus, Ménière disease, mixed connective tissue disease, multiple sclerosis, myasthemia gravis, pemphigus vulgaris, pernicious anemia, polyarteritis nodosa, polychondritis, polyglandular syndromes, polymyalgia rheumatica, polymyositis and dermatomyositis, primary agammaglobulinemia, primary biliary cirrhosis, psoriasis, Raynaud phenomenon, Reiter syndrome, rheumatic fever, rheumatoid arthritis, sarcoidosis, scleroderma, Sjögren syndrome, stiff-person syndrome, Takayasu arthritis, temporal arteritis/giant cell arteritis, ulcerative colitis, vasculitis, vitiligo, Wegener granulomatosis and the like (See the American Autoimmune Related Diseases Association, Inc. website: aarda.org).

In certain exemplary embodiments, the nature and characteristics of symptoms, conditions and diseases and/or disorder phenotypes are reduced by the methods of the present invention compared to the nature and characteristics of symptoms, conditions and diseases and/or disorder phenotypes observed in a patient or a sample (e.g., a test sample or a sample taken from a subject prior to, during or after treatment). In certain aspects, the nature and characteristics of symptoms, conditions and diseases and/or disorder phenotypes are reduced by about 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, 99.9% or more, or any range(s) in between.

In certain exemplary embodiments, a method for ameliorating, preventing and/or treating diseases, symptoms and/or disorders as described herein includes the step of administering a therapeutically effective amount of an agent (e.g., one or more PD-L (e.g., PD-L1 and/or PD-L2) polypeptides, one or more nucleic acid sequences encoding one or more PD-L (e.g., PD-L1 and/or PD-L2) polypeptides, one or more PD-L (e.g., PD-L1 and/or PD-L2) agonists, or one or more test compounds, or pharmaceutically acceptable salts thereof) to a subject. As defined herein, a therapeutically effective amount of agent (i.e., an effective dosage) ranges from about 0.0001 to 30 mg/kg body weight, from about 0.001 to 25 mg/kg body weight, from about 0.01 to 20 mg/kg body weight, from about 0.1 to 15 mg/kg body weight, or from about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of one or more iTregs, one or more PD-L (e.g., PD-L1 and/or PD-L2) polypeptides, one or more nucleic acid sequences encoding one or more PD-L (e.g., PD-L1 and/or PD-L2) polypeptides, one or more PD-L (e.g., PD-L1 and/or PD-L2) agonists, or one or more test compounds, or pharmaceutically acceptable salts thereof can include a single treatment or, in certain exemplary embodiments, can include a series of treatments. It will also be appreciated that the effective dosage of agent used for treatment may increase or decrease over the course of a particular treatment. Changes in dosage may result from the results of diagnostic assays as described herein. The pharmaceutical compositions can be included in a container, pack, or dispenser together with instructions for administration.

It is to be understood that the embodiments of the present invention which have been described are merely illustrative of some of the applications of the principles of the present invention. Numerous modifications may be made by those skilled in the art based upon the teachings presented herein without departing from the true spirit and scope of the invention. Method steps of embodiments described herein need not be performed in the order recited. The contents of all references, patents and published patent applications cited throughout this application are hereby incorporated by reference in their entirety for all purposes.

The following examples are set forth as being representative of the present invention. These examples are not to be construed as limiting the scope of the invention as these and other equivalent embodiments will be apparent in view of the present disclosure, Figures and accompanying claims. According to embodiments of the present invention and as supported by the experiments to follow, PD-L (e.g., PD-L1 and/or PD-L2) mediates T cell tolerance. PD-L (e.g., PD-L1 and/or PD-L2) is used to inhibit T cell responses by limiting the activation of self-reactive T cells, by attenuating the function of self-reactive effector T cells, and/or by promoting iTreg development and function. According to additional embodiments, PD-L (e.g., PD-L1 and/or PD-L2) is used to control the dynamic balance between effector and regulatory T cells in vivo. For example, PD-L (e.g., PD-L1 and/or PD-L2) controls Treg development in lymphoid organs, important for immune homeostasis; 2) PD-L (e.g., PD-L1 and/or PD-L2) promotes Treg development at target tissues, protecting against immune-mediated tissue damage; and 3) PD-L (e.g., PD-L1 and/or PD-L2) sustains and enhances Treg function within an inflammatory microenvironment, effectively counterbalancing the pathogenic effector T cells.

According to additional embodiments, PD-L (e.g., PD-L1 and/or PD-L2) is used to induce and maintain the expression of Foxp3 in iTregs, which stabilizes and sustains Treg function.

Example I

PD-L1 Synergized with TGF-β to Promote iTreg Conversion

Since the peripheral pool of regulatory cells can consist of both thymically-derived natural Tregs and TGF-β-induced converted Tregs (iTregs), whether PD-1 ligands affect iTreg generation was assessed. Freshly isolated WT or PD-L1$^{-/-}$PD-L2$^{-/-}$ antigen presenting cells (APCs) were cultured with naïve CD4$^+$CD62L$^{hi}$Foxp3.GFP$^-$ T cells from WT Foxp3.GFP reporter mice in the presence of TGF-β and anti-CD3. WT APCs induced naïve T cell conversion into Foxp3$^+$ iTregs in the presence of TGF-β (22.1%, FIG. 1A). In contrast, when naïve T cells were cultured with PD-L1$^{-/-}$PD-L2$^{-/-}$ APCs, anti-CD3 and TGF-β, there was a profound defect in conversion to Foxp3$^+$ iTregs, with approximately a 10-fold decrease in percentage of Foxp3$^+$ iTregs (2.74% compared to 22.1%, FIG. 1A). This result indicated that PD-L1 and/or PD-L2 may regulate FoxP3$^+$ iTreg conversion. When PD-L1$^{-/-}$ APCs were cultured with naïve CD4$^+$CD62L$^{hi}$FoxP3.GFP$^-$ T cells, anti-CD3 and TGF-β, there was at least a five-fold reduction in conversion to iTreg as compared to culture with WT APCs (3.86% vs. 22.1%, respectively). Based on the above data, PD-L1 mediates iTreg conversion from naïve CD4$^+$Foxp3$^-$ T cells, without co-stimulatory molecules or soluble factors produced by APCs.

Figure 1B:
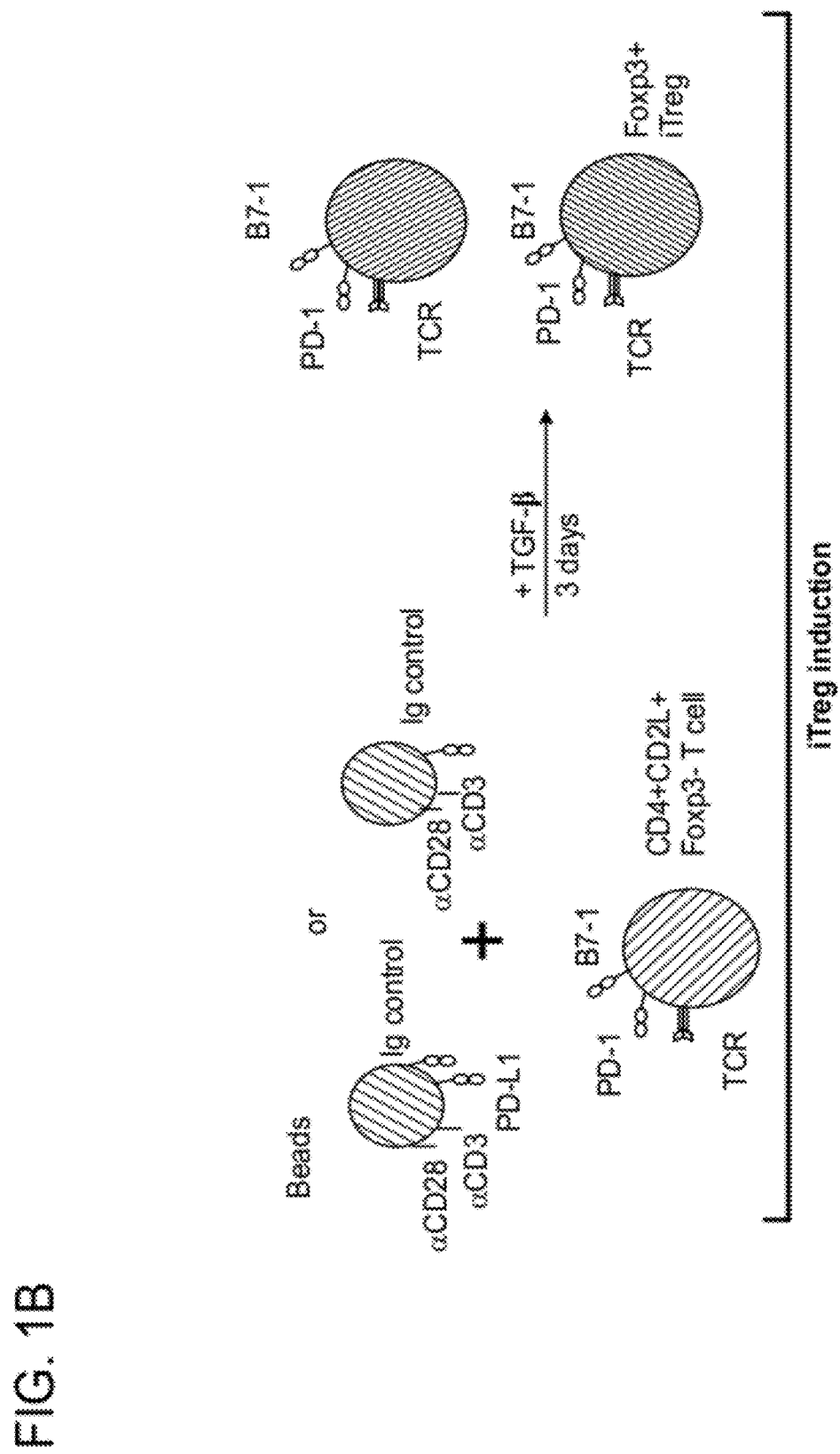
Figure 1B:
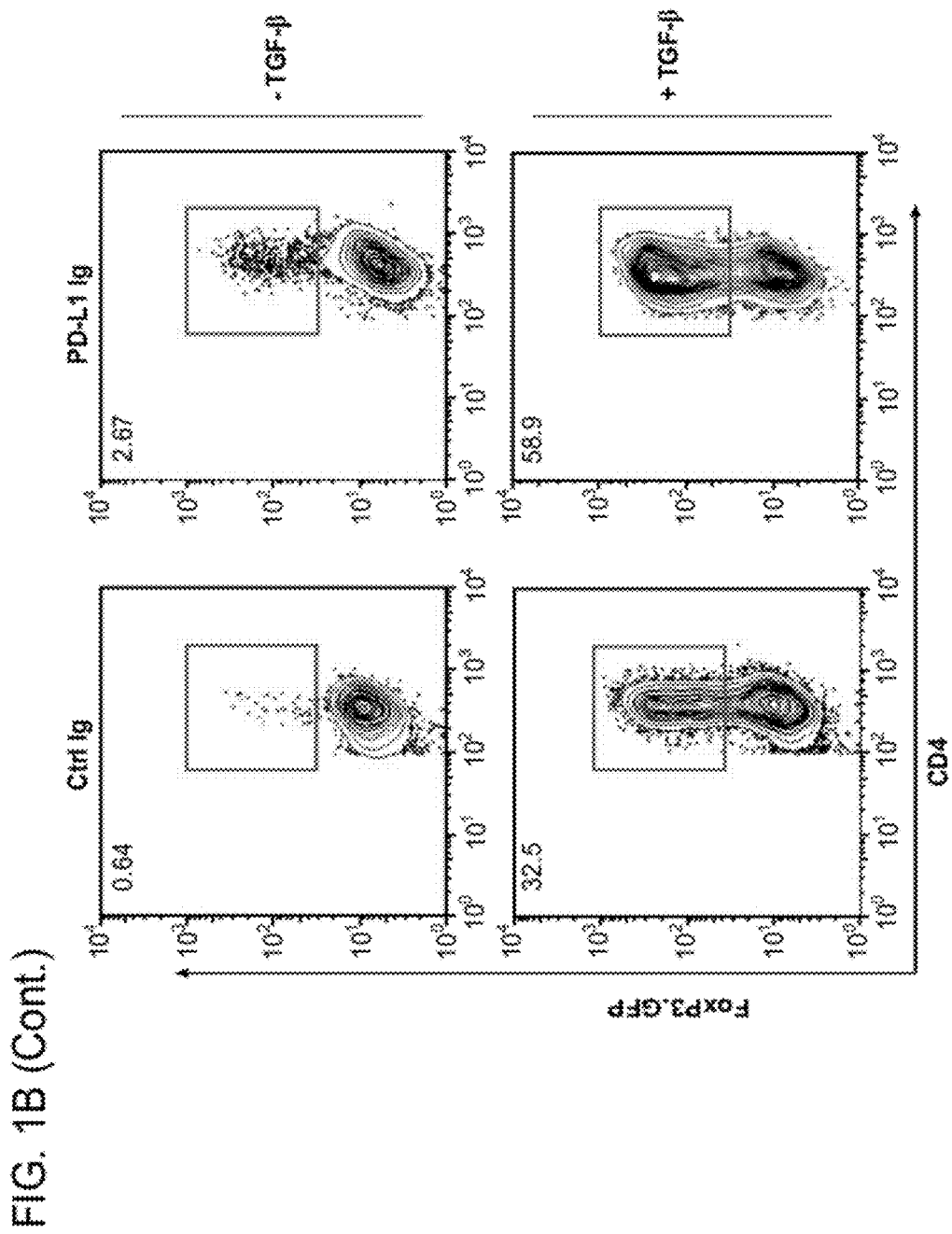

To further investigate the role of PD-L1 in iTreg development and to reduce confounding factors (e.g., surface molecules or soluble factors) that might be differentially expressed by PD-L1$^{-/-}$, PD-L2$^{-/-}$, and PD-L1$^{-/-}$PD-L2$^{-/-}$ APCs, epoxy beads to which anti-CD3, anti-CD28 and PD-L1-Ig or control-Ig were attached were used as artificial APCs (henceforth referred to as PD-L1-Ig beads or control-Ig beads). Naïve CD4$^+$CD62L$^{hi}$Foxp3$^-$ T cells were cultured with TGF-β plus PD-L1-Ig beads or control-Ig beads. Co-culture of PD-L1-Ig beads, but not control-Ig beads, with naïve CD4$^+$FoxP3$^-$ T cells significantly enhanced iTreg development in the presence of TGF-β (58.9% vs. 32.5%, FIG. 1B). TGF-β has been shown to be necessary for iTreg generation (Chen et al. (2003) *J. Exp. Med.* 198:1875; Fantini et al. (2004) *Immunol.* 172:5149; Marie et al. (2005) *J. Exp. Med.* 201:1061; Pyzik et al. (2007) *J. Leukoc. Biol.* 82:335). Whether PD-L1 could solely drive iTreg development and override the need for TGF-β was queried. Naïve T cells were cultured with PD-L1-Ig beads or control-Ig beads in the absence of exogenous TGF-β. PD-L1 beads alone could induce the conversion of naïve T cells to Foxp3$^+$ iTregs (2.67% vs. 0.64% for control-Ig bead). Accordingly, iTreg development was observed in the absence of exogenous TGF-β. That iTreg development was observed in the absence of exogenous TGF-3 when PD-L1 was present demonstrates that PD-L1 signaling is a pathway for inducing adaptive Treg development.

Figure 1C:
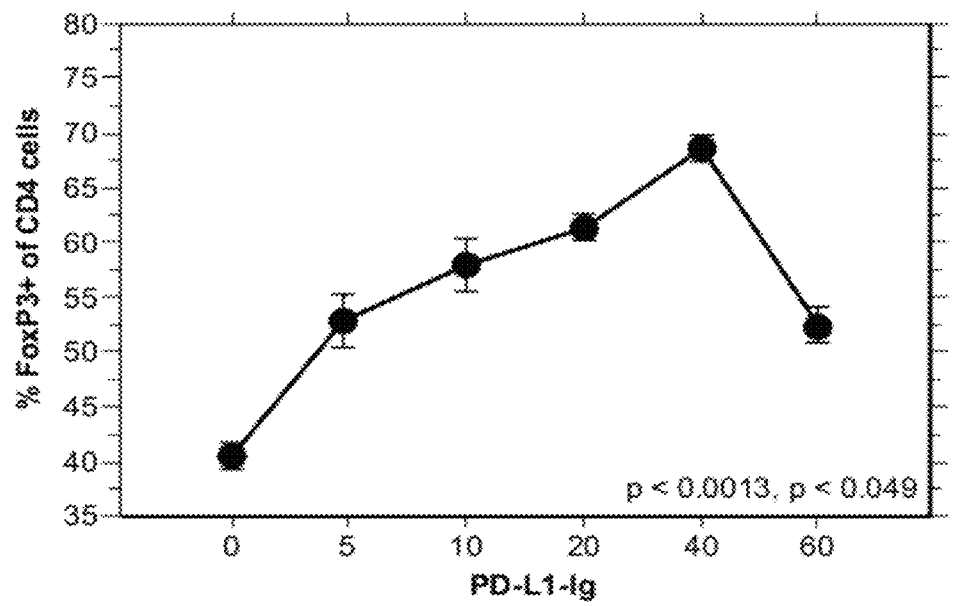
Figure 1D:
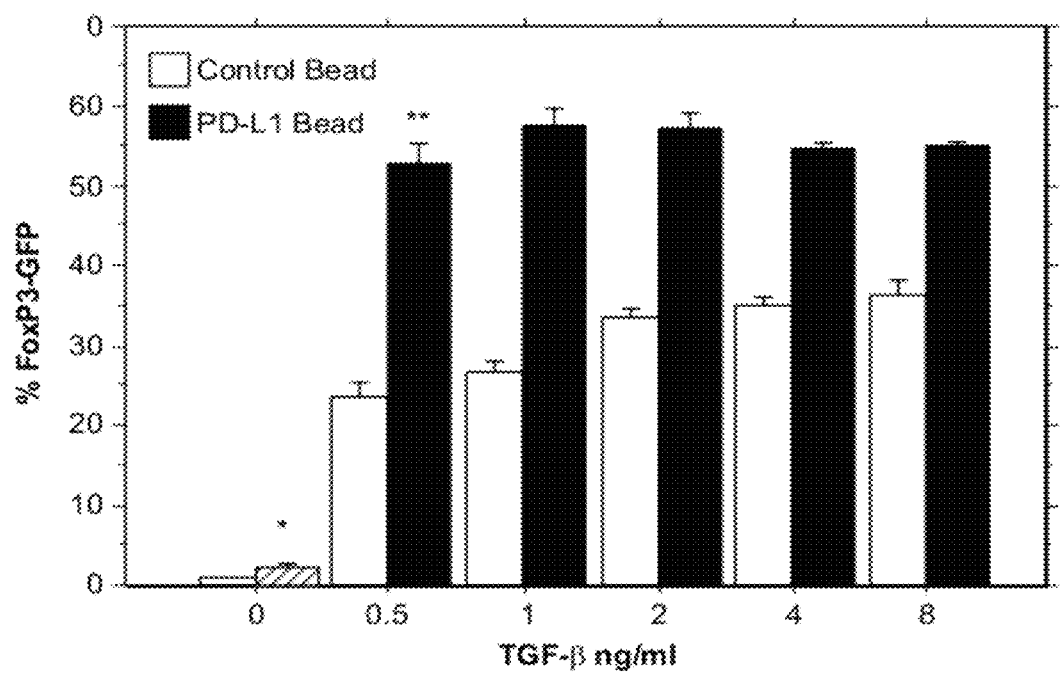

To further determine the contribution of PD-L1 to iTreg development, the amount of PD-L1-Ig on the surface of the beads was titered and it was determined that there was a quantitative relationship between the amount of PD-L1 and number of induced FoxP3$^+$ CD4 T cells: greater numbers of Foxp3$^+$ CD4 T cells could be induced with increasing amounts of PD-L1 (FIG. 1C). Moreover, even with increasing amounts of TGF-β, iTreg development could not be augmented with control-Ig beads to the extent observed with PD-L1-Ig beads (FIG. 1D). Very low amounts of TGF-β were sufficient for iTreg development when naïve CD4+ T cells were cultured in the presence of PD-L1-Ig beads as compared with control-Ig beads. Thus, PD-L1 and TGF-β have synergistic roles in regulating Foxp3+ iTreg development.

Figure 1E:
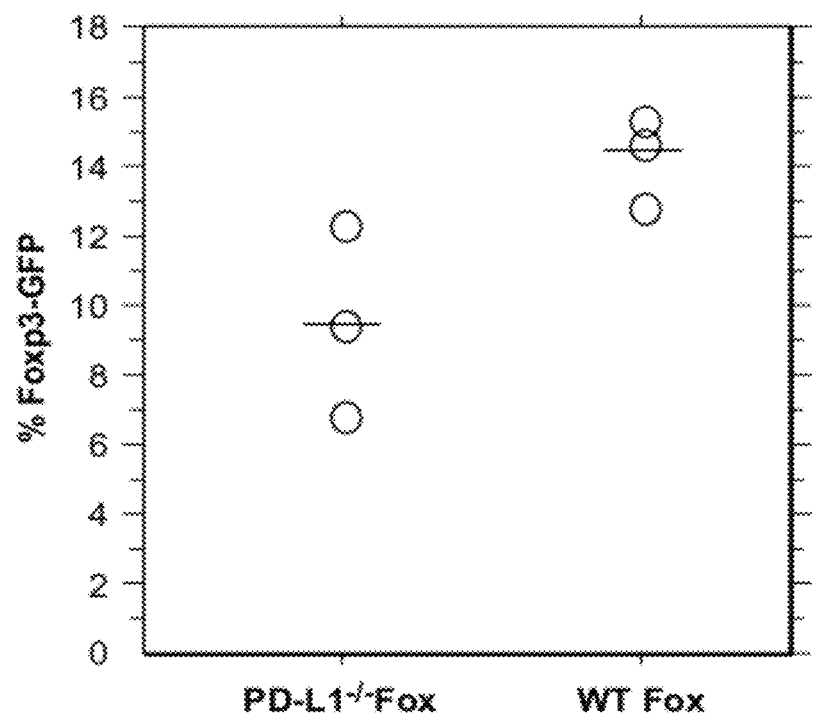
FIG. 1E depicts that peripheral Treg compartment is affected by PD-L1 deficiency. Spleens of $PD-L1^{-/-}$ Foxp3.GFP mice or WT Foxp3.GFP reporter mice were analyzed for Foxp3.GFP expression by flow cytometry. % $Foxp3^+$ of gated $CD4^+$ T cells are shown.

To investigate whether PD-L1 influenced the development of regulatory T cells, natural Treg development was compared in WT and PD-L1$^{-/-}$Foxp3.GFP mice. As shown in FIG. 1E, PD-L1$^{-/-}$Foxp3.GFP mice had a modest decrease in naturally occurring Foxp3+ cells as compared to WT Foxp3.GFP mice.

Example II

PD-L1-Induced CD4+Foxp3+ Tregs Suppressed CD4+ Effector T Cells

Figure 2A:
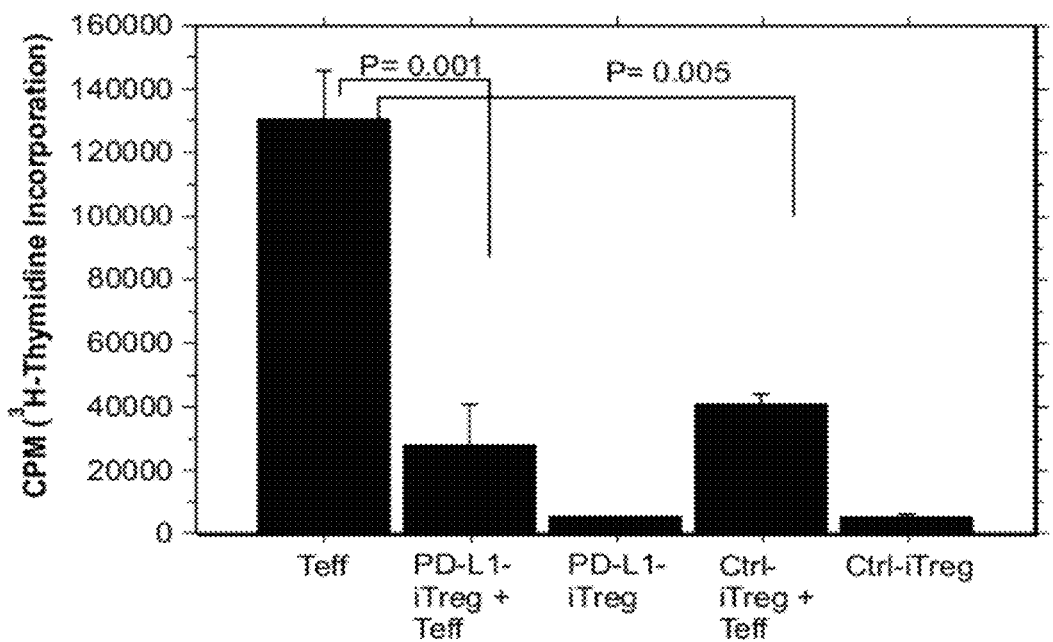
FIGS. 2A-2C depict that PD-L1-induced $CD4^+$ $Foxp3^+$ Regulatory T cells suppressed CD4+ T effector cells in vitro. (A) PD-L1-induced Treg function was assessed by 3H-thymidine incorporation of naïve $CD4^+CD25^-$ T effectors following three days of co-culture at a 1:1 Treg to Teff ratio plus PD-L1-beads (5:1 bead to T effector cell ratio). Data represent the mean±s.d. and are representative of at least two independent experiments. (B) PD-L1-induced Treg function was assessed by carboxyfluorescein diacetate succinimidyl ester (CFSE) dilution of naïve $CD4^+CD25-$ T effectors following three days of incubation with 1:1 Treg to Teff ratio and PD-L1-beads (5:1 bead to T effector cell ratio). Data represent the mean±s.d. and are representative of at least two-independent experiments. (C) Quantification of Teff proliferation in (B), determining the division index of gated $CD4^+CD45.1^+$ (the number of divisions a single cell has divided) as analyzed by FlowJo software. Data represent the mean±s.d.
Figure 2C:
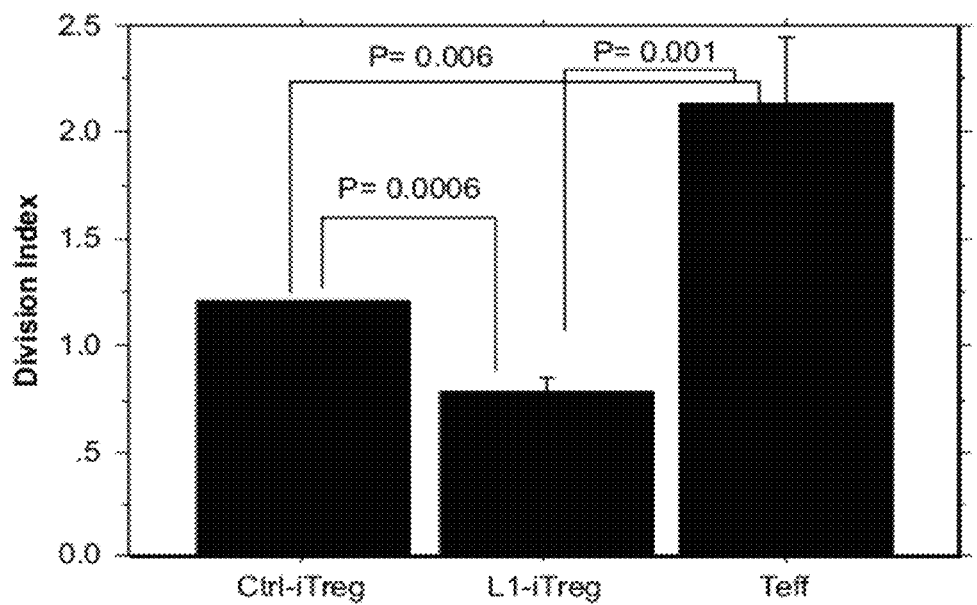
Figure 2B:
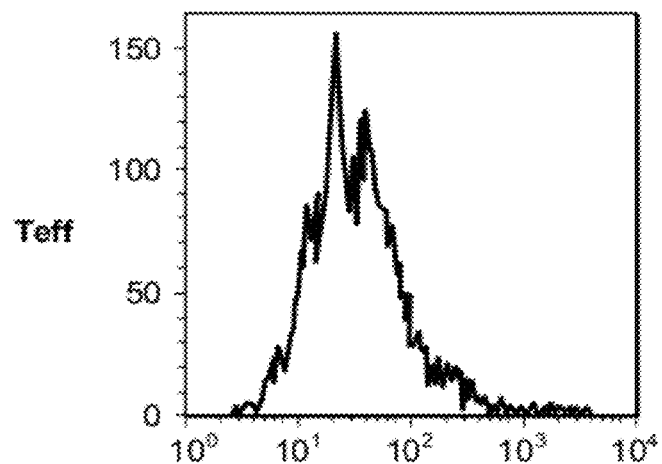
Figure 2B:
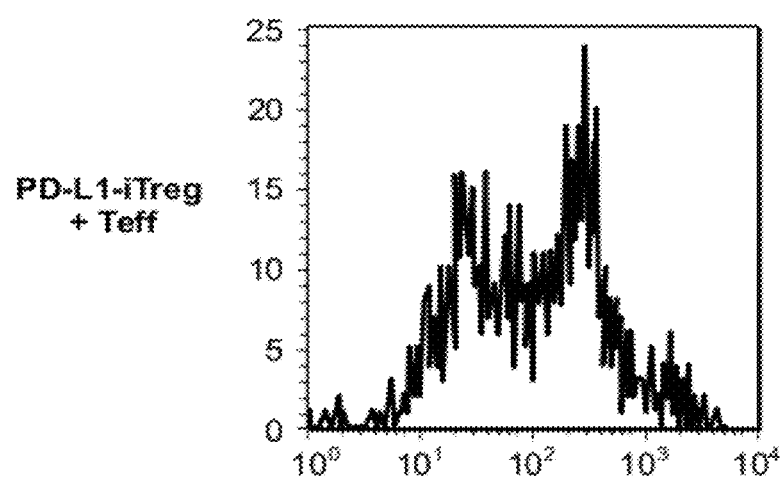
Figure 2B:
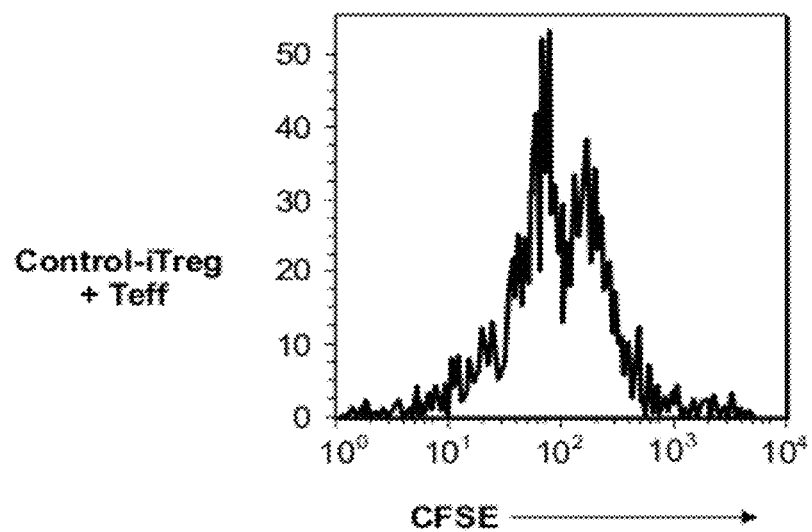

To assess whether PD-L1-induced iTregs not only express Foxp3, but also functioned as suppressor T cells, naïve T cells were induced with TGF-β plus control-Ig or PD-L1-Ig beads, and Foxp3+ iTregs differentiated from the naïve T cells were sorted following three days of culture. Sorted CD4+CD25− T cells were used as Teffs. The Teffs were mixed with iTregs at a 1:1 ratio and cultured with bead-bound anti-CD3/anti-CD28 plus PD-L1-Ig for three days. Both PD-L1-iTregs and control-iTregs could suppress the proliferation of WT Teffs similarly as measured by $^3$H-Thymidine incorporation (FIG. 2A) (Tang et al. (2008) *Nat Immunol* 9:239). To assess whether PD-L1-iTregs or control-iTregs affected the suppression of T effector cell proliferation on a per cell basis, a suppression assay was performed to measure carboxyfluorescein diacetate succinimidyl ester (CFSE) dilution of T effector cells. Either CD45.1− PD-L1iTregs or control-iTreg were cultured with CD45.1+ T effectors plus bead-bound anti-CD3/antiCD28 and PD-L1-Ig for three days. CD45.1+ T effectors were then analyzed by flow cytometry (FIG. 2B). PD-L1-iTregs reduced the Teff cell expansion at the single cell level to a greater extent compared to control-iTregs (1.5 fold greater, P=0.006), as measured by the division index (described further below) (FIG. 2C). Based on the above, PD-L1 induced the development of functional Foxp3+ regulatory T cells.

Example III

Figure 3A:
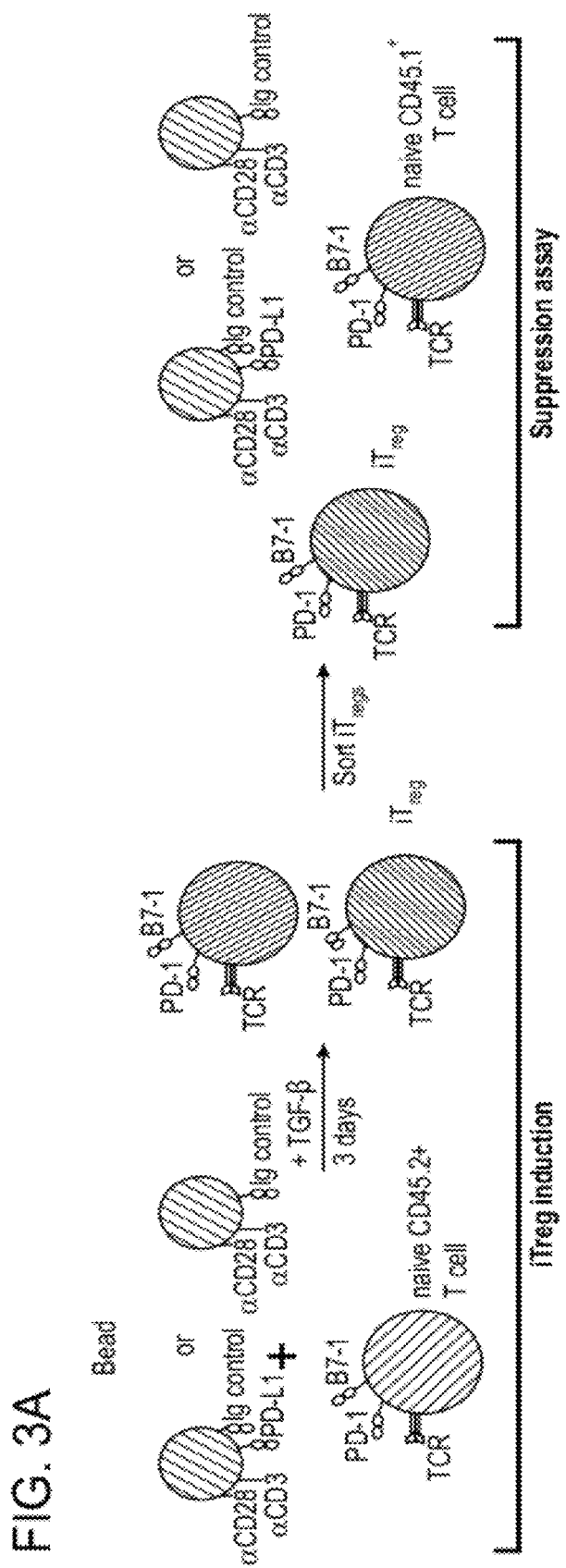
FIGS. 3A-3C depict that PD-L1 maintains Foxp3 expression by iTregs during suppression of effector cell function. (A) Schematic depiction of experiment. Naïve $CD4^+CD62L^{hi}Foxp3.GFP^-$ T cells were induced towards Treg differentiation for three days in the presence of TGF-β and IL-2 and either control- or PD-L1-beads. $Foxp3.GFP^+ CD45.1^-$ cells were then sorted and co-cultured with sorted $CD4^+CD25^- CD45.1^+$ in the presence of either control- or PD-L1-beads during the three day suppression assay. (B) 72 hours post-co-culture, $CD4^+CD45.1^-$ cells were gated and analyzed for GFP expression. Representative data of at least two independent experiments. (C) Quantification of experiment depicted in (B). Data represent the mean±s.d. and are representative of at least two independent experiments.
Figure 3B:
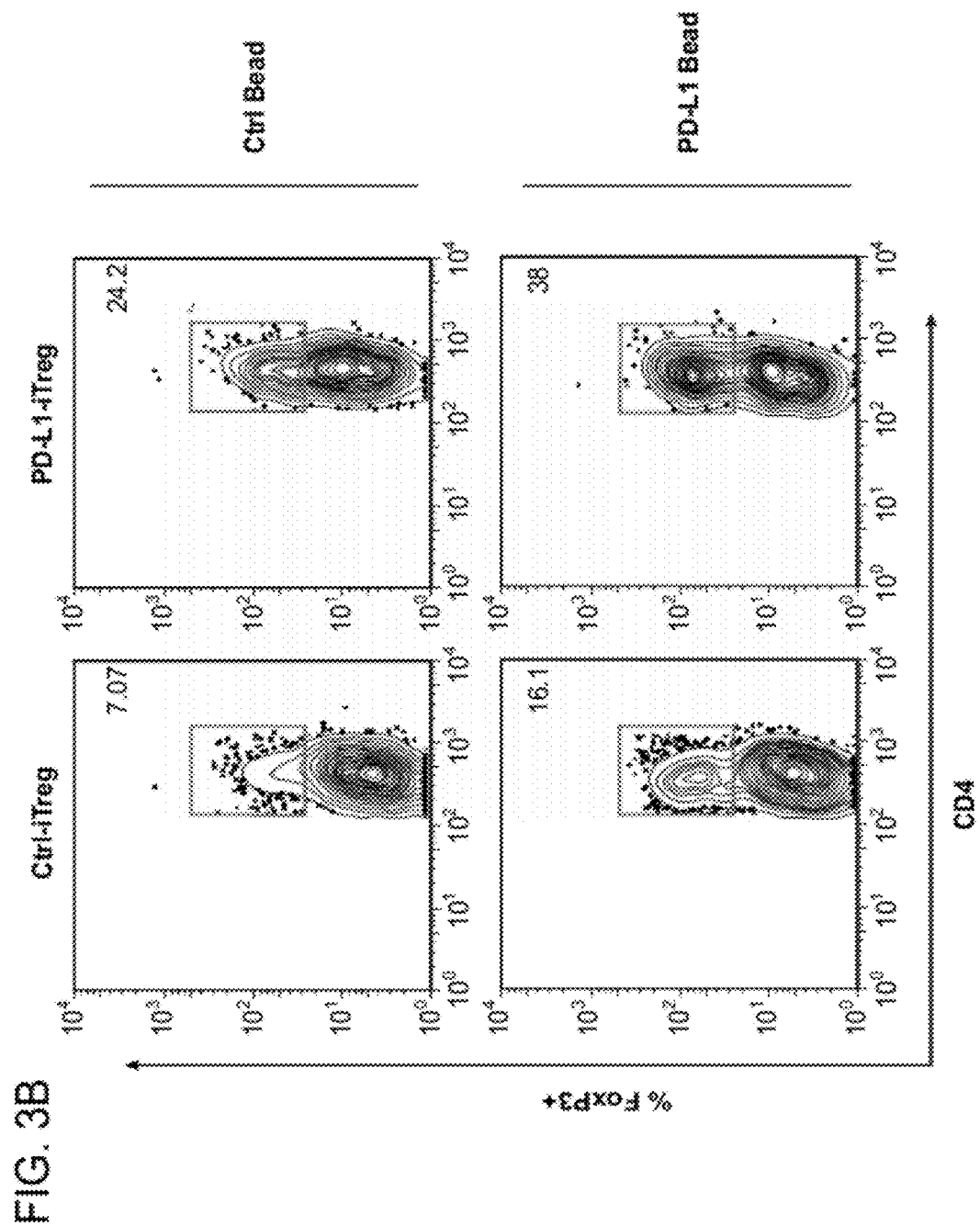
Figure 3C:
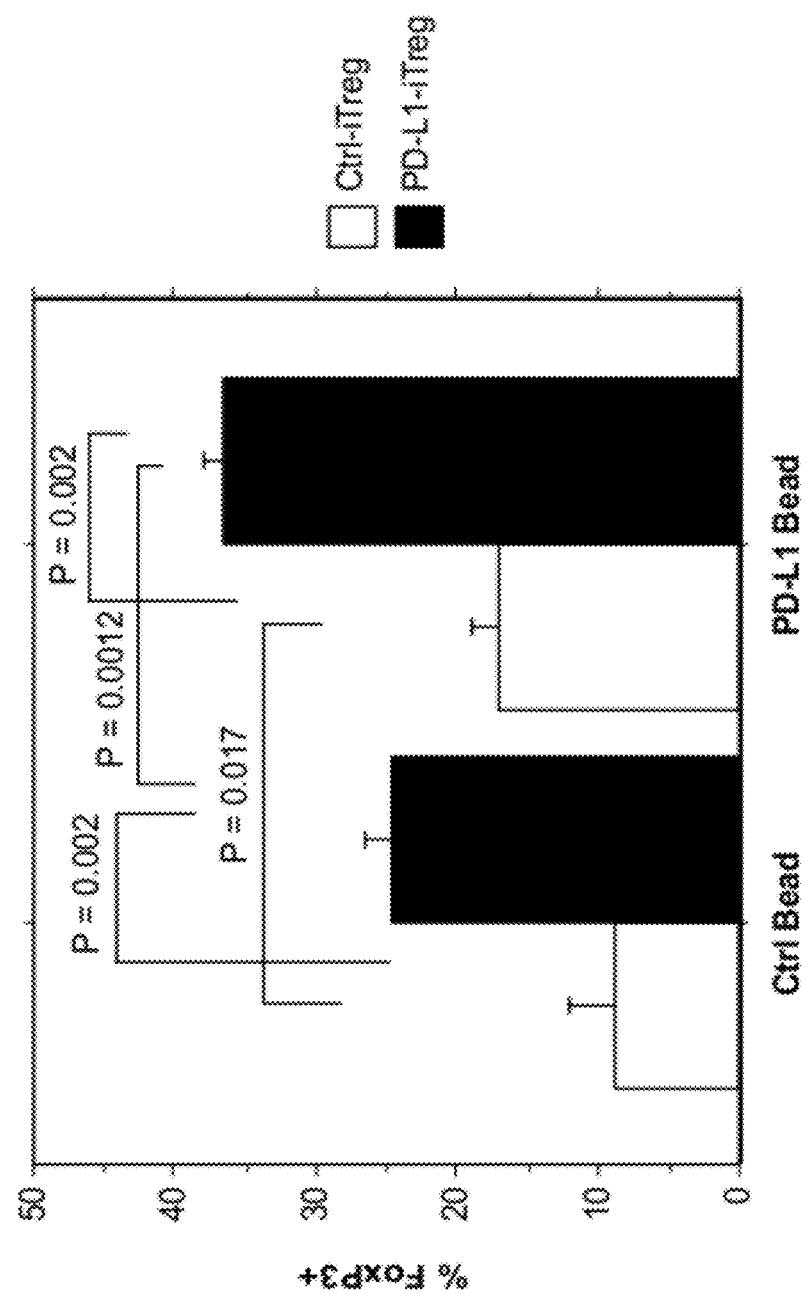

PD-L1 Improved and Maintained Foxp3 Expression on iTreg and Augmented Suppression at Low Treg:Teff Ratios Continued Foxp3 expression is necessary for maintenance of Treg function (Williams et al. (2007) *Nat. Immunol.* 8:277; Kim et al. (2007) *Nat. Immunol.* 8:191). Whether PD-L1 influences the maintenance of the iTreg population was queried. Treg development was induced by culturing naïve CD45.1− T cells with either PD-L1-Ig beads or control-Ig beads plus TGF-β for three days. Sorted Foxp3+ PD-L1-iTregs or Foxp3+ control-iTregs were co-cultured with CD4+CD25−CD45.1+ T effectors, stimulated with either PD-L1-Ig bead or control-Ig bead for three days, and analyzed for Foxp3.GFP expression by flow cytometry (FIG. 3A). Foxp3 was better maintained in iTregs originally induced with PD-L1-Ig beads as compared to control-Ig beads (24.2% positive vs. 7.07% positive, FIG. 3B, top). In addition, PD-L1-Ig significantly affected the percentage of cells maintaining Foxp3 expression (16.1% for control-iTregs vs. 38% for PD-L1-iTregs, FIG. 3B, bottom). Interestingly, iTregs that were both induced and re-stimulated in the presence of PD-L1-Ig maintained the greatest percentage of Foxp3 expressing cells (38%, FIGS. 3B and 3C). Based on the above, PD-L1 maintained Foxp3 expression by induced-Tregs.

Figure 4B:
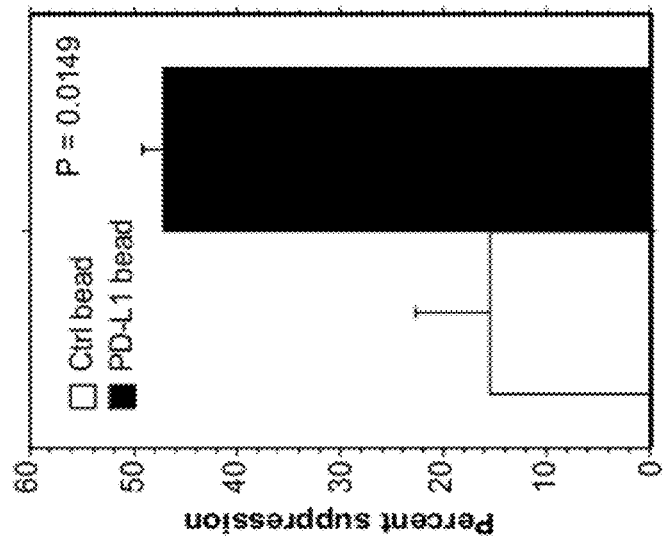
FIGS. 4A-4B depict that PD-L1 enhances the efficiency of iTreg mediated suppression of Teffs. (A) $Foxp3.GFP^+$-induced Tregs were sorted and co-cultured with naïve $CD4^+ CD25^-CD45.1^+$ T effector cells plus either PD-L1-Ig bead or control-Ig bead (at various Treg:Teff ratios). 72 hours later, cultures were pulsed with 3H-thymidine for 12-14 hours. P<0.0009 at 1:4 ratio cultured with PD-L1 beads (comparing Teff+iTreg vs. Teff). (B) Quantification of suppression at 1:4 ratio of Treg:Teff. P=0.0149. Data represent the mean±s.d. and are representative of at least two independent experiments.
Figure 4A:
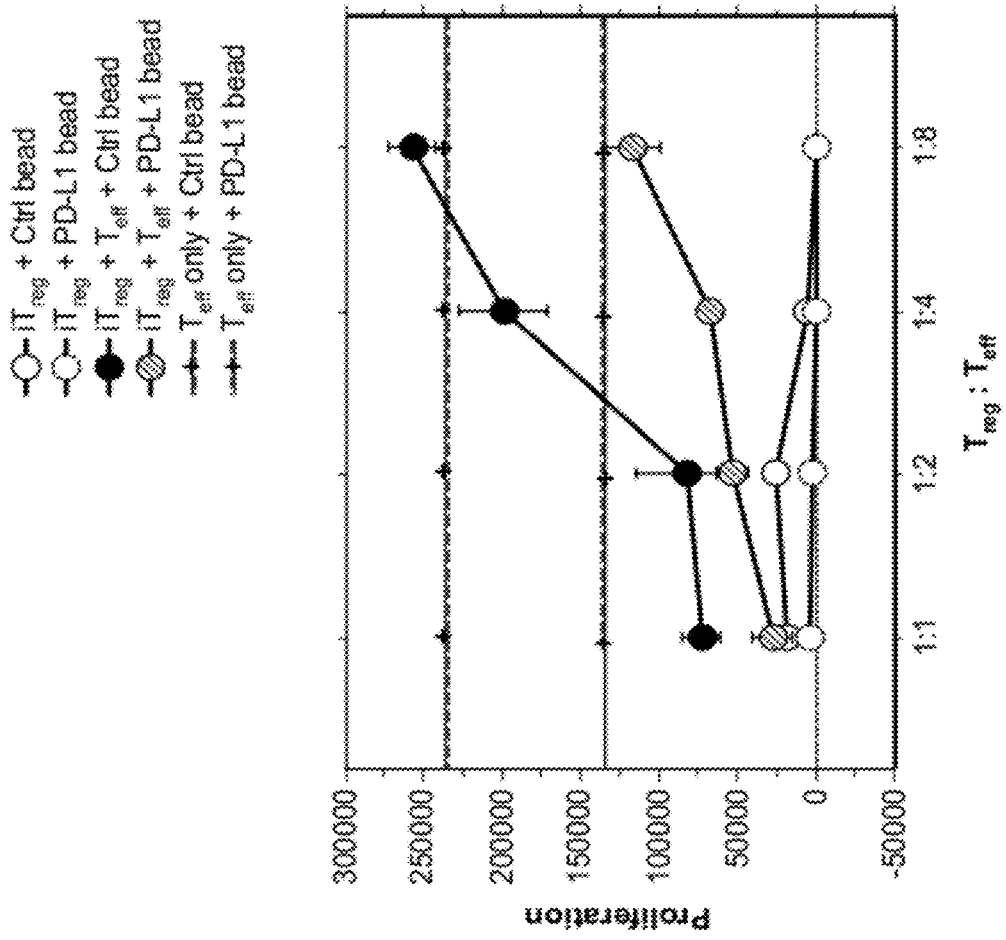

Whether the presence of PD-L1 could influence the efficiency of suppression of iTregs was then tested. A suppression assay was performed at a variety of iTreg:Teff ratios as described above and graphically depicted in FIG. 3A, far right. It was determined that PD-L1-Ig enhanced iTreg suppressive function at a low Treg:Teff ratio, 1:4 (46% suppression using PD-L1 bead vs. 3% suppression using control bead, P=0.001, FIGS. 4A and 4B). The effect was less prominent when Tregs were more numerous, but still showed improved suppressive capacity (FIG. 4A). Taken together, these results demonstrated that PD-L1 enhanced the efficiency of the suppressive function of iTregs.

Example IV

Figure 5A:
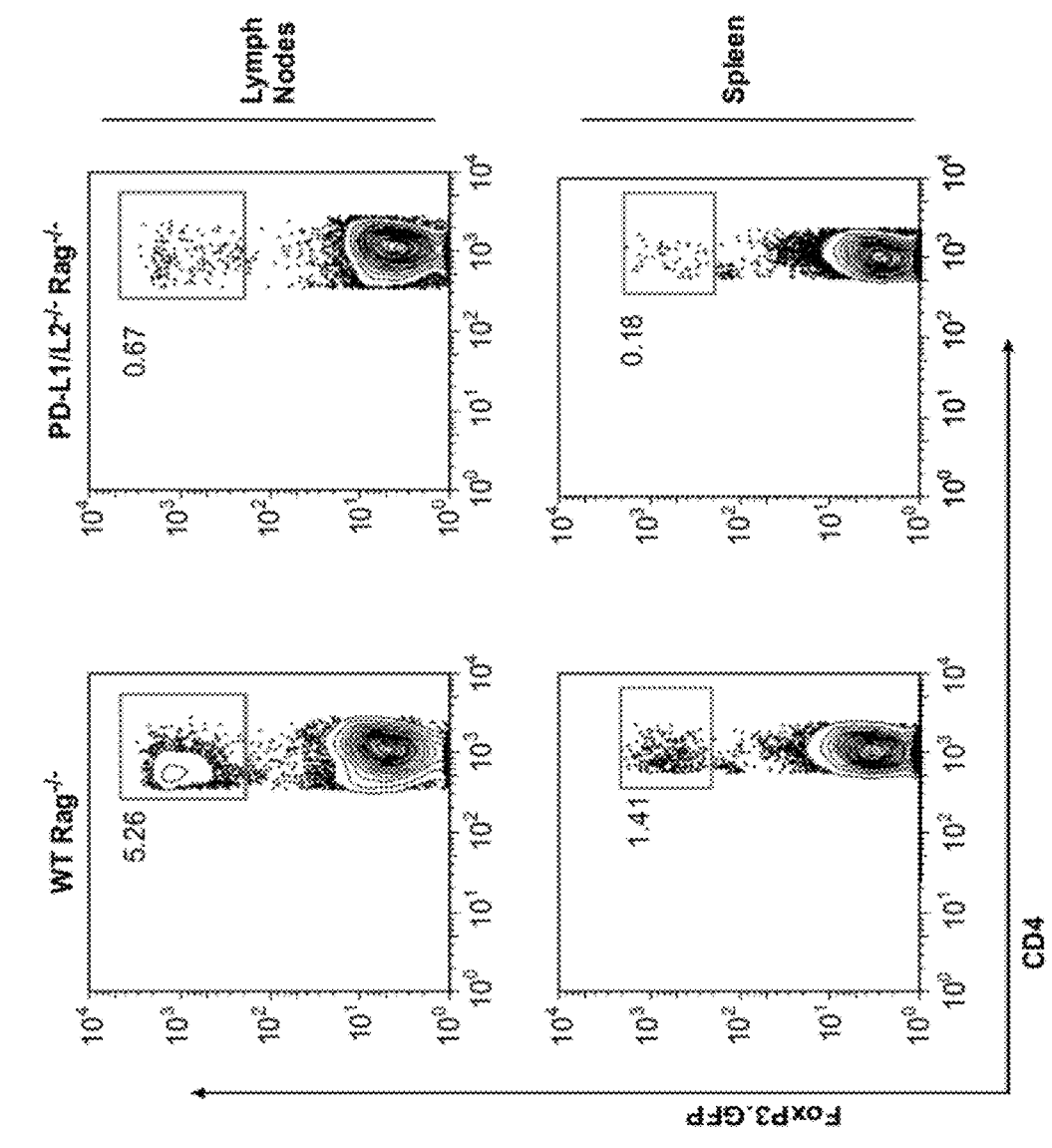
FIGS. 5A-5E depict attenuated iTreg development in the absence of PD-L1:PD-1 pathway in vivo. (A) $CD4^+ CD62L^{hi}Foxp3.GFP^-$ cells were adoptively transferred intravenously (i.v.) into the tail veins of WT $Rag^{-/-}$ or $PD-L1^{-/-}PD-L2^{-/-}Rag^{-/-}$ mice. Spleens and lymph nodes were analyzed for Foxp3.GFP expression 14-17 days post-transfer. (B) Quantitation of Foxp3.GFP expression from independent mice depicted in (A). (C) Analysis of $IL-17^+$ and $IFN-\gamma^+$ Teff cells by intracellular cytokine staining and (D) ratios of IL-17 producing-Teff:Treg and IFN-γ-producing Teff:Treg from WT $Rag^{-/-}$ or $PD-L1^{-/-}PD-L2^{-/-}Rag^{-/-}$ mice at 14-17 days post-transfer. (E) IL-2 production by CD4+ cells, measured by intracellular cytokine staining. P=0.19, lymph nodes; P=0.25, spleen. Data represent the mean±s.d. and are representative of two independent experiments.
Figure 5B:
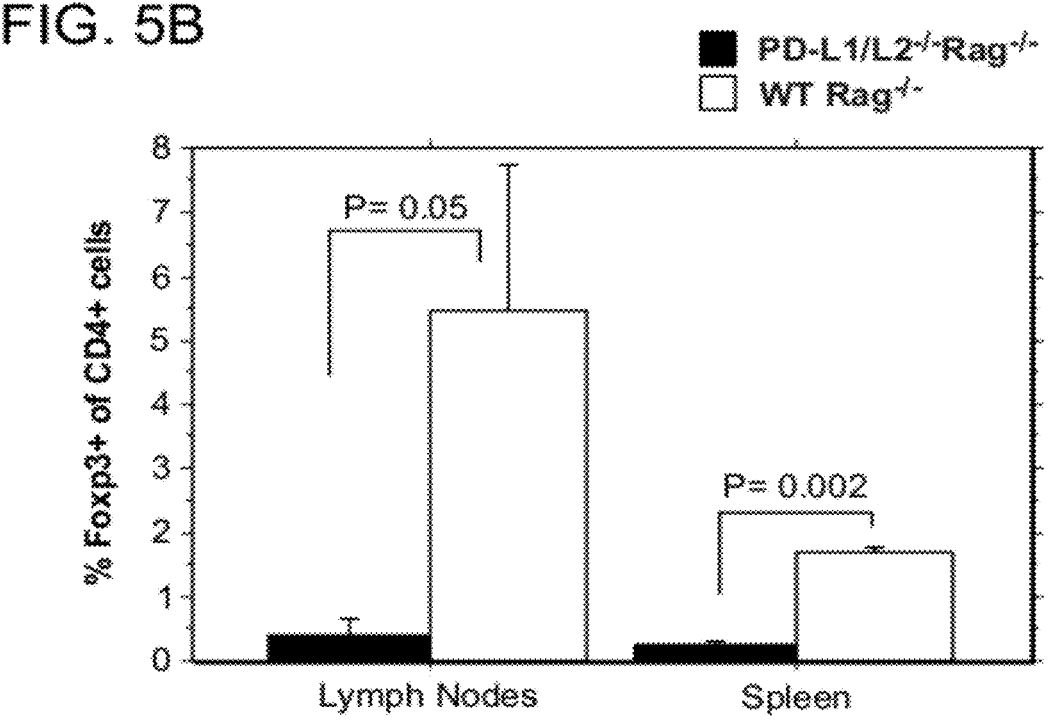
Figure 5E:
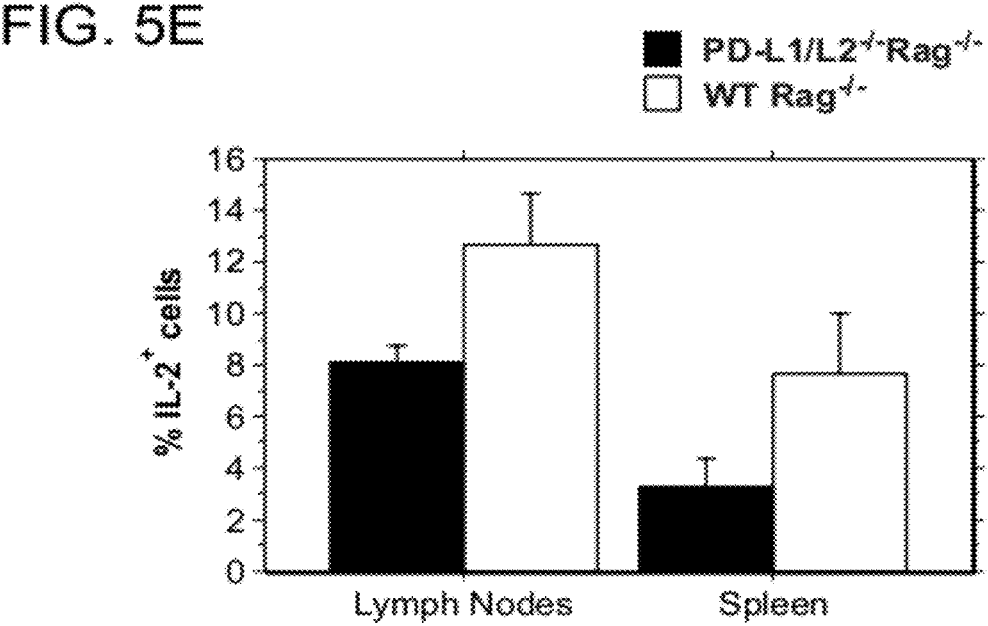
Figure 5C:
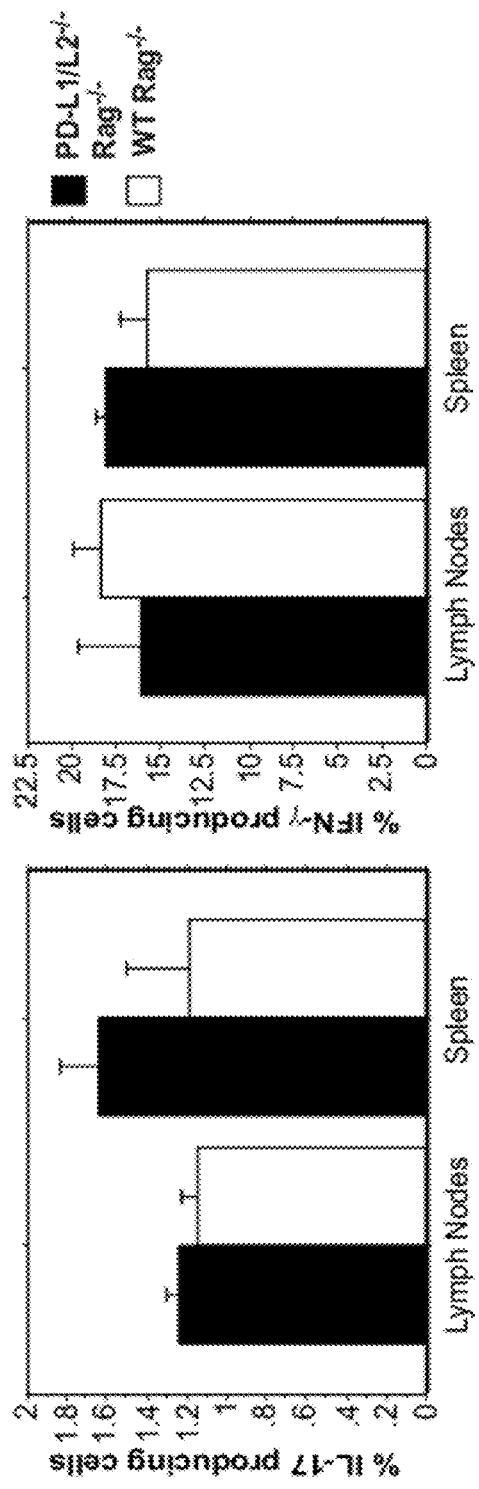
Figure 5D:
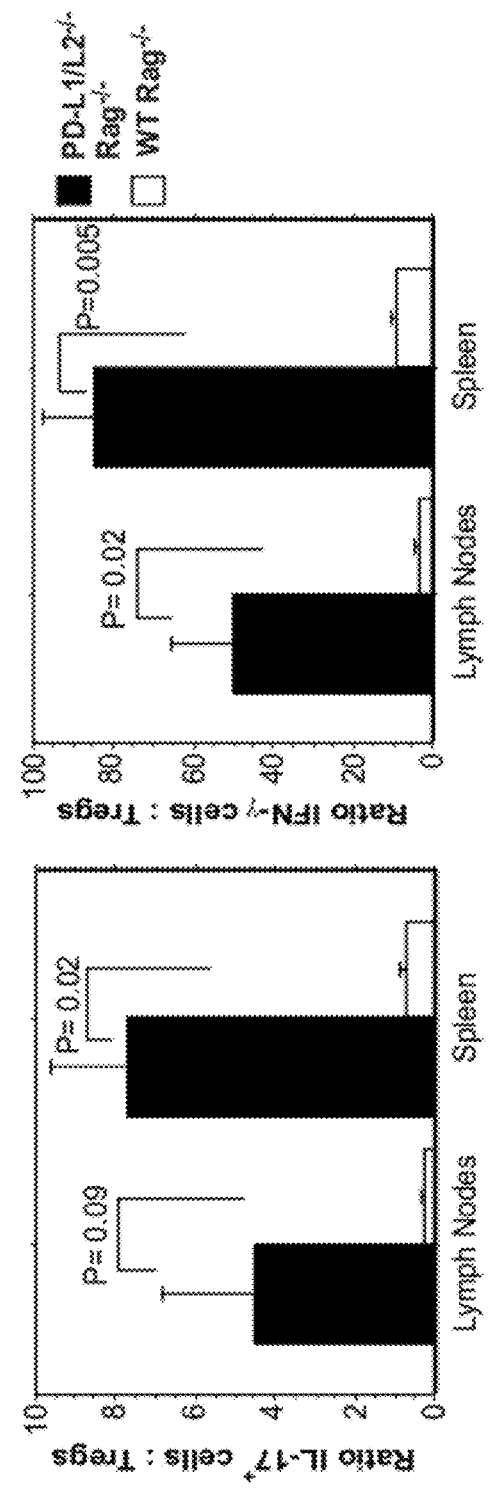

PD-L1 Deficiency Lead to Impaired Treg Conversion In Vivo iTregs can develop spontaneously from naïve T cells in a lymphopenic environment (Bloom et al. (2008) *Am. J. Transplant.* 8:793; Calzascia et al. (2008) *Proc. Natl. Acad. Sci. USA* 105:2999; Winstead et al. (2008) *J. Immunol.* 180:7305). To assess the role of PD-L for induced Treg development in vivo, naïve CD4+CD62L$^{hi}$Foxp3.GFP− T cells were adoptively transferred into PD-L1$^{-/-}$PD-L2$^{-/-}$Rag$^{-/-}$ or WT Rag$^{-/-}$ mice. The CD4+ T cells were then analyzed for Foxp3 expression at day 14-17 post-adoptive transfer by flow cytometry. There were approximately 10-fold fewer Foxp3.GFP+ cells observed in PD-L1$^{-/-}$PD-L2$^{-/-}$Rag$^{-/-}$ recipients compared to WT Rag$^{-/-}$ recipients (FIGS. 5A and 5B). The data demonstrate the use of PD-L in regulating the induction and/or maintenance of Foxp3+ Treg in vivo. Next, the Foxp3-CD4+ effector T cell responses were compared in PD-L1$^{-/-}$PD-L2$^{-/-}$Rag$^{-/-}$ and WT Rag$^{-/-}$ recipients. Cytokine production by Foxp3−CD4+ cells was measured 14-17 days following naïve T cell transfer. It was determined that naïve T cells transferred into PD-L1$^{-/-}$PD-L2$^{-/-}$Rag$^{-/-}$ and WT Rag$^{-/-}$ recipients comparably generated IL-17 and IFN-producing cells (FIG. 5C). IL-17 and IFN-γ− producing Teffs in PD-L1$^{-/-}$PD-L2$^{-/-}$Rag$^{-/-}$ recipients highly outnumbered the induced Tregs, largely because of the deficiency of iTregs generated in PD-L1$^{-/-}$PD-L2$^{-/-}$Rag$^{-/-}$ recipients (FIG. 5D). IL-2 plays an important role in the survival of regulatory T cells (Sakaguchi et al. (1995) *J. Immunol.* 155:1151; Fontenot et al. (2005) *Nat. Immunol.* 6:1142; Gavin et al. (2007) *Nature* 445:771; Setoguchi et al. (2005) *J. Exp. Med.* 201:723). A trend of increased IL-2 production by Teff cells was observed in WT Rag$^{-/-}$ recipients compared to PD-L1$^{-/-}$PD-L2$^{-/-}$Rag$^{-/-}$ mice. (FIG. 5E). Without intending to be bound by scientific theory, it is possible that IL-2 made in the presence of PD-L1 may help maintain converted Tregs. These results show a deficit of in vivo lymphopenia-induced Treg generation in the absence of PD-L1 and PD-L2, resulting in an increase of the Teff:Treg ratio in vivo. The experiments with PD-L1$^{-/-}$PD-L2$^{-/-}$Rag$^{-/-}$ recipients demonstrate that the endogenous TGF-β is not sufficient to induce and/or maintain Foxp3+ adaptive Tregs in the absence of PD-L1 and PD-L2. The loss of only the PD-L pathway diminishes the effect of TGF-β which is used for adaptive Treg identity and function. PD-L contribute unique and essential signals that drive adaptive Treg development and function.

Figure 12A:
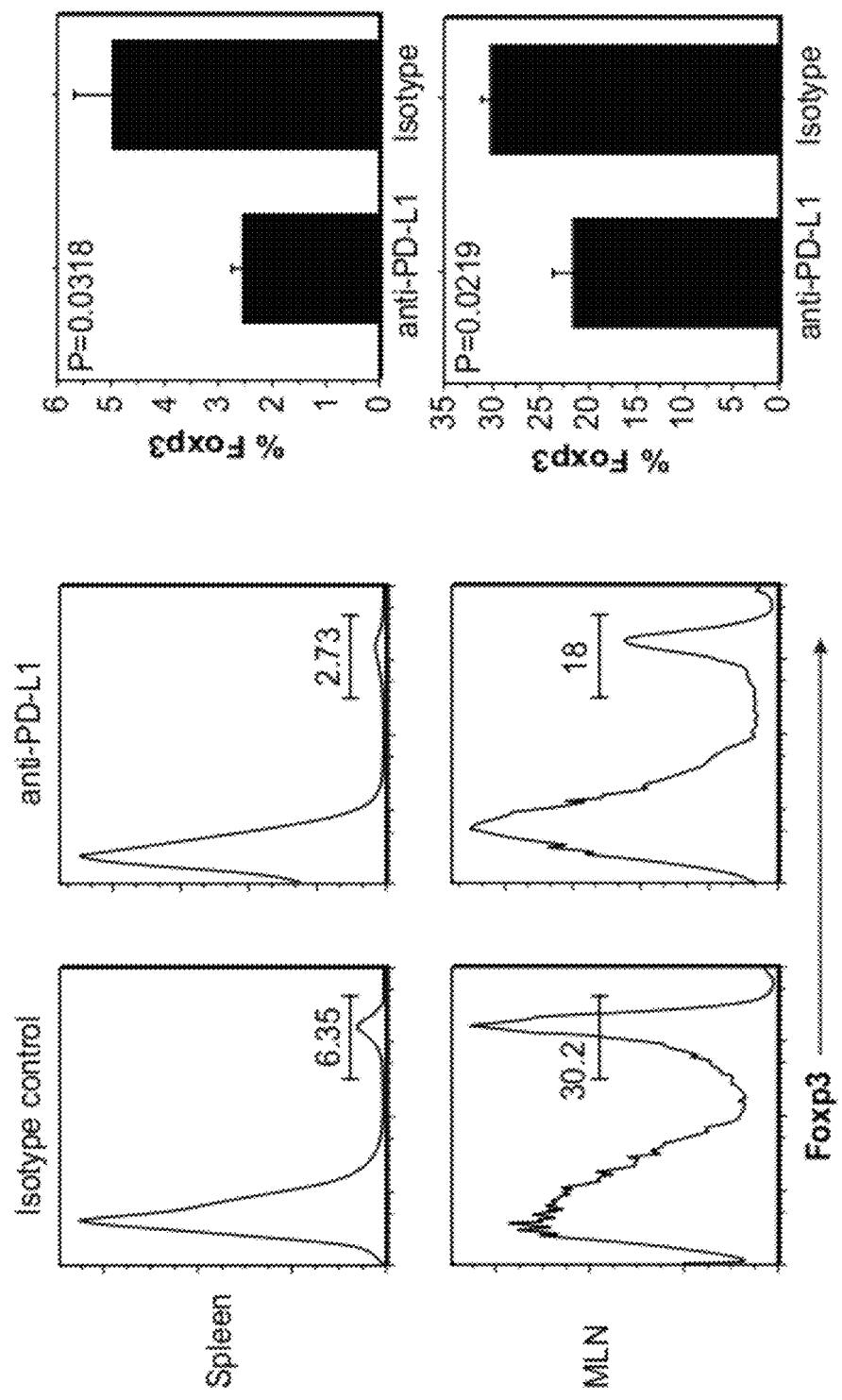
FIGS. 12A-12B depict the role of PD-L1 in Rag$^{-/-}$ mice.
Figure 12B:
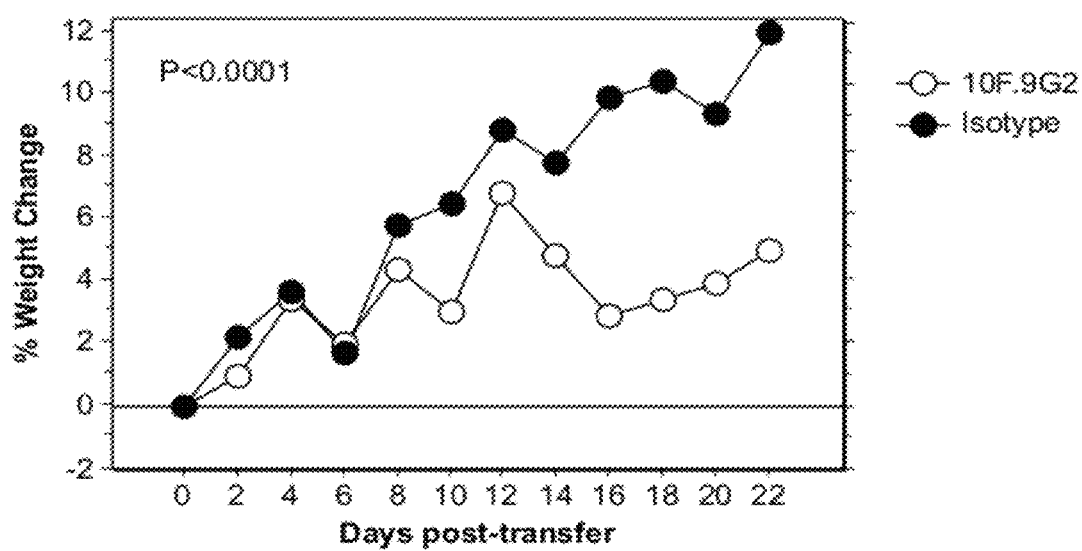

To ascertain the critical role for PD-L1 in vivo, naïve CD4 T cells were transferred to Rag$^{-/-}$ recipients treated with anti-PD-L1 blocking antibody (FIGS. 12A-12B), and the mice were monitored for 3 to 4 weeks. Mice were sacrificed to assess T reg cell development and immunopathology. A significant defect in de novo iT reg cell development was observed in Rag$^{-/-}$ mice given the anti-PD-L1 mAb compared with isotype control in both the spleen (isotype=6.35% vs. anti-PD-L1=2.73%, P=0.0318) and mesenteric lymph nodes (isotype=30.2% vs. anti-PD-L1=18%, P=0.0219. The lungs of Rag$^{-/-}$ mice treated with anti-PD-L1 mAb showed moderate to severe perivascular, peribronchial and interstitial inflammation, consisting of mononuclear cells and a few scattered neutrophils. Thus, similar to the PD-L1$^{-/-}$PD-L2$^{-/-}$Rag$^{-/-}$ recipients of naïve CD4 T cells, WT Rag$^{-/-}$ mice give anti-DP-L1 mAb exhibited defects in iT reg cell generation and developed pulmonary pathology. Collectively, these data demonstrate a key role for PD-L1 in iT reg cell development in vivo.

Example V

Figure 6A:
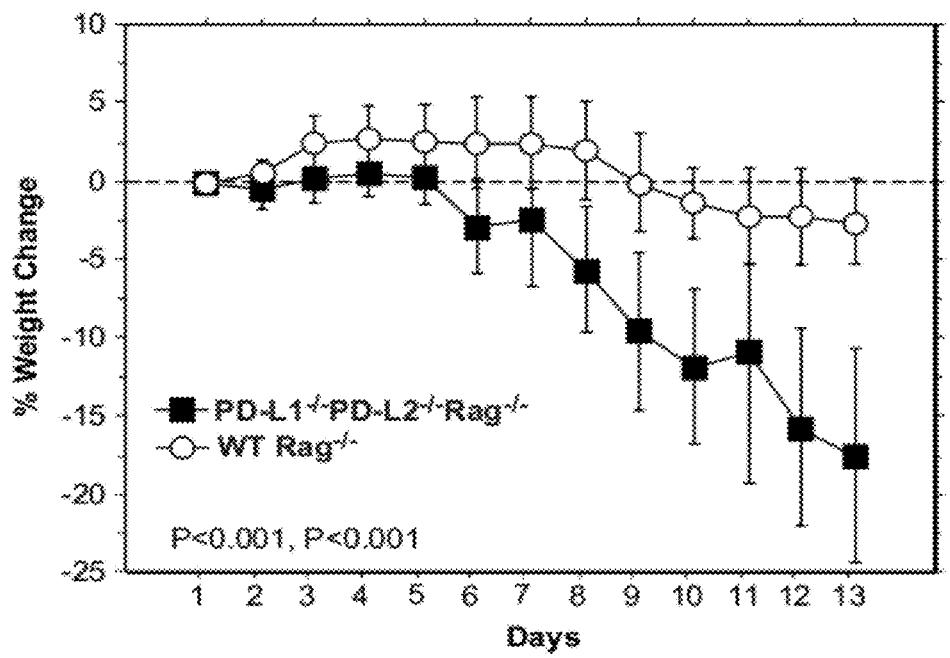
FIGS. 6A-6C depict that adoptive transfer of naïve $CD4^+$ T cells into WT $Rag^{-/-}$ or $PD-L1^{-/-}PD-L2^{-/-}Rag^{-/-}$ mice leads to severe weight loss and lymphoproliferation in the absence of PD-L1. Sorted $CD4^+CD62L^{hi}Foxp3.GFP^-$ cells were adoptively transferred i.v. into WT $Rag^{-/-}$ or $PD-L1^{-/-}PD-L2^{-/-}Rag^{-/-}$ mice. Clinical manifestations: (A) % weight loss of mice following adoptive transfer of $CD4^+ CD62L^{hi}Foxp3.GFP^-$ cells into WT $Rag^{-/-}$ or $PD-L1^{-/-}PD-L2^{-/-}Rag^{-/-}$, n=5 mice per group, (B) lymph nodes and spleens were observed in $PD-L1^{-/-}PD-L2^{-/-}Rag^{-/-}$ mice; spleens and lymph nodes (axillary, brachial, inguinal) from $PD-L1^{-/-}PD-L2^{-/-}Rag^{-/-}$ (left) and WT $Rag^{-/-}$ mice (right) are shown for comparison and (C) lymph node cellularity was quantified. Data represent the mean±s.d. and represent two independent experiments.
Figure 6B:
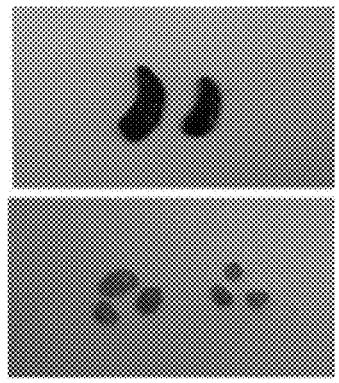
Figure 6C:
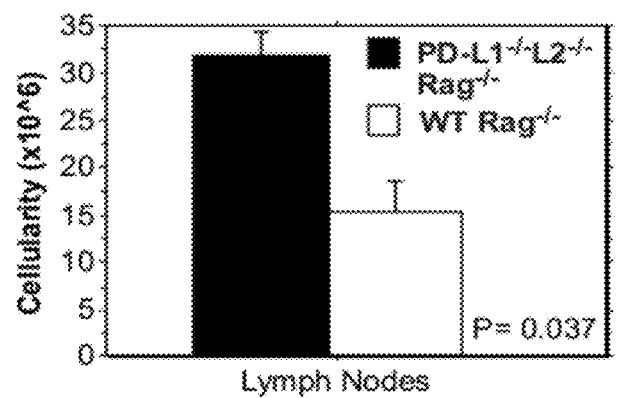

PD-L1$^{-/-}$PD-L2$^{-/-}$Rag$^{-/-}$ Mice Developed Fatal Immune-Mediated Pulmonary Damage Following Transfer of Naïve CD4$^+$Foxp3$^-$ T Cells To test whether there are in vivo consequences of the skewed Treg:Teff ratio in the PD-L1$^{-/-}$PD-L2$^{-/-}$Rag$^{-/-}$ recipients, PD-L1$^{-/-}$PD-L2$^{-/-}$Rag$^{-/-}$ or WT Rag$^{-/-}$ mice were observed after transfer of CD4$^+$CD62L$^{hi}$Foxp3.GFP$^-$ T cells (FIG. 6A). PD-L1$^{-/-}$PD-L2$^{-/-}$Rag$^{-/-}$ recipients exhibited rapid and dramatic weight loss beginning on day six post-transfer, with a reduction of 17.6%±5.7 (P 0.0001) of the pre-transfer body weight within two weeks post-naïve T cell transfer, compared to 2.65%±2.7 (P=0.100) weight loss observed for WT Rag$^{-/-}$ recipients (n=5 mice per group). Analysis of spleens and lymph nodes from mice on days 14 to 17 post-transfer revealed notable spleen and lymph node enlargement (FIG. 6B) and increased cellularity in adoptively transferred PD-L1$^{-/-}$PD-L2$^{-/-}$Rag$^{-/-}$ vs. WT Rag$^{-/-}$ recipients (FIG. 6C).

Figure 7A:
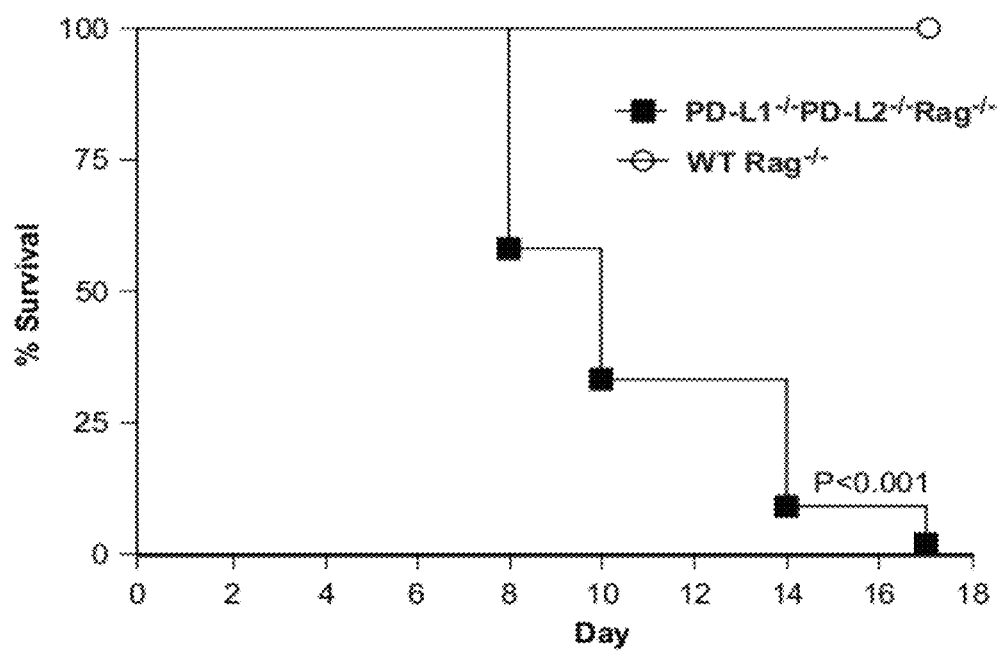
FIGS. 7A-7E depict fatal inflammatory disorder and severe pulmonary inflammation of $PD-L1^{-/-}PD-L2^{-/-}Rag^{-/-}$ following adoptive transfer of naïve $CD4^+ CD62L^{hi}Foxp3.GFP^-$ T cells. (A) Survival of mice following adoptive transfer of naïve $CD4^+CD62L^{hi}Foxp3.GFP^-$ T cells was monitored for 17 days. $PD-L1^{-/-}PD-L2^{-/-}Rag^{-/-}$, n=12, and WT $Rag^{-/-}$, n=8. (B-E) Examination of hematoxylin and eosin-stained paraffin sections of lung tissue obtained on days 14-17 post-transfer of naïve $CD4^+ CD62L^{hi}Foxp3^-$ T cells. Data represent two independent experiments with n=9, $PD-L1^{-/-}PD-L2^{-/-}Rag^{-/-}$ and n=10, WT $Rag^{-/-}$. (B, C) lung at 4× and (D, E) lung at 40×.
Figure 7B:
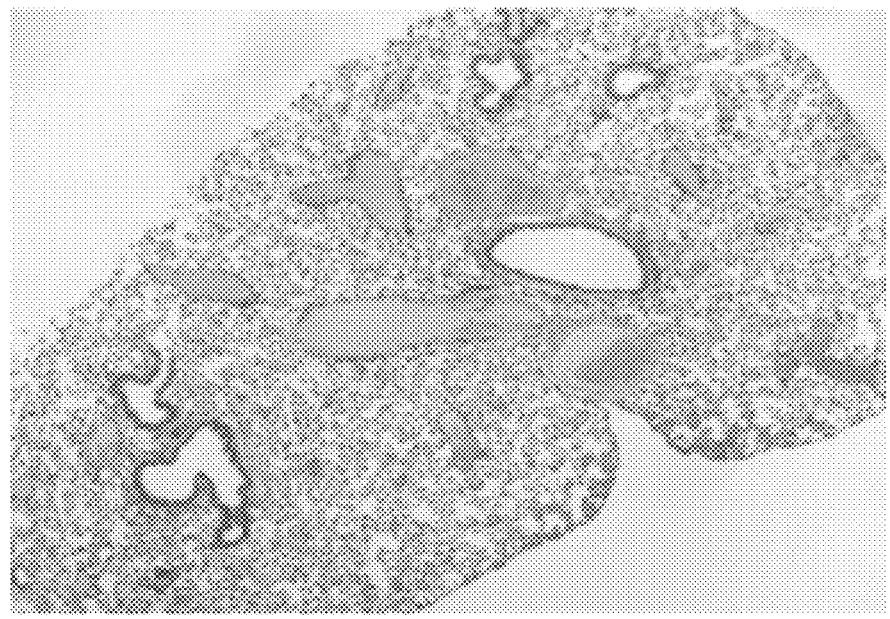
Figure 7C:
Figure 7D:
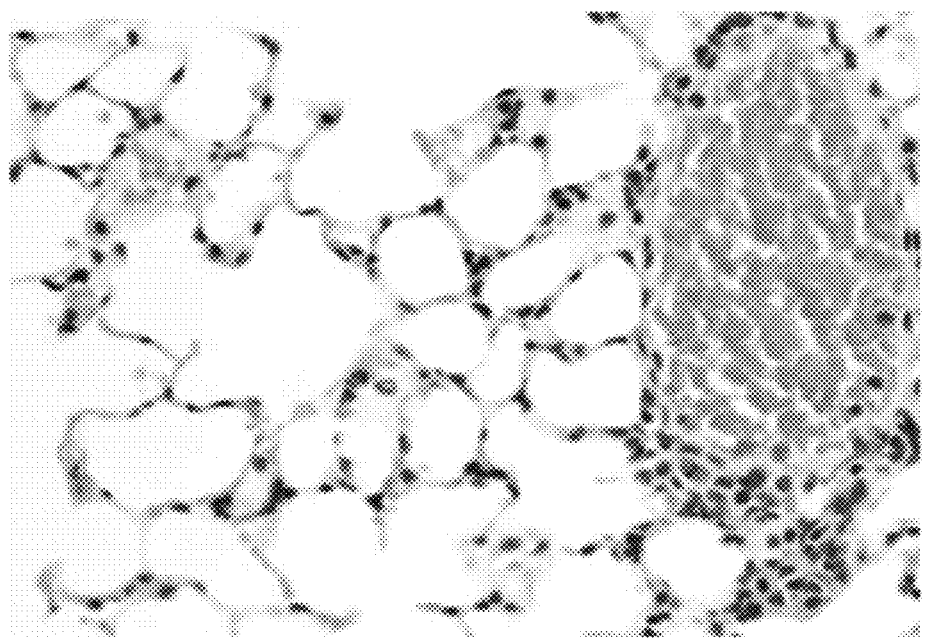
Figure 7E:
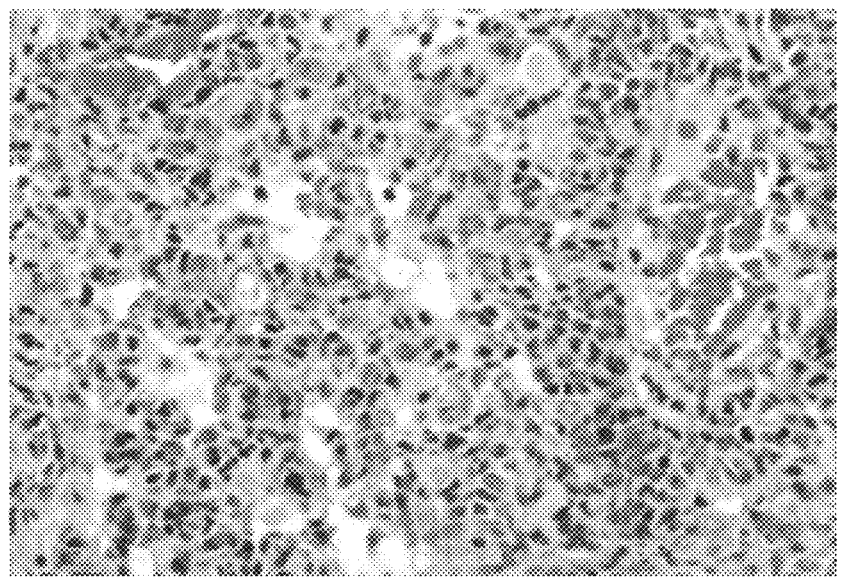

PD-L1$^{-/-}$PD-L2$^{-/-}$Rag$^{-/-}$ recipients all died within 17 days following transfer of naïve T cells (n=12), in marked contrast to the survival of all WT Rag$^{-/-}$ recipients (n=8) (FIG. 7A). In a separate experiment, PD-L1$^{-/-}$PD-L2 Rag$^{-/-}$ and WT Rag$^{-/-}$ recipients were examined histologically on days 14 to 17 post-transfer (FIGS. 7B-7E). The lungs of PD-L1$^{-/-}$PD-L2$^{-/-}$Rag$^{-/-}$ recipients showed pervasive and severe perivascular, peribronchial and interstitial infiltrates consisting predominantly of mononuclear cells and some neutrophils. Alveolar walls were markedly thickened by the inflammation, and there was also severe alveolar consolidation and edema. Without intending to be bound by scientific theory, this potentially resulted in a reduction in the volume of functional alveoli for potential respiratory gas exchange in these mice. In contrast, all the WT Rag$^{-/-}$ recipients displayed a minimal degree of inflammation and absence of alveolar consolidation in the lungs. Animals from both groups showed varying degrees of active hepatitis. Both groups had thromboses in some hepatic vessels and foci of hepatic infarction. The large intestines from both groups showed varying degrees of active colitis on days 14 to 17 after adoptive transfer. Analysis of brain, heart, pancreas, kidney, esophagus, stomach, small intestine and skin revealed minimal inflammation with no differences between PD-L1$^{-/-}$PD-L2$^{-/-}$Rag$^{-/-}$ or WT Rag$^{-/-}$ recipients.

To ascertain the critical role for PD-L1 in vivo, naïve CD4 T cells were transferred to Rag$^{-/-}$ recipients treated with anti-PD-L1 blocking antibody (FIGS. 12A-12B), and the mice were monitored for 3 to 4 weeks. Mice were sacrificed to assess T reg cell development and immunopathology. A significant defect in de novo iT reg cell development was observed in Rag$^{-/-}$ mice given the anti-PD-L1 mAb compared with isotype control in both the spleen (isotype=6.35% vs. anti-PD-L1=2.73%, P=0.0318) and mesenteric lymph nodes (isotype=30.2% vs. anti-PD-L1=18%, P=0.0219. The lungs of Rag$^{-/-}$ mice treated with anti-PD-L1 mAb showed moderate to severe perivascular, peribronchial and interstitial inflammation, consisting of mononuclear cells and a few scattered neutrophils. Thus, similar to the PD-L1$^{-/-}$PD-L2$^{-/-}$Rag$^{-/-}$ recipients of naïve CD4 T cells, WT Rag$^{-/-}$ mice give anti-PD-L1 mAb exhibited defects in iT reg cell generation and developed pulmonary pathology. Collectively, these data demonstrate a key role for PD-L1 in iT reg cell development in vivo.

Example VI

PD-L1 Ig Prevents Lymphoproliferative Disease-Induced Weight Loss

Figure 8:
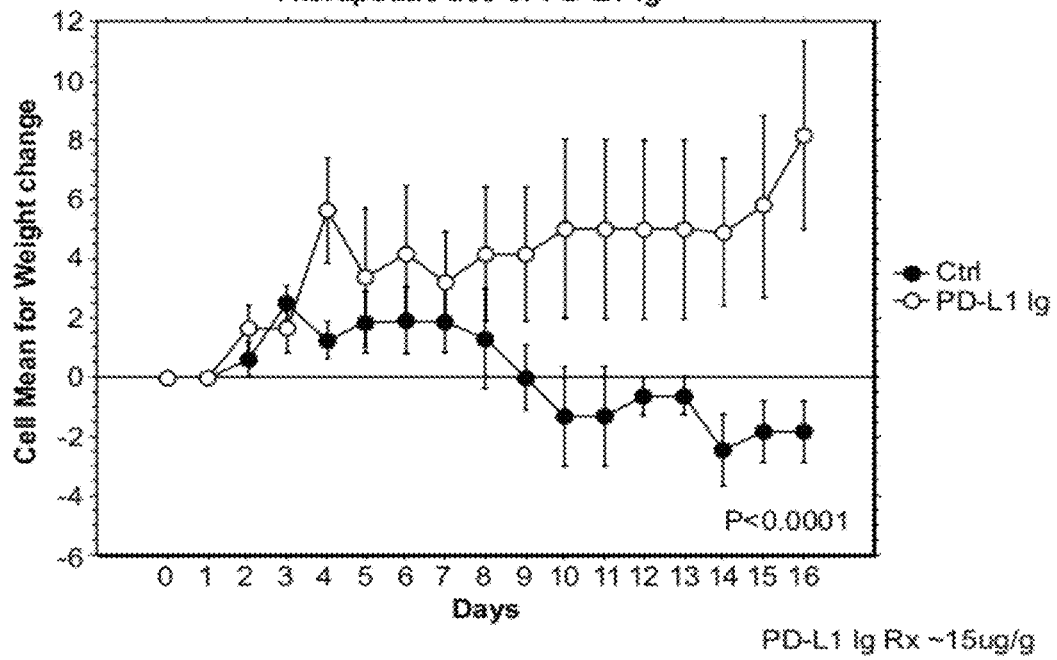
FIG. 8 is a graph showing lymphoproliferative disease-induced weight loss in control mice compared to mice treated with PD-L1 Ig. PD-L1 Ig can prevent lymphoproliferative disease-induced weight loss. $1 \times 10^4$ Naïve $CD4^+ CD62L^+ FoxP3.GFP^-$ T cells were intravenously transferred into $PD-L1^{-/-}PD-L2^{-/-} Rag^{-/-}$ mice on day 0. Mice were treated (I.P) with 300 ug of hPD-L1-Ig daily, beginning on day −1 or left untreated. Mice were weighed daily for 16 days.

1×10$^4$ Naïve CD4$^+$ CD62L$^+$ FoxP3.GFP$^-$ T cells were intravenously transferred into PD-L1$^{-/-}$PD-L2$^{-/-}$ Rag$^{-/-}$ mice on day 0. Mice were treated (I.P) with 300 ug of hPD-L1-Ig daily, beginning on day −1 or left untreated. Mice were weighed daily for 16 days. As FIG. 8 shows, the control mice lost weight over time attributable to lymphoproliferative disease. In contrast, the mice having the same disease actually gained weight overtime when administered PD-L1 Ig. Administration of PD-L1 Ig rescued PD-L1$^{-/-}$PD-L2$^{-/-}$Rag$^{-/-}$ mice from rapid fatal phenotype following transfer of naïve T cells. These results demonstrate that PD-L1 Ig is an effective treatment for lymphoproliferative diseases and inflammation in vivo. Administration of PD-L1 agonists sustain and enhance the function of T regulatory cells in vivo.

Example VII

PD-L1 Induces iTreg Development Via B7-1

Figure 9:
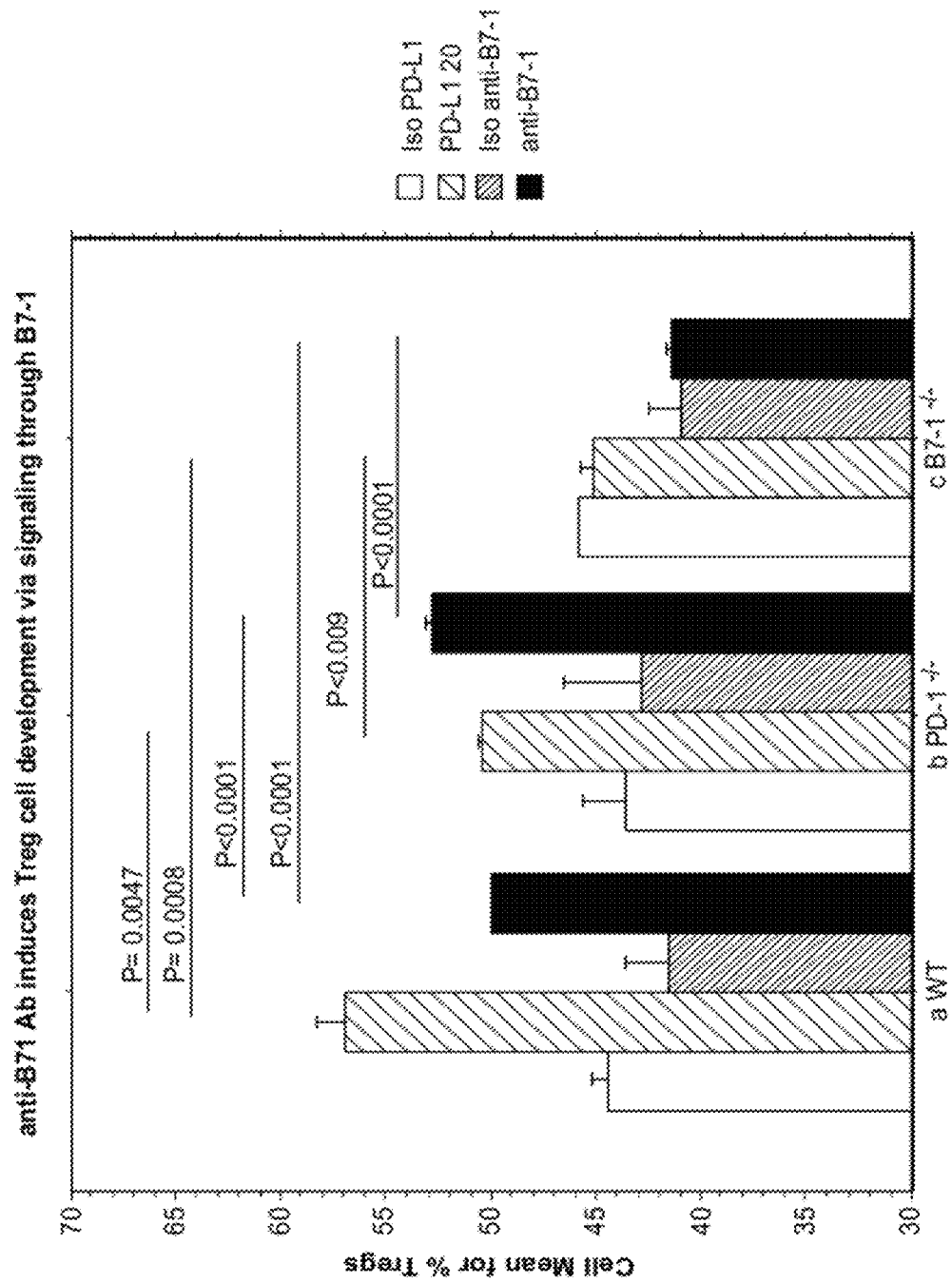
FIG. 9 is a graph showing that anti-B71 antibody induces Treg cell development via signaling through B7-1. Naïve $CD4^+ CD62L^+FoxP3.GFP-$ T cells were sorted from WT FoxP3.GFP, $PD-1^{-/-}FoxP3.GFP$ or $B7-1^{-/-}$ FoxP3.GFP reporter mice and co-cultured with expoxy beads coated with anti-CD3, anti-CD28 and either PD-L1 Ig, control Ig, anti-B7-1 Ab (16-10-A1) or anti-hamster Ig control, in the presence of TGF-b. $CD4^+$ T cells were analyzed for FoxP3.GFP expression by flow cytometry after 3 days of culture.

Naïve CD4$^+$ CD62L$^+$FoxP3.GFP– T cells were sorted from WT FoxP3.GFP, PD-1$^{-/-}$ FoxP3.GFP or B7-1$^{-/-}$ FoxP3.GFP reporter mice and co-cultured with epoxy beads coated with anti-CD3, anti-CD28 and either PD-L1 Ig, control Ig, anti-B7-1 Ab (16-10-A1) or anti-hamster Ig control, in the presence of TGF-β. CD4$^+$ T cells were analyzed for FoxP3.GFP expression by flow cytometry after three days of culture. As FIG. 9 shows, PD-L1 can induce iTreg development at least in large part by engaging B7-1.

Example VIII

Figure 10A:
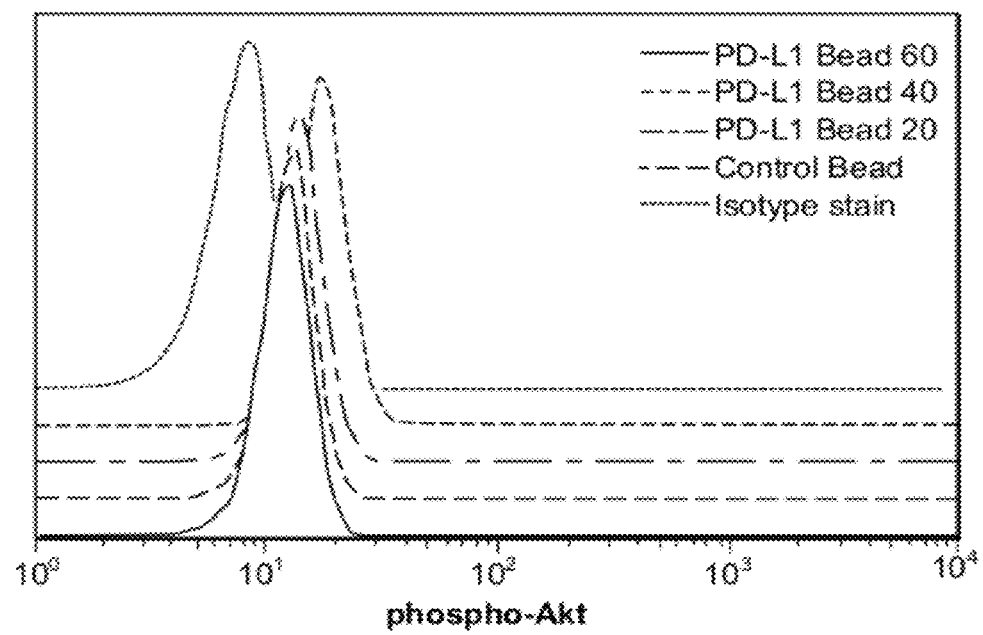
FIGS. 10A-10H depict PD-L1 regulation of T reg cell development by antagonizing the Akt-mTOR signaling cascade. (A), (C), (F), (G) Phospho-Akt, phospho-mTOR, PTEN, and phospho-S6 analysis at 18 hours after culture with control Ig bead (hIgG=60% of bead surface, with remaining surface coated with CD3 and anti-CD28) or various titers of PD-L1-Ig bead (PD-L1-Ig 20, 40, 60=20, 40 and 60% of bead surface coated with PD-L1-Ig, with remaining surface coated with anti-CD3 and anti-CD28 plus control Ig). (B), (D), (E), (H), MFI analysis of phosphor-Akt (B; *, P=0.001; , P=0.003; and *, P=0.0008, at 20, 40 and 60% PD-L1, respectively, compared with control Ig), phosphor-mTOR (D; *, P=0.0064; and **, P=0.0001, at 20 and 60% PD-L1, respectively, compared with control Ig, phospho-S6 (E; P=0.0012, P=0.0007, and P=0.0002, at 20, 40, and 60% PD-L1, respectively, compared with control Ig) and PTEN (H; *, P=0.0378, PD-L1-Ig 40 compared with control Ig) at 18 hours. n=3 mice per experiment, representative of three experiments. Data are representative of the MFI±SD and are representative of three experiments.
Figure 10B:
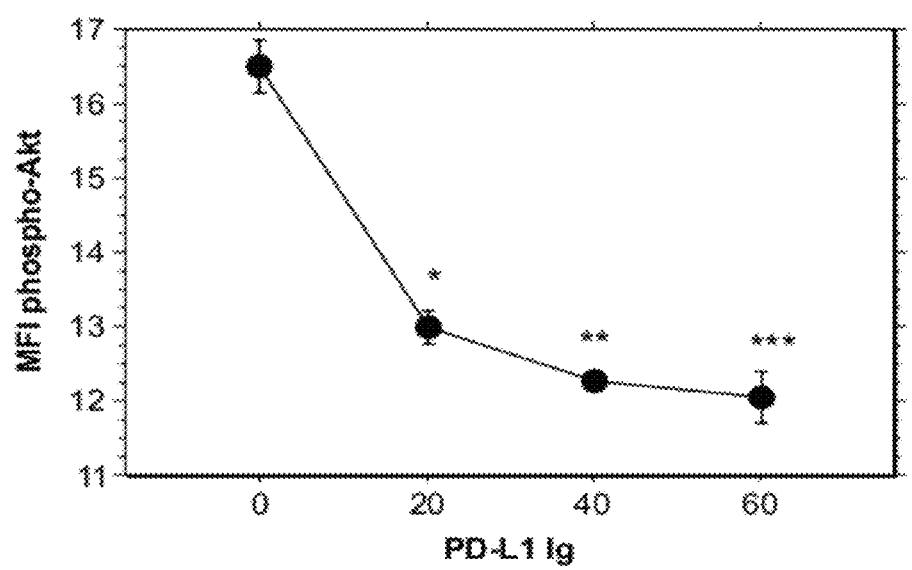
Figure 10C:
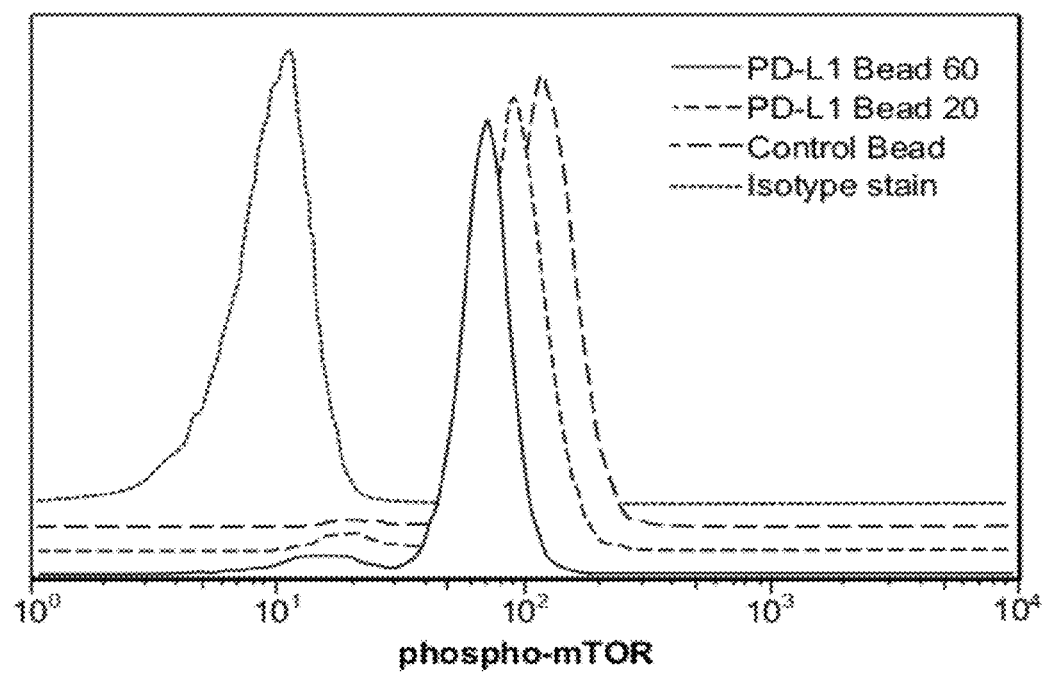
Figure 10D:
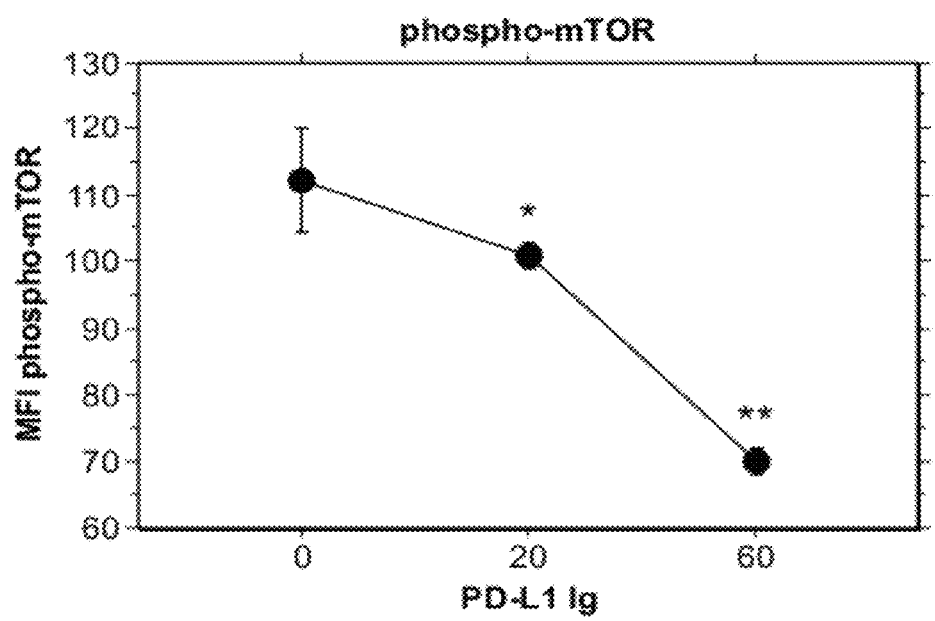
Figure 10E:
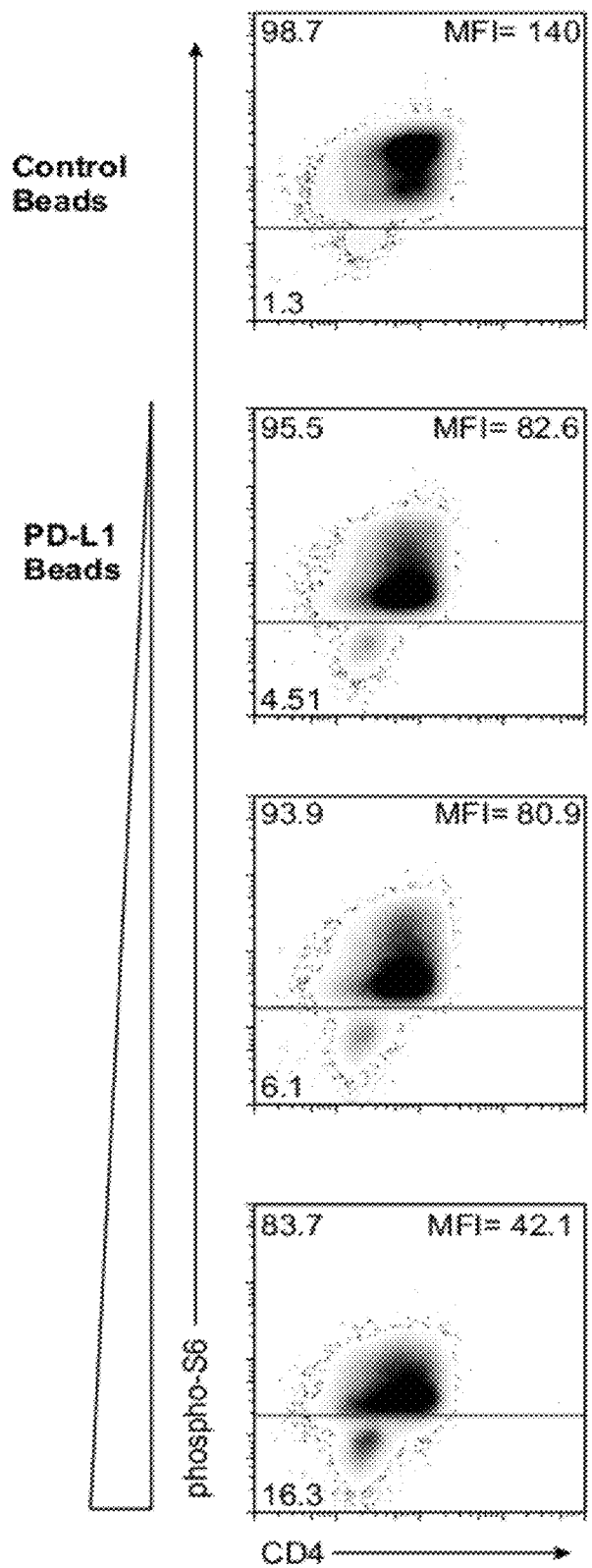
Figure 10F:
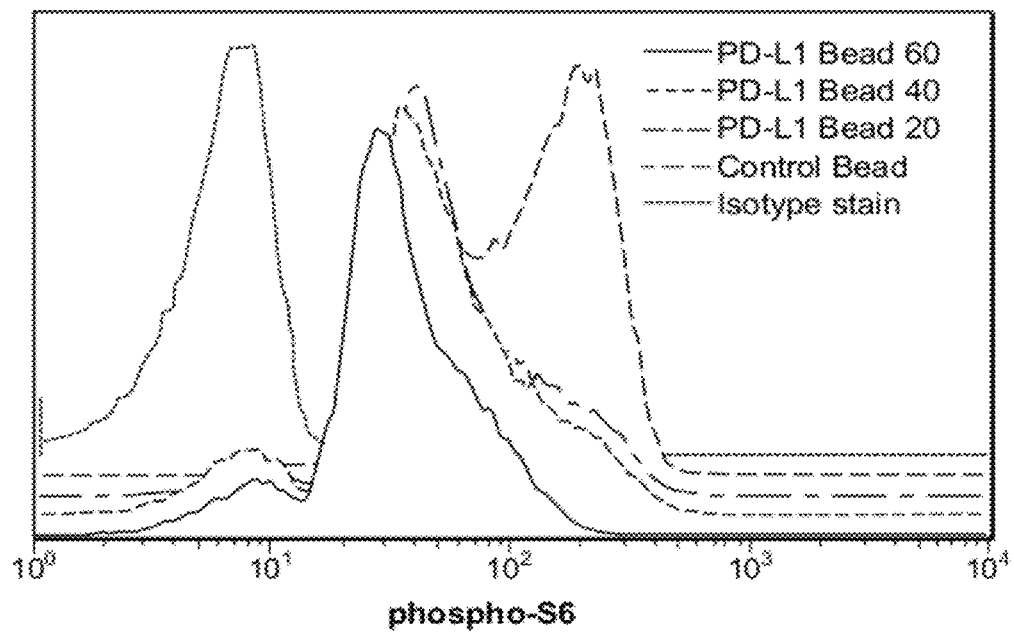
Figure 10G:
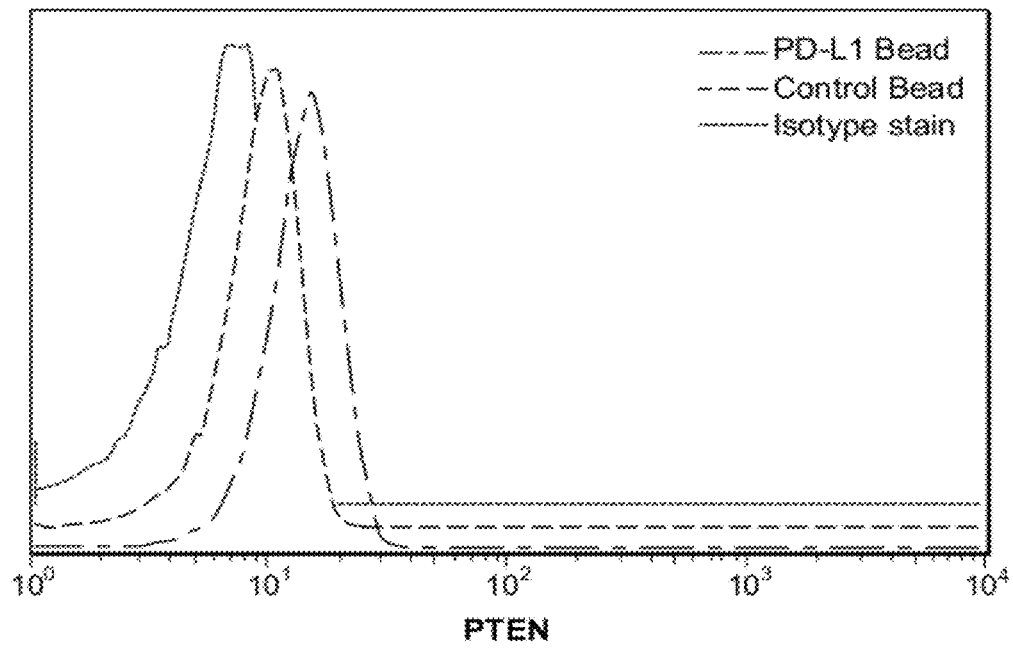
Figure 10H:
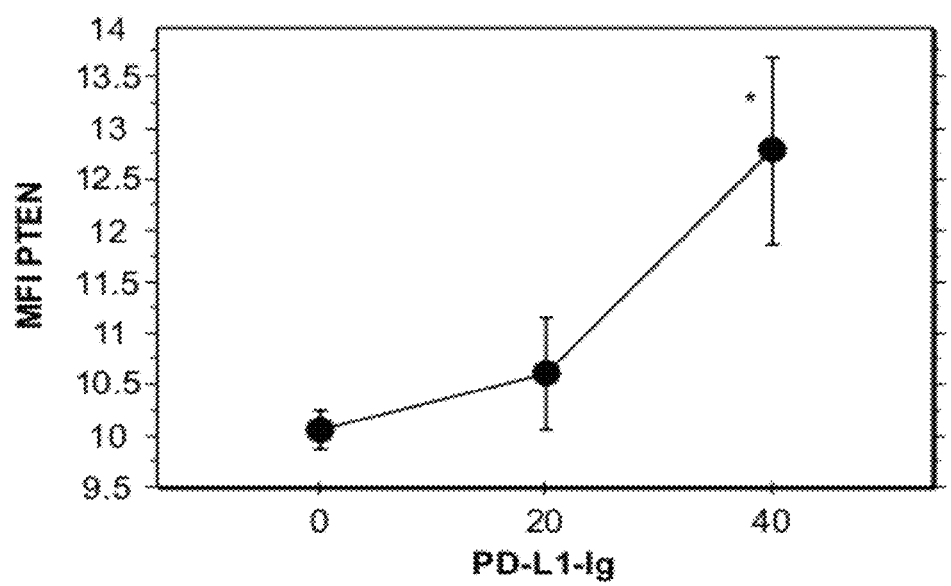

PD-L1 Antagonizes the Akt-mTOR Signaling Cascade During the Induction of Induced T Regulatory Cells There are notable differences in signaling pathways utilized by CD4$^+$ effector T cells compared with Tregs. In particular, Akt signaling is essential for naïve T cell activation and proliferation, but truncation of TCR signaling and inhibition of the Akt-mTOR signaling axis is critical for regulatory T cell development. To determine whether PD-L1 mediates Treg conversion by antagonizing the Akt signaling pathway naïve T cells were cultured in the presence of PD-L1-Ig or control-Ig beads for 18 hours and then phosphorylation of Akt, mTOR and S6 was measured. Intracellular staining for phospho-Akt and phospho-mTOR revealed significantly diminished levels of Akt and mTOR phosphorylation when naïve T cells were cultured in the presence of increasing quantities of PD-L1 relative to control-Ig (Mean Fluorescence Intensities (MFIs) of phospho-Akt and phospho-mTOR were significantly down-regulated) (FIGS. 10A-10D). As a downstream target of the mTOR-regulated p70 S6 kinase, phosphorylation of S6 ribosomal protein reflects the sustained activation of the Akt-mTOR pathway. Upon culture of naïve CD4 T cells with increasing amounts of PD-L1, a marked decrease in phospho-S6 was observed as compared to control (FIGS. 10E-10F). Furthermore, PD-L1 up-regulated the expression of phosphatase and tensin homolog deleted on chromosome 10 (PTEN), a phosphoinositol 3,4,5-triphosphatase important for antagonizing PI3K signaling, demonstrating that PD-L1 antagonized the Akt pathway during Treg differentiating conditions (FIGS. 10G-10H). Western blots assessing the specific down-regulation of phospho-Akt, phospho-mTOR, phospho-S6 and up-regulation of PTEN confirmed phospho-flow cytometry data.

Figure 11:
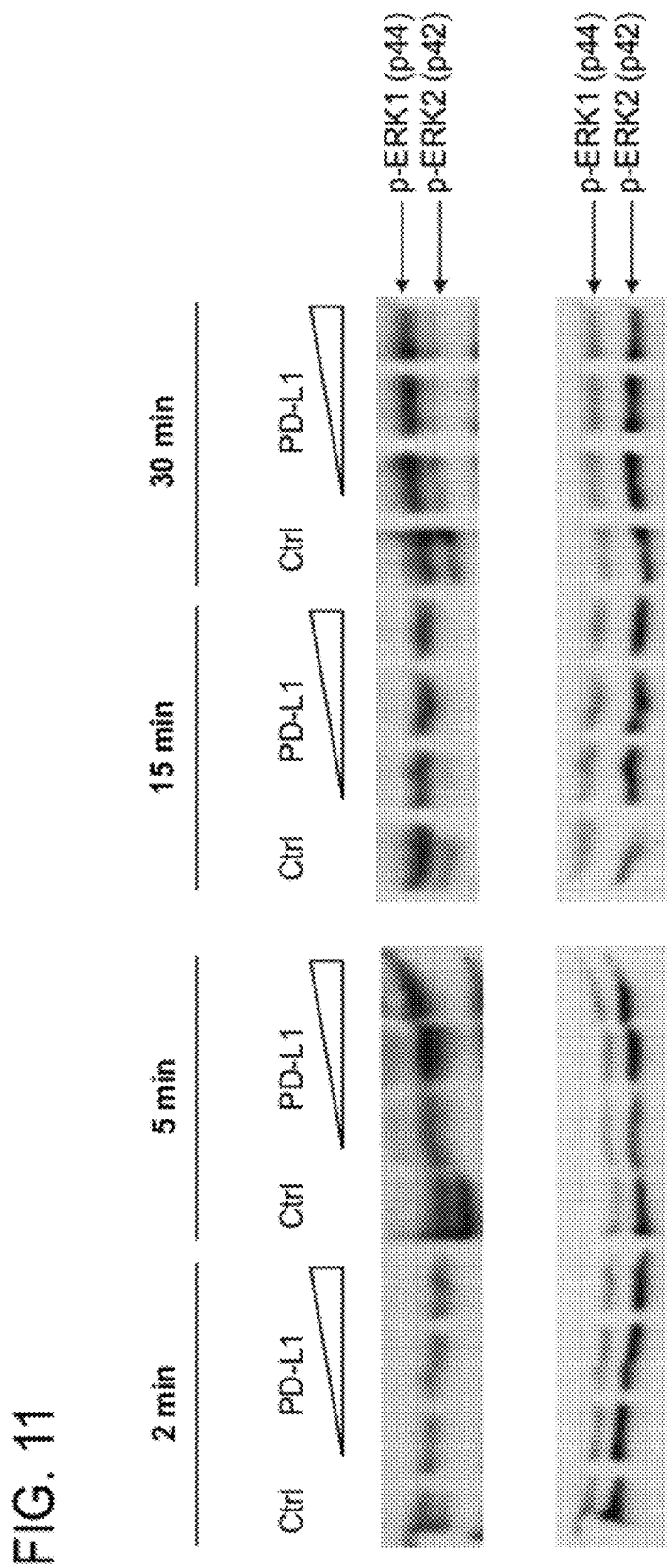
FIG. 11 depicts attenuation of ERK2/p42 phosphorylation upon stimulation of naïve T cells with increasing amounts of PD-L1 Ig.

Because down-regulation of the MAP kinase signaling cascade has also been implicated in TGF-β-mediated Treg development determine whether PD-L1 regulates Treg differentiation by modulating the MAP kinase pathway, naïve T cells were stimulated with increasing amounts of PD-L1 Ig attenuated the phosphorylation of ERK2/p42 (FIG. 11). These data further substantiate that the PD-L1:PD-1 pathway truncates signaling cascades downstream of TCR signaling, preferentially converting naïve T cells toward the regulatory T cell lineage.

Example IX

PD-L2 Promotes Adaptive Regulatory T Cell Development and Function

Figure 13A:
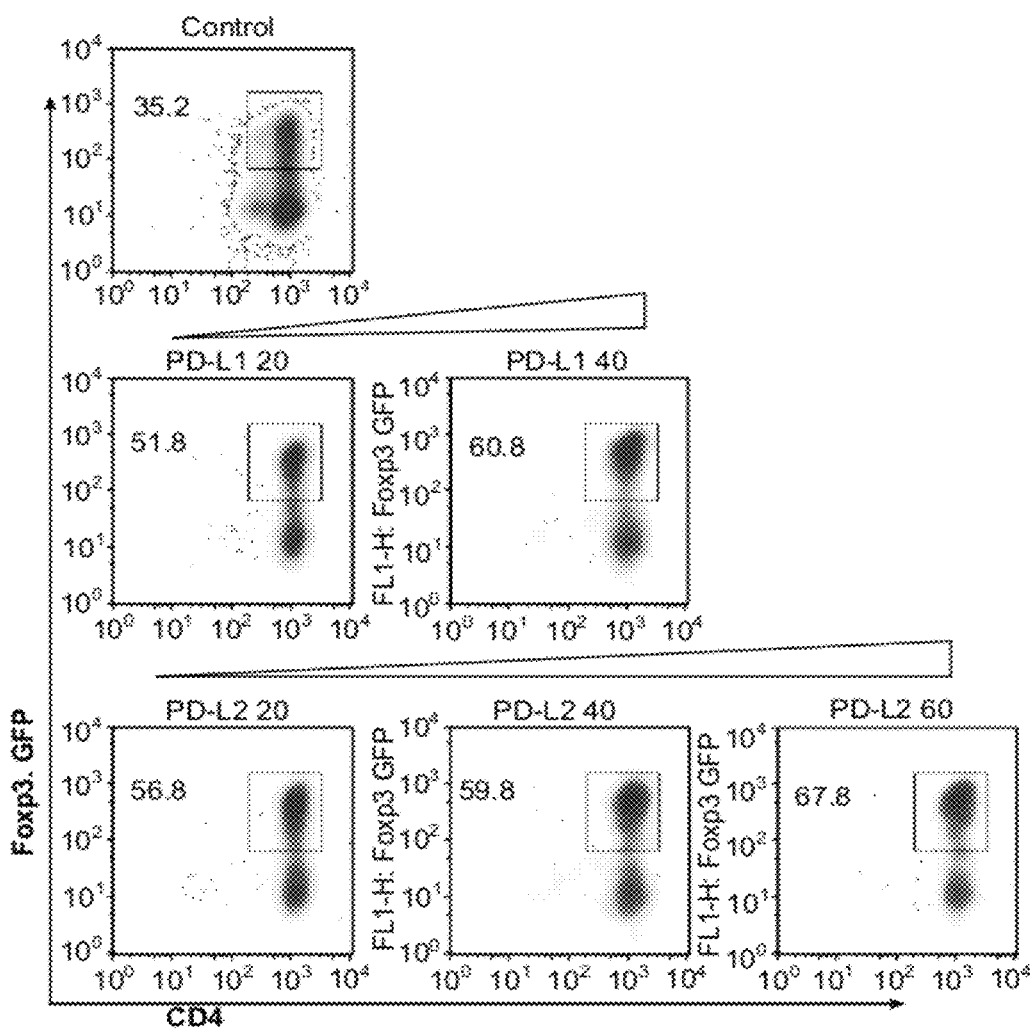
Figure 14A:
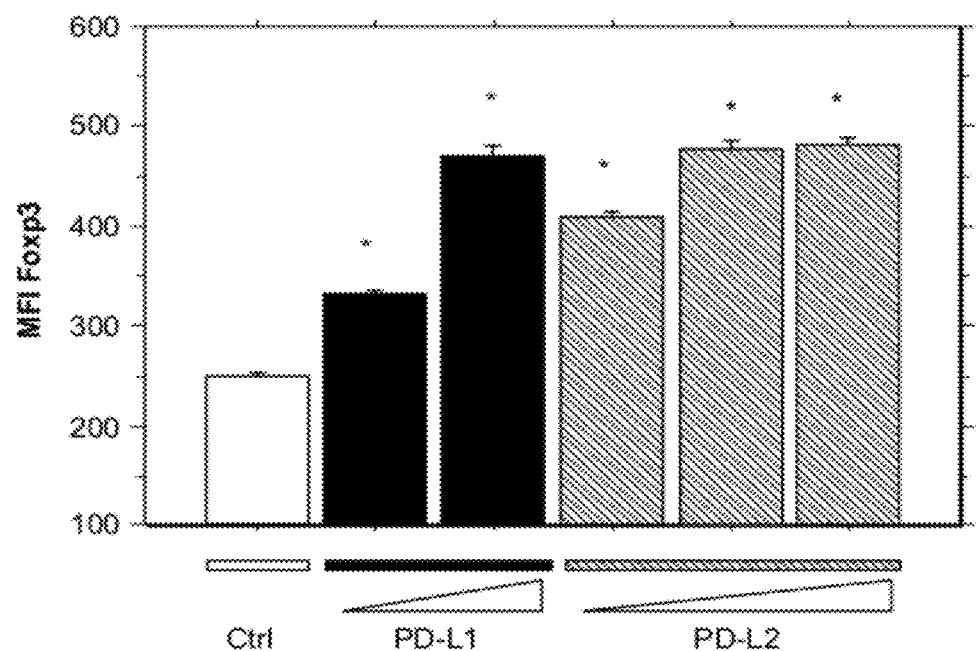
FIGS. 14A-14B graphically depict that PD-L2 regulates Foxp3 expression in adaptive Tregs. Mean fluorescence intensity (MFI) of Foxp3 was assayed by flow cytometry following Treg induction mediated by PD-Ligand coated beads. Naïve CD4$^+$CD62L$^+$Foxp3$^-$ T cells were cultured with PD-Ligand or control coated beads and TGF-β in the absence (A) or presence (B) of IL-2.
Figure 14B:
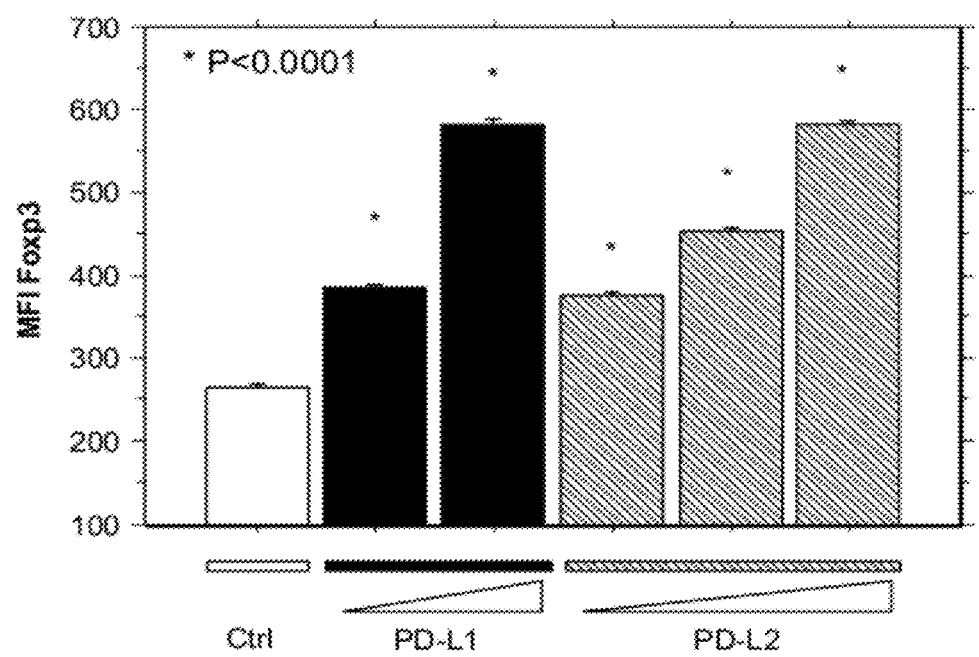

To compare the roles of PD-L1 and PD-L2 in iTreg development, we used epoxy beads to which anti-CD3, anti-CD28, and PD-L1-Ig or PD-L2-Ig or control Ig were attached as artificial APCs (henceforth referred to as PD-L1-Ig, PD-L2-Ig or control Ig beads). Naïve CD4$^+$ CD62L$^+$ Foxp3.GFP$^-$ T cells were cultured with either PD-L-Ig, PD-L2-Ig or control Ig beads in the presence of TGF-β without (13A) or with (13B) IL-2. The amounts of PD-L1-Ig and PD-L2-Ig on the surface of the beads were titered by covalently attaching a range of concentrations of PD-L1 and PD-L2 to the epoxy beads. PD-L2 induced adaptive Treg development as effectively as PD-L1 (FIGS. 13A-13B). At lower quantities of PD-L1 and PD-L2, the levels of Foxp3 expression per cell were increased to a greater extent by PD-L2-Ig beads than PD-L1-Ig beads compared to control beads in the absence of IL-2 (FIG. 14A). The levels of Foxp3 expression per cell were similarly increased by PD-L1-Ig and PD-L2-Ig beads compared to control beads in the presence of IL-2 (FIG. 14B), as evidenced by the mean fluorescence intensity of Foxp3 GFP expression.

REFERENCES

Adler, H. S., S. Kubsch, E. Graulich, S. Ludwig, J. Knop, and K. Steinbrink. 2007. Activation of MAP kinase p38 is critical for the cell-cycle controlled suppressor function of regulatory T cells. Blood. 109:4351-4359. doi:10.1182/blood-2006-09-047563

Baecher-Allan, C., J. A. Brown, G. J. Freeman, and D. A. Hafler. 2003. CD4+CD25+ regulatory cells from human peripheral blood express very high levels of CD25 ex vivo. Novartis Found. Symp. 252:67-88, discussion:88-91: 106-114. doi:10.1002/0470871628.ch6

Barber, D. L., E. J. Wherry, D. Masopust, B. Zhu, J. P. Allison, A. H. Sharpe, G. J. Freeman, and R. Ahmed. 2006. Restoring function in exhausted CD8 T cells during chronic viral infection. Nature. 439:682-687. doi:10.1038/nature04444

Battaglia, M., A. Stabilini, B. Migliavacca, J. Horejs-Hoeck, T. Kaupper, and M. G. Roncarolo. 2006. Rapamycin promotes expansion of functional CD4+CD25+FOXP3+ regulatory T cells of both healthy subjects and type 1 diabetic patients. J. Immunol. 177:8338-8347.

Belkaid, Y. 2008. Role of Foxp3-positive regulatory T cells during infection. Eur. J. Immunol. 38:918-921. doi:10.1002/eji.200738120

Beswick, E. J., I. V. Pinchuk, S. Das, D. W. Powell, and V. E. Reyes. 2007. Expression of the programmed death ligand 1, B7-H1, on gastric epithelial cells after Helicobacter pylori exposure promotes development of CD4+CD25+ FoxP3+ regulatory T cells. Infect. Immun. 75:4334-4341. doi:10.1128/IAI.00553-07

Bettelli, E., M. Pagany, H. L. Weiner, C. Linington, R. A. Sobel, and V. K. Kuchroo. 2003. Myelin oligodendrocyte glycoprotein-specific T cell receptor transgenic mice develop spontaneous autoimmune optic neuritis. J. Exp. Med. 197:1073-1081. doi:10.1084/jem.20021603

Bettelli, E., Y. Carrier, W. Gao, T. Korn, T. B. Strom, M. Oukka, H. L. Weiner, and V. K. Kuchroo. 2006. Reciprocal developmental pathways for the generation of pathogenic effector TH17 and regulatory T cells. Nature. 441:235-238. doi:10.1038/nature04753

Blank, C., T. F. Gajewski, and A. Mackensen. 2005. Interaction of PD-L1 on tumor cells with PD-1 on tumor-specific T cells as a mechanism of immune evasion: implications for tumor immunotherapy. Cancer Immunol. Immunother. 54:307-314. doi:10.1007/s00262-004-0593-x Bloom, D. D., Z. Chang, J. H. Fechner, W. Dar, S. P. Polster, J. Pascual, L. A. Turka, and S. J. Knechtle. 2008. CD4+CD25+ FOXP3+ regulatory T cells increase de novo in kidney transplant patients after immunodepletion with Campath-1H. Am. J. Transplant. 8:793-802. doi:10.1111/j.1600-6143.2007.02134.x Broeren, C. P., G. S. Gray, B. M. Carreno, and C. H. June. 2000. Costimulation light: activation of CD4+ T cells with CD80 or CD86 rather than antiCD28 leads to a Th2 cytokine profile. J. Immunol. 165:6908-6914.

Brown, J. A., D. M. Dorfman, F. R. Ma, E. L. Sullivan, O. Munoz, C. R. Wood, E. A. Greenfield, and G. J. Freeman. 2003. Blockade of programmed death-1 ligands on dendritic cells enhances T cell activation and cytokine production. J. Immunol. 170:1257-1266.

Brunkow, M. E., E. W. Jeffery, K. A. Hjerrild, B. Paeper, L. B. Clark, S. A. Yasayko, J. E. Wilkinson, D. Galas, S. F. Ziegler, and F. Ramsdell. 2001. Disruption of a new forkhead/winged-helix protein, scurfin, results in the fatal lymphoproliferative disorder of the scurfy mouse. Nat. Genet. 27:68-73. doi:10.1038/83784

Calzascia, T., M. Pellegrini, A. Lin, K. M. Garza, A. R. Elford, A. Shahinian, P. S. Ohashi, and T. W. Mak. 2008. CD4 T cells, lymphopenia, and IL-7 in a multistep pathway to autoimmunity. Proc. Natl. Acad. Sci. USA. 105: 2999-3004. doi:10.1073/pnas.0712135105

Chen, W., W. Jin, N. Hardegen, K. J. Lei, L. L1, N. Marinos, G. McGrady, and S. M. Wahl. 2003. Conversion of peripheral CD4+CD25. naive T cells to CD4+CD25+ regulatory T cells by TGF-. induction of transcription factor Foxp3. J. Exp. Med. 198:1875-1886. doi:10.1084/jem.20030152

Clark, L. B., M. W. Appleby, M. E. Brunkow, J. E. Wilkinson, S. F. Ziegler, and F. Ramsdell. 1999. Cellular and molecular characterization of the scurfy mouse mutant. J. Immunol. 162:2546-2554.

Coenen, J. J., H. J. Koenen, E. van Rijssen, A. Kasran, L. Boon, L. B. Hilbrands, and I. Joosten. 2007. Rapamycin, not cyclosporine, permits thymic generation and peripheral preservation of CD4+ CD25+ FoxP3+ T cells. Bone Marrow Transplant. 39:537-545. doi:10.1038/sj.bmt.1705628

Collison, L. W., C. J. Workman, T. T. Kuo, K. Boyd, Y. Wang, K. M. Vignali, R. Cross, D. Sehy, R. S. Blumberg, and D. A. Vignali. 2007. The inhibitory cytokine IL-35 contributes to regulatory T-cell function. Nature. 450:566-569. doi:10.1038/nature06306

Coombes, J. L., K. R. Siddiqui, C. V. Arancibia-Cárcamo, J. Hall, C. M. Sun, Y. Belkaid, and F. Powrie. 2007. A functionally specialized population of mucosal CD103+ DCs induces Foxp3+ regulatory T cells via a TGF-.—and retinoic acid-dependent mechanism. J. Exp. Med. 204: 1757-1764. doi:10.1084/jem.20070590

Das, S., G. Suarez, E. J. Beswick, J. C. Sierra, D. Y. Graham, and V. E. Reyes. 2006. Expression of B7-H1 on gastric epithelialcells: its potential roleinregulating T cells during Helicobacter pylori infection. J. Immunol. 176:3000-3009.

Dong, H., S. E. Strome, D. R. Salomao, H. Tamura, F. Hirano, D. B. Flies, P. C. Roche, J. Lu, G. Zhu, K. Tamada, et al. 2002. Tumor-associated B7-H1 promotes T-cell apoptosis: a potential mechanism of immune evasion. Nat. Med. 8:793-800.

Dorfman, D. M., J. A. Brown, A. Shahsafaei, and G. J. Freeman. 2006. Programmed death-1 (PD-1) is a marker of germinal center-associated T cells and angioimmunoblastic T-cell lymphoma. Am. J. Surg. Pathol. 30:802-810. doi:10.1097/01.pas.0000209855.28282.ce Fantini, M. C., C. Becker, G. Monteleone, F. Pallone, P. R. Galle, and M. F. Neurath. 2004. Cutting edge: TGF-beta induces a regulatory phenotype in CD4+CD25− T cells through Foxp3 induction and down-regulation of Smad7. J. Immunol. 172:5149-5153.

Fontenot, J. D., M. A. Gavin, and A. Y. Rudensky. 2003. Foxp3 programs the development and function of CD4+ CD25+ regulatory T cells. Nat. Immunol. 4:330-336. doi:10.1038/ni904

Fontenot, J. D., J. P. Rasmussen, L. M. Williams, J. L. Dooley, A. G. Farr, and A. Y. Rudensky. 2005. Regulatory T cell lineage specification by the forkhead transcription factor foxp3. Immunity. 22:329-341. doi:10.1016/j.immuni.2005.01.016

Gao, W., Y. Lu, B. El Essawy, M. Oukka, V. K. Kuchroo, and T. B. Strom. 2007. Contrasting effects of cyclosporine and rapamycin in de novo generation of alloantigen-specific regulatory T cells. Am. J. Transplant. 7:1722-1732. doi: 10.1111/j.1600-6143.2007.01842.x Gavin, M. A., J. P. Rasmussen, J. D. Fontenot, V. Vasta, V. C. Manganiello, J. A. Beavo, and A. Y. Rudensky. 2007. Foxp3-dependent programme of regulatory T-cell differentiation. Nature. 445:771-775. doi:10.1038/nature05543

Haxhinasto, S., D. Mathis, and C. Benoist. 2008. The AKT-mTOR axis regulates de novo differentiation of CD4+ Foxp3+ cells. J. Exp. Med. 205:565-574. doi: 10.1084/jem.20071477

Hill, J. A., M. Feuerer, K. Tash, S. Haxhinasto, J. Perez, R. Melamed, D. Mathis, and C. Benoist. 2007. Foxp3 transcription-factor-dependent and -independent regulation of the regulatory T cell transcriptional signature. Immunity. 27:786-800. doi:10.1016/j.immuni.2007.09.010

Hirano, F., K. Kaneko, H. Tamura, H. Dong, S. Wang, M. Ichikawa, C. Rietz, D. B. Flies, J. S. Lau, G. Zhu, et al. 2005. Blockade of B7-H1 and PD-1 by monoclonal antibodies potentiates cancer therapeutic immunity. Cancer Res. 65:1089-1096.

Hori, S., T. Nomura, and S. Sakaguchi. 2003. Control of regulatory T cell development by the transcription factor Foxp3. Science. 299:1057-1061. doi:10.1126/science.1079490

Huber, S., J. Schrader, G. Fritz, K. Presser, S. Schmitt, A. Waisman, S. Lüth, M. Blessing, J. Herkel, and C. Schramm. 2008. P38 MAP kinase signaling is required for the conversion of CD4+CD25− T cells into iTreg. PLoS One. 3:e3302. doi:10.1371/journal.pone.0003302

Inman, B. A., T. J. Sebo, X. Frigola, H. Dong, E. J. Bergstralh, I. Frank, Y. Fradet, L. Lacombe, and E. D. Kwon. 2007. PD-L1 (B7-H1) expression by urothelial carcinoma of the bladder and BCG-induced granulomata: associations with localized stage progression. Cancer. 109:1499-1505. doi:10.1002/cncr.22588

Iwai, Y., M. Ishida, Y. Tanaka, T. Okazaki, T. Honjo, and N. Minato. 2002. Involvement of PD-L1 on tumor cells in the escape from host immune system and tumor immunotherapy by PD-L1 blockade. Proc. Natl. Acad. Sci. USA. 99:12293-12297. doi:10.1073/pnas.192461099

Joetham, A., S. Matsubara, M. Okamoto, K. Takeda, N. Miyahara, A. Dakhama, and E. W. Gelfand. 2008. Plasticity of regulatory T cells: subversion of suppressive function and conversion to enhancement of lung allergic responses. J. Immunol. 180:7117-7124.

Keir, M. E., S. C. Liang, I. Guleria, Y. E. Latchman, A. Qipo, L. A. Albacker, M. Koulmanda, G. J. Freeman, M. H. Sayegh, and A. H. Sharpe. 2006. Tissue expression of PD-L1 mediates peripheral T cell tolerance. J. Exp. Med. 203:883-895. doi:10.1084/jem.20051776

Keir, M. E., L. M. Francisco, and A. H. Sharpe. 2007a. PD-1 and its ligands in T-cell immunity. Curr. Opin. Immunol. 19:309-314. doi:10.1016/j.coi.2007.04.012

Keir, M. E., G. J. Freeman, and A. H. Sharpe. 2007b. PD-1 regulates self-reactive CD8+ T cell responses to antigen in lymph nodes and tissues. J. Immunol. 179:5064-5070.

Keir, M. E., M. J. Butte, G. J. Freeman, and A. H. Sharpe. 2008. PD-1 and its ligands in tolerance and immunity. Annu. Rev. Immunol. 26:677-704. doi:10.1146/annurev.immunol.26.021607.090331

Kim, J. M., J. P. Rasmussen, and A. Y. Rudensky. 2007. Regulatory T cells prevent catastrophic autoimmunity throughout the lifespan of mice. Nat. Immunol. 8:191-197. doi:10.1038/ni1428

Konishi, J., K. Yamazaki, M. Azuma, I. Kinoshita, H. Dosaka-Akita, and M. Nishimura. 2004. B7-H1 expression on non-small cell lung cancer cells and its relationship with tumor-infiltrating lymphocytes and their PD-1 expression. Clin. Cancer Res. 10:5094-5100. doi:10.1158/1078-0432. CCR-04-0428

Kronenberg, M., and A. Rudensky. 2005. Regulation of immunity by self-reactive T cells. Nature. 435:598-604. doi:10.1038/nature03725 Krupnick, A. S., A. E. Gelman, W. Barchet, S. Richardson, F. H. Kreisel, L. A. Turka, M. Colonna, G. A. Patterson, and D. Kreisel. 2005. Murine vascular endothelium activates and induces the generation of allogeneic CD4+25+Foxp3+ regulatory T cells. J. Immunol. 175:6265-6270.

Latchman, Y. E., S. C. Liang, Y. Wu, T. Chemova, R. A. Sobel, M. Klemm, V. K. Kuchroo, G. J. Freeman, and A. H. Sharpe. 2004. PD-L1-deficient mice show that PD-L1 on T cells, antigen-presenting cells, and host tissues negatively regulates T cells. Proc. Natl. Acad. Sci. USA. 101:10691-10696. doi:10.1073/pnas.0307252101

Liang, S., P. Alard, Y. Zhao, S. Parnell, S. L. Clark, and M. M. Kosiewicz. 2005. Conversion of CD4+ CD25. cells into CD4+ CD25+ regulatory T cells in vivo requires B7 costimulation, but not the thymus. J. Exp. Med. 201:127-137. doi:10.1084/jem.20041201

Lin, W., D. Haribhai, L. M. Relland, N. Truong, M. R. Carlson, C. B. Williams, and T. A. Chatila. 2007. Regulatory T cell development in the absence of functional Foxp3. Nat. Immunol. 8:359-368. doi:10.1038/ni1445

Lohr, J., B. Knoechel, and A. K. Abbas. 2006. Regulatory T cells in the periphery. Immunol. Rev. 212:149-162. doi:10.1111/j.0105-2896.2006.00414.x Long, S. A., and J. H. Buckner. 2008. Combination of rapamycin and IL-2 increases de novo induction of human CD4(+)CD25(+)FOXP3(+) T cells. J. Autoimmun. 30:293-302. doi:10.1016/j.jaut.2007.12.012

Luo, X., Q. Zhang, V. Liu, Z. Xia, K. L. Pothoven, and C. Lee. 2008. Cutting edge: TGF-beta-induced expression of Foxp3 in T cells is mediated through inactivation of ERK. J. Immunol. 180:2757-2761.

Marie, J. C., J. J. Letterio, M. Gavin, and A. Y. Rudensky. 2005. TGF-0.1 maintains suppressor function and Foxp3 expression in CD4+CD25+ regulatory T cells. J. Exp. Med. 201:1061-1067. doi:10.1084/jem.20042276

Nakanishi, J., Y. Wada, K. Matsumoto, M. Azuma, K. Kikuchi, and S. Ueda. 2007. Overexpression of B7-H1 (PD-L1) significantly associates with tumor grade and post operative prognosis in human urothelial cancers. Cancer Immunol. Immunother. 56:1173-1182. doi: 10.1007/s00262-006-0266-z Nomi, T., M. Sho, T. Akahori, K. Hamada, A. Kubo, H. Kanehiro, S. Nakamura, K. Enomoto, H. Yagita, M. Azuma, and Y. Nakajima. 2007. Clinical significance and therapeutic potential of the programmed death-1 ligand/programmed death-1 pathway in human pancreatic cancer. Clin. Cancer Res. 13:2151-2157. doi:10.1158/1078-0432.CCR-06-2746

Ohigashi, Y., M. Sho, Y. Yamada, Y. Tsurui, K. Hamada, N. Ikeda, T. Mizuno, R. Yoriki, H. Kashizuka, K. Yane, et al. 2005. Clinical significance of programmed death-1 ligand-1 and programmed death-1 ligand-2 expression in human esophageal cancer. Clin. Cancer Res. 11:2947-2953. doi:10.1158/1078-0432.CCR-04-1469

Probst, H. C., K. McCoy, T. Okazaki, T. Honjo, and M. van den Broek. 2005. Resting dendritic cells induce peripheral CD8+ T cell tolerance through PD-1 and CTLA-4. Nat. Immunol. 6:280-286. doi:10.1038/ni1165

Pyzik, M., and C. A. Piccirillo. 2007. TGF-beta1 modulates Foxp3 expression and regulatory activity in distinct CD4+ T cell subsets. J. Leukoc. Biol. 82:335-346. doi:10.1189/jlb.1006644

Qu, Y., B. Zhang, L. Zhao, G. Liu, H. Ma, E. Rao, C. Zeng, and Y. Zhao. 2007. The effect of immunosuppressive drug rapamycin on regulatory CD4+CD25+Foxp3+ T cells in mice. Transpl. Immunol. 17:153-161. doi:10.1016/j.trim.2007.01.002

Ramsdell, F. 2003. Foxp3 and natural regulatory T cells: key to a cell lineage? Immunity. 19:165-168. doi:10.1016/S1074-7613(03)00207-3

Riley, J. L., M. Mao, S. Kobayashi, M. Biery, J. Burchard, G. Cavet, B. P. Gregson, C. H. June, and P. S. Linsley. 2002. Modulation of TCR-induced transcriptional profiles by ligation of CD28, ICOS, and CTLA4 receptors. Proc. Natl. Acad. Sci. USA. 99:11790-11795. doi:10.1073/pnas.162359999

Roncarolo, M. G., and M. Battaglia. 2007. Regulatory T-cell immunotherapy for tolerance to self antigens and alloantigens in humans. Nat. Rev. Immunol. 7:585-598. doi:10.1038/nri2138

Rubtsov, Y. P., and A. Y. Rudensky. 2007. TGFbeta signalling in control of T-cell-mediated self-reactivity. Nat. Rev. Immunol. 7:443-453. doi:10.1038/nri2095

Sakaguchi, S., T. Yamaguchi, T. Nomura, and M. Ono. 2008. Regulatory T cells and immune tolerance. Cell. 133:775-787. doi:10.1016/j.cell.2008.05.009

Sauer, S., L. Bruno, A. Hertweck, D. Finlay, M. Leleu, M. Spivakov, Z. A. Knight, B. S. Cobb, D. Cantrell, E. O'Connor, et al. 2008. T cell receptor signaling controls Foxp3 expression via PI3K, Akt, and mTOR. Proc. Natl. Acad. Sci. USA. 105:7797-7802. doi:10.1073/pnas.0800928105

Schubert, L. A., E. Jeffery, Y. Zhang, F. Ramsdell, and S. F. Ziegler. 2001. Scurfin (FOXP3) acts as a repressor of transcription and regulates T cell activation. J. Biol. Chem. 276:37672-37679. doi:10.1074/jbc.M104521200

Setoguchi, R., S. Hori, T. Takahashi, and S. Sakaguchi. 2005. Homeostatic maintenance of natural Foxp3+ CD25+ CD4+ regulatory T cells by interleukin (IL)-2 and induction of autoimmune disease by IL-2 neutralization. J. Exp. Med. 201:723-735. doi:10.1084/jem.20041982

Sharpe, A. H., E. J. Wherry, R. Ahmed, and G. J. Freeman. 2007. The function of programmed cell death 1 and its ligands in regulating autoimmunity and infection. Nat. Immunol. 8:239-245. doi:10.1038/ni1443

Strauss, L., T. L. Whiteside, A. Knights, C. Bergmann, A. Knuth, and A. Zippelius. 2007. Selective survival of naturally occurring human CD4+CD25+Foxp3+ regulatory T cells cultured with rapamycin. J. Immunol. 178:320-329.

Strome, S. E., H. Dong, H. Tamura, S. G. Voss, D. B. Flies, K. Tamada, D. Salomao, J. Cheville, F. Hirano, W. Lin, et al. 2003. B7-H1 blockade augments adoptive T-cell immunotherapy for squamous cell carcinoma. Cancer Res. 63:6501-6505.

Tang, Q., and J. A. Bluestone. 2008. The Foxp3+ regulatory T cell: a jack of all trades, master of regulation. Nat. Immunol. 9:239-244. doi:10.1038/ni1572

Tang, Q., K. J. Henriksen, E. K. Boden, A. J. Tooley, J. Ye, S. K. Subudhi, X. X. Zheng, T. B. Strom, and J. A. Bluestone. 2003. Cutting edge: CD28 controls peripheral homeostasis of CD4+CD25+ regulatory T cells. J. Immunol. 171:3348-3352.

Thompson, R. H., M. D. Gillett, J. C. Cheville, C. M. Lohse, H. Dong, W. S. Webster, K. G. Krejci, J. R. Lobo, S.

Sengupta, L. Chen, et al. 2004. Costimulatory B7-H1 in renal cell carcinoma patients: Indicator of tumor aggressiveness and potential therapeutic target. Proc. Natl. Acad. Sci. USA. 101:17174-17179. doi:10.1073/pnas.0406351101

Vignali, D. A., L. W. Collison, and C. J. Workman. 2008. How regulatory T cells work. Nat. Rev. Immunol. 8:523-532. doi:10.1038/nri2343

Williams, L. M., and A. Y. Rudensky. 2007. Maintenance of the Foxp3 dependent developmental program in mature regulatory T cells requires continued expression of Foxp3. Nat. Immunol. 8:277-284. doi:10.1038/ni1437

Winstead, C. J., J. M. Fraser, and A. Khoruts. 2008. Regulatory CD4+CD25+Foxp3+ T cells selectively inhibit the spontaneous form of lymphopenia-induced proliferation of naïve T cells. J. Immunol. 180:7305-7317.

Wu, C., Y. Zhu, J. Jiang, J. Zhao, X. G. Zhang, and N. Xu. 2006. Immunohistochemical localization of programmed death-1 ligand-1 (PD-L1) in gastric carcinoma and its clinical significance. Acta Histochem. 108:19-24. doi:10.1016/j.acthis.2006.01.003

Yang, X. O., R. Nurieva, G. J. Martinez, H. S. Kang, Y. Chung, B. P. Pappu, B. Shah, S. H. Chang, K. S. Schluns, S. S. Watowich, et al. 2008. Molecular antagonism and plasticity of regulatory and inflammatory T cell programs. Immunity. 29:44-56. doi:10.1016/j.immuni0.2008.05.007

Zhang, P., D. M. Su, M. Liang, and J. Fu. 2008. Chemopreventive agents induce programmed death-1-ligand 1 (PD-L1) surface expression in breast cancer cells and promote PD-L1-mediated T cell apoptosis. Mol. Immunol. 45:1470-1476. doi:10.1016/j.molimm.2007.08.013

Example X

Methods Employed in the Examples

Mice 6-8 week old wild type C57BL/6 and CD45.1 (B6.5JL-Ptprc$^a$ Pepc$^b$/BoyJ) mice were purchased from The Jackson Laboratory. PD-L1$^{-/-}$PD-L2$^{-/-}$ (Keir et al. (2006) J. Exp. Med. 203:883), PD-L1$^{-/-}$ (Latchman et al. (2004) Proc. Natl. Acad. Sci. USA 101:10691), PD-L2$^{-/-}$,PD-1$^{-/-}$ (Keir et al. (2007) J Immunol 179:5064) and B7-1$^{-/-}$ (Freeman et al. (1993) Science 262:907) mice were generated in lab. Rag 2$^{-/-}$ mice (B6.129S6Rag2$^{tm1Fwa}$ N12) were purchased from Taconic. PD-L1$^{-/-}$PD-L2$^{-/-}$Rag 2$^{-/-}$ mice were generated by breeding PD-L1$^{-/-}$PD-L2$^{-/-}$ with Rag 2$^{-/-}$ mice. PD-L1$^{-/-}$, PD-1$^{-/-}$ and B7-1$^{-/-}$ mice were bred to Foxp3-IRES-GFP knock-in mice (Foxp3.GFP) on the C57BL/6 background. Genotypes were verified by PCR and flow cytometry. Mice were maintained in a pathogen-free facility and used according to Harvard Medical School and National Institutes of Health Animal Care Guidelines.

Reagents

The following anti-mouse antibodies were used in cell surface staining, intracellular cytokine staining and epoxy bead conjugation: anti-CD16/CD32 (Fc Block); CD4 PCP-Cy5.5 (clone RM4-5); CD62L PE (clone MEL-14); IL-2 APC (clone JES6-5H4) (eBiosciences); CD45.1 APC (clone A20); IL-17 PE (clone TC11-18H10); and IFN-γ PE (clone XMG1.2) and anti-B7-1 (clone 16-10A1) (BD Biosciences). Anti-CD3 (clone 2C11) plus anti-CD28 (clone 37.51) were used for bead conjugation and were purchased from BioXcell. Cells were sorted on a BD FACSAria cell sorter (BD Biosciences). Cell surface staining was performed at 4° C. in FACs Buffer (1% FCS, PBS, 2 mM EDTA, Invitrogen). Carboxyfluorescein succinimidyl ester (CFSE) was purchased from Molecular Probes.

Cell Purification

Naïve CD4$^+$CD62L$^+$Foxp3.GFP$^-$ T cells were isolated from the spleen and lymph nodes (axillary, brachial and inguinal) of male C57BL/6 Foxp3.GFP reporter mice. Single cell suspensions were made by mechanical dissociation. Following red blood cell lysis with ACK buffer (GIBCO), cells were washed and isolated by incubation with CD4 microbeads and positively selected through LS columns (Miltenyi Biotec) and stained with anti-CD4 PCP-Cy5.5 (clone RM4-5, eBiosciences) and anti-CD62L APC (clone MEL-14, eBiosciences) prior to cell sorting on a FACSAria cell sorter (BD Biosciences). Naïve CD4$^+$CD62L$^+$Foxp3.GFP$^-$ T cells were always>98.2% pure.

In Vitro Induced Treg Development

Anti-CD3 (clone 2C11, Bioexpress) plus anti-CD28 (clone 37.51, Bioexpress) were covalently attached to Dynabeads M450 glycidyl ether beads following the manufacturer's directions (Invitrogen). Equal loading of proteins during preparation was ensured by keeping constant the molar ratios of the antibodies as described (Broeren et al. (2000) J. Immunol. 165:6908; Riley et al. (2002) Proc. Natl. Acad. Sci. USA 99:11790). In general, for each 10$^7$ beads, 1 microgram of anti-CD3 (20% of total protein) and 1 microgram of anti-CD28 were coated with either 60% control human Ig1 (BioXcell) or 40% PD-L1-hIgG1Fc or PD-L2-Ig fusion protein (referred to as PD-L1-Ig or PD-L2-Ig) (R&D Systems) plus 20% control human IgG1Fc (referred to as Ctrl-Ig). In some experiments, increasing amounts of PD-L1-Ig or PD-L2-Ig were used to coat the epoxy beads (20%, 40% and 60% of total protein per 10$^7$ beads=1, 2 and 3 μg of PD-L1-Ig per 10$^7$ beads). In these cases, the remaining surface of the beads were coated with control human IgG1. Covalent attachment of the proteins to the beads was carried out in NaPO$_4$ buffer for 24 hours at room temperature on a Nutating Mixer (Labtech Technologies Inc). Beads were then washed three times in PBS over a magnetic column and resuspended in complete media prior to use.

CD4$^+$CD62L$^+$Foxp3$^-$ naïve T cells were cultured with beads at a fixed ratio of 1:5 (T cells: beads). Briefly, 1–2×10$^6$ T cells were plated at 1×10$^6$/mL in a 24 well flat-bottom tissue culture plate with beads in complete media consisting of RPMI-1640 with L-glutamine (Invitrogen) supplemented with 10% fetal calf serum (FCS) (Sigma), penicillin-streptomycin (100 units penicillin and 100 μg streptomycin, Invitrogen), 12 mM HEPES (Invitrogen) and 50 μM β-mercaptoethanol (Sigma) plus 2-5 ng/mL TGF-β (R&D Systems) for three days at 37° C. with 5% CO$_2$.

In Vitro Suppression Assays

Naïve T cells were induced toward Treg development in vitro using PD-L1 or control beads in the presence of TGF-β and IL-2 (200 U/mL, Roche) for three days, at which time Foxp3.GFP$^+$ T cells were sorted on a BD FACSAria cell sorter. Foxp3.GFP$^+$ iTregs were then co-cultured with sorted CD4$^+$CD25$^-$CD45.1$^+$ naïve Teff cells and stimulated with PD-L1 beads (containing anti-CD3 (20%), anti-CD28 (20%), PD-L1-Ig (40%) and Ctrl-Ig (20%)) for three days. Proliferation of T cells was determined by incorporation of $^3$H-thymidine (1 μCi/well) for 12-14 hours. Suppression assays were performed using a constant number of Teffs (1×10$^5$) and the addition of decreasing numbers of Foxp3.GFP$^+$ iTregs plus a 5:1 ratio of beads to Teffs. Percent suppression of effector cell proliferation was calculated based on the proliferation of Teffs with either control or PD-L1-beads in the absence of Tregs.

For CFSE dilution experiments, CD4$^+$CD25$^-$CD45.1$^+$ naïve Teffs were labeled with 1 μM CFSE for 10 minutes in RPMI-1640 (serum-free) and washed twice with 100% fetal bovine serum (FBS) and twice with complete media prior to culture. 1×10$^5$ Teffs were cultured with 1×10$^5$ iTregs and PD-L1-Ig beads (5:1) in 96-well flat-bottom plates (Becton Dickinson). 72 hours post-co-culture, CD4$^+$CD45.1$^+$ T cells were gated and analyzed for CFSE dilution. Division index (defined as the average number of divisions that a cell has undergone) was calculated using FlowJo Proliferation analysis software.

In Vivo Adoptive Transfer

Naïve CD4$^+$ T cells were isolated from spleens and lymph nodes of C57BL/6 mice and CD4$^+$CD62L$^{hi}$Foxp3.GFP$^-$ cells were sorted on a FACSAria as described above. 1–1.5× 10$^6$ CD4$^+$CD62L$^{hi}$Foxp3.GFP$^-$ were intravenously (i.v.) injected into the tail veins of PD-L1$^{-/-}$PD-L2$^{-/-}$Rag$^{-/-}$ or WT Rag$^{-/-}$ mice. Mice were monitored and weighed for 14-17 days and euthanized for histological and cellular analysis. Organs were fixed in formalin, dehydrated, and embedded in paraffin. Five micron sections stained with hematoxylin and eosin were independently evaluated by two pathologists in a blinded fashion. Digital photomicrographs were acquired using Olympus DP Controller software driving an Olympus DP71 camera mounted on an Olympus BH-2 light microscope. Image sizes were reduced using Adobe Photoshop CS3 software.

Intracellular Cytokine Staining

Spleen and lymph node (axillary, brachial, inguinal, mesenteric) cells were isolated and re-stimulated with PMA (50 ng/mL) and ionomycin (500 ng/mL) (Sigma-Aldrich) for four hours with Golgistop (BD Biosciences) being added during the last three hours of stimulation. Following Fc block, cells were stained with anti-CD4 PCP-Cy5.5, fixed with 4% paraformaldehyde and permeabilized with Cytofix/Cytoperm solution (BD Biosciences). Intracellular staining with IL-17 PE, IFN-γ PE or APC and IL-2 APC was carried out in Cytoperm Buffer (BD Biosciences) according to the manufacturers protocol, washed twice in Cytoperm Buffer and twice in Facs Buffer prior to acquisition on a BD FACSCalibur (BD Biosciences), and analyzed by FlowJo software (Treestar).

Phospho-Flow Cytometry

Naïve CD4$^+$ T cells were sorted from 2D2Foxp.3GFP reporter mice and cultured with either PD-L1-Ig beads or control beads in the presence of 2 ng/mL TGF-β and 20 U/mL IL-2 for 18 hours. Signaling molecules were assessed with antibodies against phospho-Akt Ser473 Alexa Fluor 647 (clone D9E), phospho-mTOR Ser24448 (clone 49F9), phospho-S6 Ser 235/236 Alexa Fluor 647 (clone D57.2.2E), and PTEN Alexa Fluor 647 (clone 138G6; Cell Signaling Technology). Isotype control staining was performed using rabbit IgG isotype mAb Alexa Fluor 647 (DAZE; Cell Signaling Technology). P-mTOR was detected with anti-rabbit Alexa Fluor 647 secondary (Invitrogen). Intracellular staining was performed as described in the manufacturer's protocol. In brief, T cells were collected and washed thoroughly with PBS in 96-well V-bottom plates. Cells were then fixed with 2% paraformaldehyde for 10 minutes at 37° C. After fixation, plates were pre-chilled on ice for one minute before permeabilization by slowly adding ice-cold methanol to a final concentration of 90% methanol. Cells were then incubated on ice for 30 minutes for permeabilization before being washed with 1% FCS/PBS (incubation buffer). Cells were blocked with 10% FCS/PBS for ten minutes at room temperature and subsequently stained with the antibodies listed in this section for one hour at room temperature. After incubation, cells were washed four times with incubation buffer and brought up in PBS before analysis.

Statistical Analysis

Statistical analysis of Foxp3$^+$ Treg development, Teff cell proliferation and intracellular cytokine production was performed using Students t-tests. PD-L1-Ig titration, TGF-β titration, and percent weight loss were analyzed by ANOVA. Log-rank tests were used to compare WT Rag$^{-/-}$ and PD-L1$^{-/-}$PD-L1$^{-/-}$PD-L2$^{-/-}$Rag$^{-/-}$ survival post-transfer of naïve T cells. P values of less than 0.05 were considered statistically significant.

What is claimed is:

1. A method of generating an induced regulatory T cell (iTreg) comprising the steps of:
   a) isolating a CD4$^+$ Foxp3$^-$ naïve T cell;
   b) contacting the isolated naïve T cell with PD-L1 and/or PD-L2; and
   c) examining the T cell for Foxp3 expression and/or the ability to suppress effector T cell (Teff) activation, wherein Foxp3 expression and/or the ability to suppress Teff activation is indicative of an iTreg.

2. The method of claim 1, wherein the PD-L is immobilized.

3. The method of claim 2, wherein the PD-L is immobilized on a bead or a cell.

4. The method of claim 1, wherein the step of differentiating is performed in the presence of anti-CD3 antibody or anti-CD28 antibody.

5. The method of claim 4, wherein the anti-CD3 antibody or the anti-CD28 antibody are present on a bead.

6. The method of claim 1, wherein the step of differentiating is performed in the presence of transforming growth factor-beta (TGF-β).

7. The method of claim 1, wherein the iTreg expresses forkhead box p3 (Foxp3).

8. The method of claim 1, wherein the iTreg suppresses effector T cell (Teff) activation.

9. The method of claim 8, wherein the Teff is a CD4$^+$ Teff.

10. The method of claim 1, wherein the PD-L antagonizes the Akt signaling pathway.

* * * * *

UNITED STATES PATENT AND TRADEMARK OFFICE
CERTIFICATE OF CORRECTION

| | | |
|---|---|---|
| PATENT NO. | : 9,580,684 B2 | Page 1 of 1 |
| APPLICATION NO. | : 13/223372 | |
| DATED | : February 28, 2017 | |
| INVENTOR(S) | : Sharpe et al. | |

It is certified that error appears in the above-identified patent and that said Letters Patent is hereby corrected as shown below:

In the Specification

Under STATEMENT OF GOVERNMENT INTERESTS
Column 1, Line 16:
Please delete "This invention was made with government support under R37AI038310, R01 AI40614, P01 AI056299 and P01 AI39671 awarded by the National Institutes of Health. The Government has certain rights in the invention."
And insert -- This invention was made with government support under AI038310, AI040614, AI056299 and AI039671 awarded by the National Institutes of Health. The government has certain rights in the invention. --

Signed and Sealed this
Second Day of June, 2020

Andrei Iancu
*Director of the United States Patent and Trademark Office*